(12) United States Patent
Scolastico et al.

(10) Patent No.: US 6,451,972 B1
(45) Date of Patent: *Sep. 17, 2002

(54) PEPTIDO-MIMETIC COMPOUNDS CONTAINING RGD SEQUENCE USEFUL AS INTEGRIN INHIBITORS

(75) Inventors: Carlo Scolastico, Milan; Giuseppe Giannini, Pomezia, both of (IT)

(73) Assignee: Sigma-Tau Industrie Farmaceutiche Riunite S.p.A., Rome (IT)

(*) Notice: Subject to any disclaimer, the term of this patent is extended or adjusted under 35 U.S.C. 154(b) by 0 days.

This patent is subject to a terminal disclaimer.

(21) Appl. No.: 09/777,013

(22) Filed: Feb. 6, 2001

Related U.S. Application Data

(63) Continuation-in-part of application No. 09/366,198, filed on Aug. 4, 1999, now Pat. No. 6,235,877.

(30) Foreign Application Priority Data

Nov. 16, 1998 (IT) .......................................... MI98A2477

(51) Int. Cl.⁷ ................................................ A61K 38/08

(52) U.S. Cl. ........................ 530/330; 530/317; 530/333; 530/338

(58) Field of Search ................................. 530/330, 317, 530/333, 338

*Primary Examiner*—Christopher S. F. Low
*Assistant Examiner*—David Lukton
(74) *Attorney, Agent, or Firm*—Nixon & Vanderhye P.C.

(57) ABSTRACT

Compounds of formula (I)

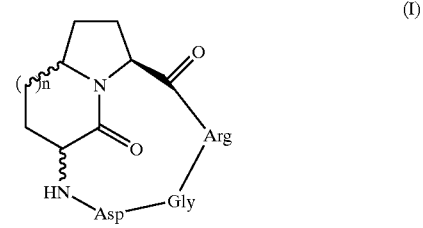

where n is the number 0, 1 or 2, processes for the preparation together with methods for treating pathologies related to an altered $\alpha_v\beta_3$ integrin-mediated cell attachment, in particular where inhibition of angiogenesis is desired, for example in tumors, also associated with metastasis.

2 Claims, 12 Drawing Sheets

Fmoc-Temp1

Fmoc-Temp2

Fmoc-Temp3

Fmoc-Temp4

Fmoc-Temp5

Fmoc-Temp6

Fmoc-Temp7

Fmoc-Temp8

9

10

11

12

13

14

15

16

17

18

19

20

21

22

PEPTIDO-MIMETIC COMPOUNDS CONTAINING RGD SEQUENCE USEFUL AS INTEGRIN INHIBITORS

This application is a continuation-in-part of application Ser. No. 09/366,198, filed Aug. 4, 1999, now U.S. Pat. No. 6,235,877 entire content of which is hereby incorporated by reference in this application.

The present invention relates to cyclic peptido-mimetic compounds, in particular to cyclic peptido-mimetic compounds having azabicycloalkane structure and containing the RGD (Arg-Gly-Asp) sequence. Said compounds have inhibiting action on $\alpha_v\beta_3$-receptor of the integrin family. The compounds of the present invention are endowed with antiangiogenic properties, hence are useful as medicaments, preferably for the treatment of tumors.

BACKGROUND OF THE INVENTION

The first molecule with antiangiogenic activity was discovered in 1975 by Henry Brem and Judah Folkman in cartilaginous tissues.

In the 80s it was found that interferon ($\alpha/\beta$) is effective in inhibiting tumor angiogenesis.

In 1998, it was widely published, also in the media, that angiostatin and endostatin discovered by J. Folkman at Harvard Medicinal School and Boston Children's Hospital were giving very encouraging results in tumor treatment.

To-date, about 30 molecules are tested in clinical trials (Phase I–III).

Of these 30 molecules, only two drugs, of which one is an antibody, are in clinical trials for their activity in inhibiting endothelial specific integrins.

It is calculated that only in the USA, about 9 million patients could benefit from an antiangiogenic therapy.

Recently, FDA has approved clinical trials for the combination of IL-10 with Thalidomide and Methoxyestradiol.

Angiogenesis is intended as the formation of new capillary blood vessels. This natural phenomenon is involved both in physiological processes, as reproduction, and in pathological occurrences, as wound healing, arthritis and tumor vascularization.

A number of growth factors have been identified as capable of promoting angiogenesis, through direct induction of proliferation and/or chemiotaxis of endothelial cells. Other factors, instead, act indirectly, by stimulating other cell types (mast cells, macrophages), which, on their turn, produce angiogenic factors. The presence of growth factors, such as bFGF and VEGF, near a resting capillary net, suggested that angiogenesis might be the outcome of an unbalance between pro-and anti-angiogenic factors.

In the last years, it was reported that tumor growth and metastasis formation is strictly dependent on the development of new vessels capable of vascularizing the tumor mass.

Antiangiogenic tumor therapy is strongly desired by physicians for the following reasons:

specificity: tumor neovascularization is the target;
bioavailability: the antiangiogenic agent is targeted toward endothelial cells, easily reached without the well-known problems of chemotherapy, which is directed on the tumor cell;
chemoresistance: this is the most striking advantage, in fact, endothelial cells are genetically stable and it is quite difficult to observe drug resistance;
angiogenic blockade avoids metastatic cells to diffuse through blood circulation;
apoptosis: blocking angiogenesis makes tumor cell suffer from oxygen and nutrition lack, thus inducing apoptosis;
antiangiogenic therapy does not give rise to side effects typical of chemotherapy.

The endogenous pro-angiogenic factors to date known are acid/basic Fibroblast Growth factor (a/bFGF) and Vascular Endothelial Growth Factor (VEGF), and its subtype B and C, Angiogenin, Endothelial Growth Factor (EGF), Platelet derived-Endothelial Cell Growth Factor (PD-ECGF), Transforming Growth Factor-$\alpha$ (TGF-$\alpha$), Transforming Growth Factor-$\beta$ (TGF-$\beta$), Tumor Necrosis Factor-$\alpha$ (TNF-$\alpha$).

Retinoids are tested as potential antiangiogenic agents.

Some PK-C inhibitors, such as Calphostin-C, phorbol esters and Staurosporin, can block angiogenesis, either partially or totally.

Integrins are a class of receptors involved in the mechanism of cell adhesion and alterations in the function of these receptors are responsible in the occurrence of a number of pathologic manifestations, for example embryogenic development, blood coagulation, osteoporosis, acute renal failure, retinopathy, cancer, in particular metastasis. Among the molecular targets involved in angiogenesis, $\alpha_v\beta_3$ integrins play an important role in adhesion, motility, growth and differentiation of endothelial cells. $\alpha_v\beta_3$ integrins bind the RGD sequence (Arg-Gly-Asp), which constitutes the recognition domain of different proteins, such as laminin, fibronectin and vitronectin. The RGD sequence represent the minimal amino acid domain, in several extra-cellular matrix proteins, which has been demonstrated to be the binding site of the transmembrane integrins proteins family (G. Bazzoni, E. Dejana and M. G. Lampugnani. 1999, Current Opinion in Cell Biology; (11) pp. 573–581). Indeed replacement of just one single amino acid of this short sequence result in loss of binding activity to integrins (F. E. Ali, R. Calvo, T. Romoff, I. Samanen, A. Nichols. 1990, Peptides: Chemistry. Structure and Biology (Eds: J. E. Rivier, G. R. Marshall) ESCOM Science Leiden (Netherland) pp. 94–96). In the last years has been demonstrated that RGD peptide isolated from phage peptides library or biochemically synthesised, were able to compete with extracellular matrix proteins to bind integrins (R. Haubner, D. Fisinger and H. Kessler. 1997, Angew. Chem. Int. Ed. Engl. ; (36) pp. 1374–1389).

The role of RGD sequence is described, for example, in Grant et al., J. Cell Physiology, 1992, Saiki et al., Jpn. J. Cancer Res. 81; 668–75. Carron et al, 1998, Cancer Res. 1; 58(9):1930–5 disclosed an RGD-containing tripeptide, named:SC-68448, capable of inhibiting the binding between $\alpha v\beta 3$ integrin with vitronectin ($IC_{50}$=1 nM). Other works (Sheu et al., 1197, BBA; 1336(3):445–54—Buckle at al., 1999, Nature 397:534–9) showed that RGD peptides can diffuse through the cell membrane and bind to the protein caspase-3, inducing apoptosis.

Therefore, RGD sequence is the basis for developing antagonists of the different integrins. To date, the reasons for which in many cases a high selectivity for certain integrins is observed is not quite clear, although a different conformation of the RGD sequence can be taken as an explanation. Recent data demonstrated that this sequence is often inserted into a type II-$\beta$-turn between two $\beta$-sheets extending from the core of the protein.

Thus the problem to provide substances having high selectivity toward integrins has not been fully satisfied yet.

There is a structural constraint to this research, namely, the RGD sequence must be kept unaltered, since it is well known that any modification to this sequence implies a loss of activity.

To find the correct structure that can block the molecule in a precise reverse-turn conformation, inducing a β-turn geometry, is very critical.

It is well known that the $\alpha_v\beta_3$-receptor, a member of the integrin family, is implicated in angiogenesis and in human tumor metastasis.

Metastasis of several tumor cell lines as well as tumor-induced angiogenesis can be inhibited by antibodies or small, synthetic peptides acting as ligands for these receptors (Friedlander et al.: Science 1995, 270, 1500–1502).

In order to have an inhibiting property, all the peptides must contain the Arg-Gly-Asp (RGD) sequence. Notwithstanding this RGD sequence, a high substrate specificity is present, due to different conformations of the RGD sequence in different matrix proteins (Ruoshlati et al. Science 1987, 238, 491–497). This flexibility of particular RGD portion is an obstacle to the determination of the bioactive conformation to be used in the widespread structure-activity drug design.

A solution was provided by Haubner et al. (J. Am. Chem. Soc. 1996, 118, 7881–7891) by inserting the RGD sequence in cyclic, rigid peptide structure. Spatial screening led to the highly active first-generation peptide c(RGDfV) (cyclic Arg-Gly-Asp-D-Phe-Val; WO97/06791), which shows a βII'/γ-turn arrangement. A reduction of the flexibility is a technical goal to be achieved in order to obtain antagonists of integrins. Due to the width of the integrin family and to the number of different physiological activities of said integrins, it is highly desired to obtain active agents having highly selective inhibiting action.

A solution proposed in the art was to introduce in the peptido-mimetic structure a rigid building block (turn mimetics).

Despite different tentatives and a number of structures proposed, Haubner et al. (J. Am. Chem. Soc. 1996, 118, 7881–7891), identified an RGD"spiro" structure capable of providing the desired βII'/γ-turn arrangement. Actually, four different structures are enabled in this work: an (S)-proline derivative, an (R)-proline derivative, a thiazabicyclo structure and a diaza-spiro-bicyclic structure. Non-homogeneous results were obtained. The spiro structure was the only one able to adopt a βII'/γ-turn conformation, but lacks of biological activity. The (R)-proline is very active, but less selective. The (S)-proline is active and selective. The thiazabicyclo-structure is active, but has the disadvantage to be less selective.

WO91/15515 discloses cyclic peptides, also containing the RGD sequence, useful for treating thrombosis, through the selective inhibition of the platelet aggregation receptor GPIIb/IIa.

WO92/17492 discloses cyclic peptides, also containing the RGD sequence, useful for treating thrombosis, through the selective inhibition of the platelet aggregation receptor GPIIb/IIa. These peptides contain also a positively charged nitrogen containing exocyclic moiety stably bonded to the cyclic peptide through a carbonyl. No beta-turns are contained in these structures.

WO94/29349 discloses a long peptide containing a -Cys-S-S-Cys-cyclic portion for the treatment of a venous or arterial thrombotic condition. This trifunctional peptide combines both catalytic and anion binding exosite inhibition of thrombin with GP IIb/IIIa receptor inhibition.

Other peptides active in treating thrombosis are disclosed in WO95/00544.

WO97/06791 discloses the use of c(RGDfV) as selective inhibitor of $\alpha_v/\gamma_5$ and useful as inhibitor of angiogenesis.

WO97/08203 discloses circular RGD-containing peptides, which comprise the motif (/P)DD(G/L)(W/L)(W/L/M).

U.S. Pat. Nos. 5,767,071 and 5,780,426 disclose non-RGD amino acid cyclic peptides binding $\alpha_v/\gamma_3$ integrin receptor.

U.S. Pat. No. 5,766,591 discloses RGD-peptides for inhibiting $\alpha_v/\gamma_3$ receptor and useful as antiangiogenesis agents. No beta turn portions are taught.

WO98/56407 and WO98/56408 disclose fibronectin antagonists as therapeutic agents and broad-spectrum enhancers of antibiotic therapy. Said fibronectin antagonists bind to a $\alpha_5\beta_1$ integrin to the purpose to prevent intracellular invasion by microbial pathogens. Some of these inhibitors are linear or cyclic peptides containing the RGD structure or antibodies. Integrin antagonists are specifically disclosed for their selectivity against $\alpha_5\beta_1$ integrin. The best of them proved to be (S)-2-[2,4,6-trimethylphenyl)sulfonyl]amino-3-[[7benzyloxycarbonyl-8-(2-pyridinylaminomethyl)-1-oxa-2,7-diazaspiro-[4,4]-non-2-en-3-yl]carbonylamino] propionic acid.

U.S. Pat. No. 5,773,412 discloses a method for altering $\alpha v\beta 3$ integrin receptor-mediated binding of a cell to a matrix, said cell being an endothelial or smooth muscle cell, by contacting said cell with a RGD-containing cyclic peptide. Also disclosed there is a method for inhibiting angiogenesis by using this cyclic peptide. The cyclic peptide disclosed in U.S. Pat. No. 5,773,412 contains at least 6 amino acids and the RGD sequence is flanked, on the D-side, by a first amino acid which can provide a hydrogen bond interaction with an integrin receptor (Asn, Ser or Thr) and a second amino acid, that has the characteristics of hydrophobicity or conformational constraint (Tic, i.e. 1,2,3,4-tetrahydroisoquinoline-3-carboxylic acid, Pro, Phe or Ile). A selection of these peptides are taught as useful for altering the binding of osteoclasts to a matrix such as bone or for selectively altering integrin receptor binding. It has now been found that cyclic pseudopeptides having an RGD mimetic structure characterized by an azabicycloalkane structure are endowed with selective inhibition of $\alpha v\beta 3$ integrin-mediated cell attachment. This activity makes them useful as therapeutical agents, in particular for treating pathologies due to an altered angiogenesis, for example tumors.

BRIEF SUMMARY OF THE INVENTION

It is an object of the present invention, compounds of formula (I)

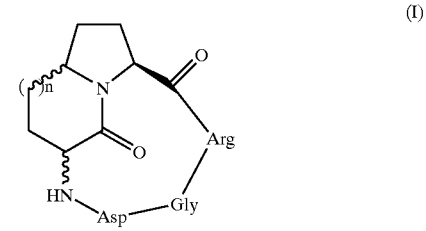

wherein n is the number 0, 1 or 2,

Arg is the amino acid L-Arginine, Gly is the amino acid Glycine and Asp is the amino acid L-Aspartic acid, and the pharmaceutically acceptable salts thereof, their racemates, single enantiomers and stereoisomers.

The compounds of formula (I) are selective inhibitors of $\alpha_v\beta_3$ receptor. Accordingly, they are useful for treating all those pathologies due to an altered $\alpha_v\beta_3$ integrin-mediated cell attachment; for example, retinopathies, acute renal failure, osteoporosis, tumors, also associated with metastasis. The compounds of the present invention can be considered as antiangiogenesis agents, in particular for the treatment of tumors, comprising tumors associated with metastasis.

Other objects of the present invention are processes for the preparation of the compounds of formula (I).

A further object of the present invention is a method for treating a subject, whether human or animal, suffering of a tumor, by inducing an inhibition of angiogenesis, in particular for inhibiting or reducing or blocking metastatic proliferation, with the administration of a therapeutic or preventive dose of at least a compound of formula (I). Also objects of the present invention are: a method for selectively inhibiting $\alpha_v\beta_3$ integrin-mediated cell attachment to an RGD-containing ligand, comprising contacting said ligand with an effective amount of a compound of formula (I); a method for treating a subject suffering from a pathology related to an altered $\alpha_v\beta_3$ integrin-mediated cell attachment comprising administering to said subject a compound of formula (I); said pathologies being for example retinopathy, acute renal failure, osteoporosis.

From the industrial application point of view, the present invention also comprises pharmaceutical compositions comprising an effective dose of at least a compound of formula (I) in admixture with pharmaceutically acceptable vehicles and/or excipients.

BRIEF DESCRIPTION OF THE DRAWINGS

The present invention shall be disclosed in detail in the foregoing also by means of examples and figures, wherein, in the figures.

DETAILED DESCRIPTION OF THE INVENTION

Figure 1:
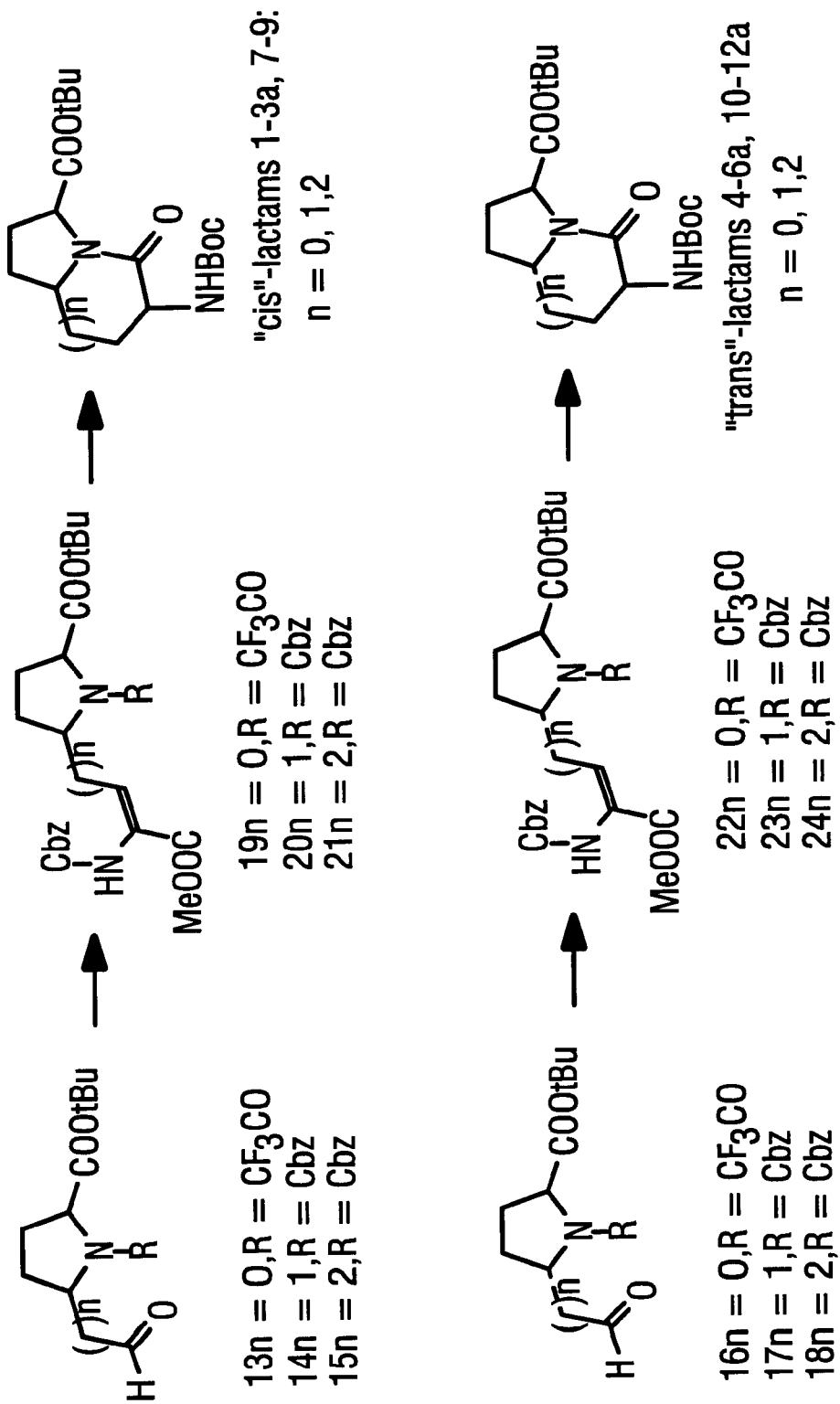
FIG. 1 represents, in an exemplary way, the general synthesis of the lactams.

In its broadest aspects, the present invention relates to compounds of the above formula (I).

The compounds of formula (I) are peptido-mimetics containing an RGD sequence. Said compounds can be seen as formed by an azabicycloalkane scaffold and an RGD sequence.

For sake of clarity, in formula (I), there is a variable part, given by the different values of n, and a fixed part, given by the RGD sequence. When n is 0, the scaffold is referred to as 5,5 azabicycloalkane, when n is 1, the scaffold is referred to as 6,5 azabicycloalkane and when n is 2, the scaffold is referred to as 7,5 azabicycloalkane. The bonds written in formula (I) as a wavy line represents a stereo bond, which can be either above the plane of the page (thick bond) either below the plane of the page (thin bond). The compounds of formula (I) can exist in different stereoisomers, according to the orientation of the wavy bond.

A first class of preferred compounds of formula (I) are 7,5 azabicycloalkane, in particular those having trans configuration as to the positions 7 and 10 and (R) configuration as to the carbon atom at position 3.

A second class of preferred compounds of formula (I) are 6,5 azabicycloalkane, in particular those having trans configuration as to the positions 6 and 9 and (S) configuration as to the carbon atom at position 3.

A particularly preferred compound is the one of the following formula (also named as ST 1646).

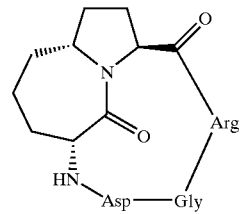

In the following table there are represented the preferred compounds of formula (I):

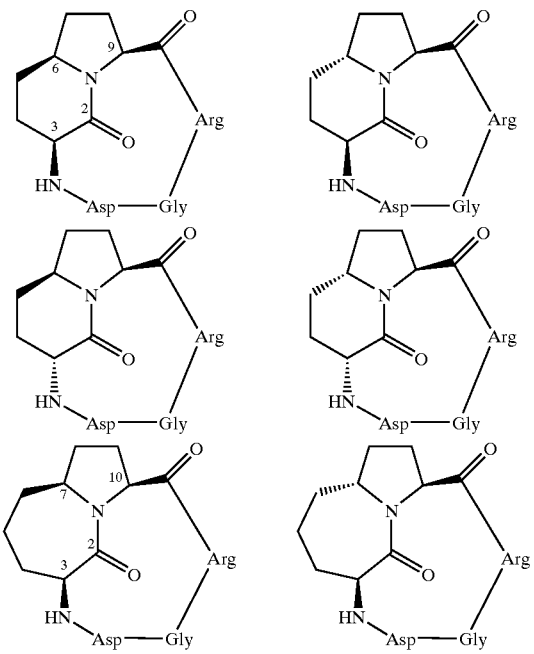

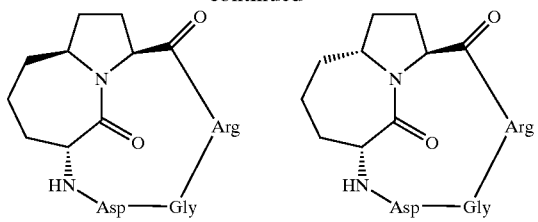

Within the boundaries of the present invention, there is disclosed a process for the preparation of the compounds of formula (I), comprising the following steps:

a) Horner-Emmons olefination of a compound of formula (II)

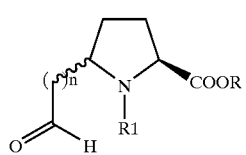

(II)

wherein
R is a lower alkyl residue;
$R_1$ is a suitable nitrogen protecting group,
to give a compound of formula (III);

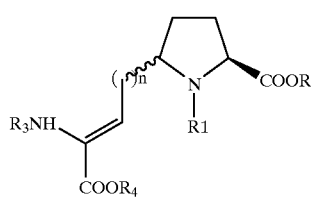

(III)

wherein $R_3$ is a suitable nitrogen protecting group, $R_4$ is a lower alkyl residue;

b) hydrogenation of said compound of formula (III) and cyclisation; and, if desired
c) separation of the stereoisomeric mixture;
d) building of the RGD cyclic sequence, and if desired
e) separation of the stereoisomeric mixture.

A process for the stereoselective synthesis of the compounds of formula (I), comprises the following steps:

a) Horner-Emmons olefination of a compound of formula (II)

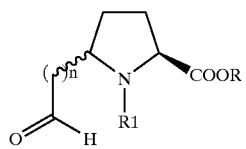

(II)

wherein
R is a lower alkyl residue;
$R_1$ is a suitable nitrogen protecting group,
to give a compound of formula (III);

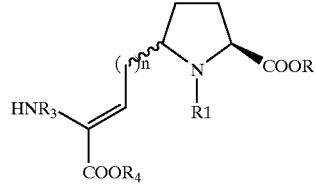

(III)

wherein $R_3$ is a suitable nitrogen protecting group, $R_4$ is a lower alkyl residue;

b) hydrogenation of said compound of formula (III) by chiral phosphine-Rh catalysed hydrogenation and cyclisation; and, if desired
c) separation of the stereoisomeric mixture;
d) building of the RGD cyclic sequence and if desired
e) separation of the stereoisomeric mixture.

As lower alkyl residue it is normally understood a $C_1$–$C_4$ alkyl, for example, methyl, ethyl, propyl, butyl and all the possible isomers, but also higher alkyls are suitable, provided their compatibility with reaction conditions. As suitable nitrogen protecting groups, the skilled person is able to select, according the general common knowledge, the suitable protecting group, as it will appear from the following examples, but also in the available technical literature and commercial catalogues.

Also disclosed are pharmaceutical compositions comprising a therapeutically or preventive effective dose of at least a compound of formula (I) in admixture with pharmaceutically acceptable vehicles and/or excipients.

In its broadest aspect, the present invention advantageously teaches a method for selectively inhibiting $\alpha_v\beta_3$ integrin-mediated cell attachment to an RGD-containing ligand, comprising contacting said ligand with an effective amount of a compound of formula (I), a method for treating a subject suffering from altered angiogenesis, comprising administering to said subject a compound of formula (I), a method for the treatment of tumors in a subject comprising administering to said subject a compound of formula (I), optionally in combination with other active ingredients, in particular other antitumour agents.

The present invention shall be described in detail also by means of examples and figures, wherein,

BEST MODES FOR CARRYING OUT THE INVENTION

The synthesis of so-called peptido-mimetics molecules has been a very active and productive field of research in drug design (J. Gante, Angew. Chem., Int. Ed. Engl. 1994, 33, 1699.—G. L. Olson, et al.: J. Med. Chem. 1993, 36, 3039.—D. C. Horwell, Bioorg.Med. Chem. Lett. 1993, 3, 797.—A. Giannis et al.: Angew. Chem., Int. Ed. Engl. 1993, 32, 1244.—B. A. Morgan: Annu. Rep. Med. Chem. 1989, 24, 243). The expectation is that these molecules will have the same biological effects as natural peptides, but at the same time, will be metabolically more stable. Of particular interest has been the replacement of reverse-turn dipeptide motifs with constrained molecules that reproduce their conformational features (ibid; M. Kahn, Ed., Peptide Secondary Structure Mimetics. Tetrahedron Symposia-in-Print No. 50 1993, 49, 3433–3689 and references therein). This goal has been frequently achieved using the azaoxobicyclo[X.Y.0] alkane skeleton and/or heteroatom analogues. This has created a demand for efficient synthetic approaches toward such molecules, and many methods have been introduced and recently reviewed (S. Hanessian et al: Tetrahedron 1997, 38, 12789–12854). One particularly effective and versatile route has been developed by Lubell et al. and employed for the preparation of enantiopure indolizidinone-type 6,5-fused bicyclic lactams (H.-G. Lombart et al.: J. Org. Chem. 1996, 61, 9437–9446.—F. Polyak et al.: J. Org. Chem. 1998, 63, 5937–5949 and references therein for the syntheses of azabicycloalkane amino acids—F. Gosselin et al.: J. Org. Chem. 1998, 63, 7463–7471). Several procedures are also available for the synthesis of 7,5-fused bicyclic lactams, the majority of which require relatively long synthetic sequences. On the contrary, there is not many published protocol that allow the synthesis of 5,5-fused bicyclic lactams.

According to the present invention, the beta-turn portion of the cyclic peptide consists in an azabicycloalkane amino acid scaffold, selected from a 5,5-, 6,5- or 7,5-fused bicyclic lactams. Several 6,5- and 7,5-fused 1-aza-2-oxabicyclo [X.3.0]alkane amino acids have been synthesised, using radical (L. Colombo et al.: Tetrahedron Lett. 1995, 36, 625–628.—L. Colombo et al.: Gazz. Chim. It. 1996, 126, 543–554) or ionic reactions (L. Colombo et al. Tetrahedron 1998, 54, 5325–5336). These structures can be regarded as conformationally restricted substitutes for Ala-Pro and Phe-Pro dipeptide units, and, if their conformations meet certain criteria, they can be used to replace the central (i+1 and i+2) residues of β-turns.

The present invention provides an improved reaction sequence, amenable to large scale preparation, and allowing the synthesis of different bicyclic lactams from common intermediates, as described in the appended FIG. 1.

Starting from 5-allyl/formyl prolines 13–18, a Z-selective Horner-Emmons olefination followed by double bond reduction has been used to build the second ring. The starting aldehydes have been stereoselectively synthesised by modifications of known procedures (vide infra). Stereorandom double bond reduction can be performed using $H_2$/Pd to yield, after cyclisation, mixtures of easily separable epimers. Stereoselective hydrogenation is studied for the synthesis of 6,5-fused lactams, and achieved with d.e. 80% using Rh-chiral phosphine catalysts. Structural diversity, in terms of ring size and stereochemistry of the azabicycloalkane fragment, is provided by the new strategy, and access to the less common 5,5-fused bicyclic scaffold is also secured.

Figure 2:
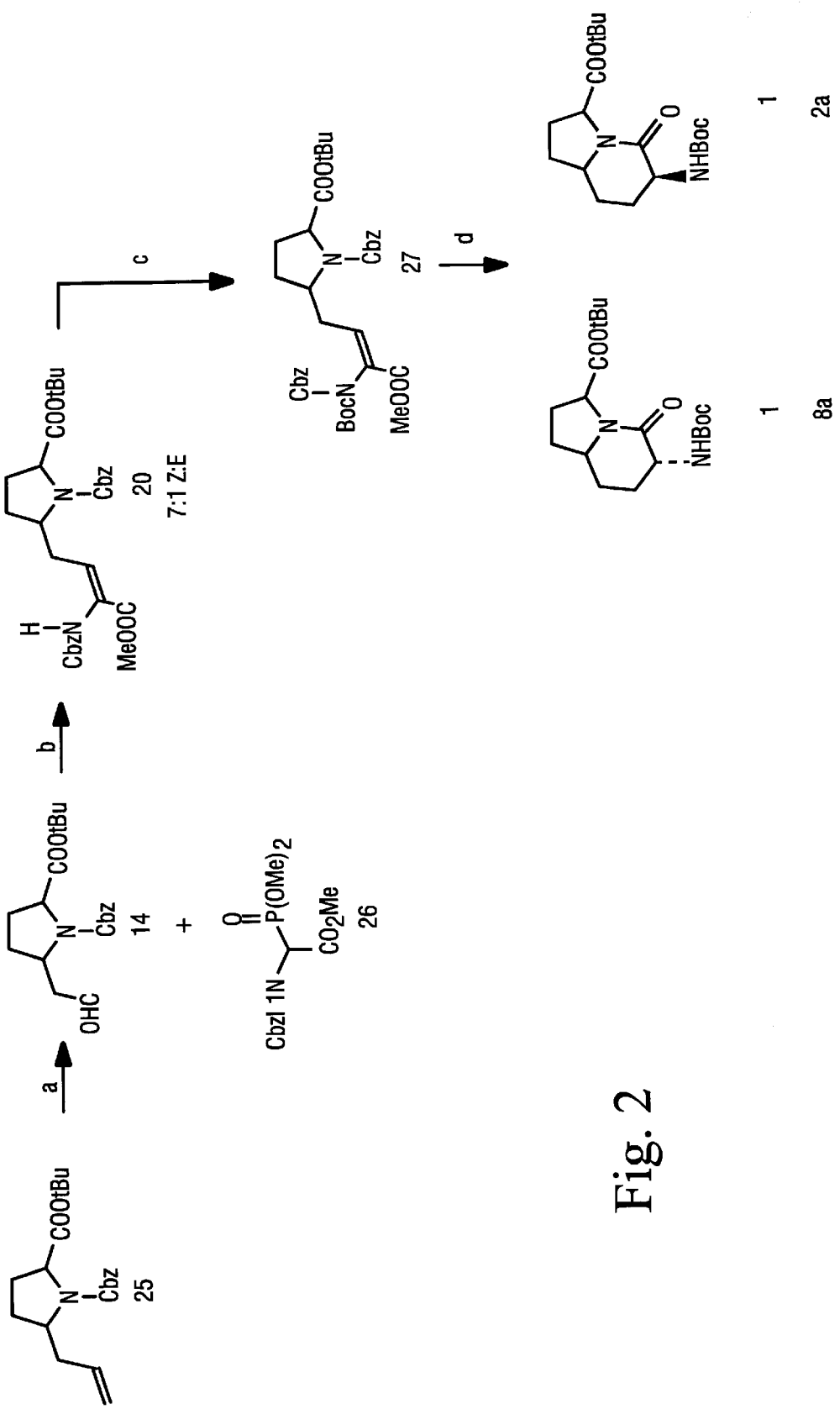
FIG. 2 represents a preferred embodiment of the synthesis of 6,5-fused "cis" lactams.

Examples of bicyclic dipeptide derivatives 1–12 are shown in FIG. 2.

Synthesis of the Fused Bicyclic Lactams 1–12

The synthesis of lactams 1–12 follows the common steps reported in FIG. 1. Starting from the cis or trans 5-alkyl proline aldehydes 13–18, a Horner-Emmons olefination with the potassium enolate of (±)-Z-α-phosphonoglycine trimethyl ester (U. Schmidt, A. Lieberknecht, J. Wild, Synthesis 1984, 53–60) sets up the necessary carbon chain. Following protecting group manipulation (vide infra), reduction of the enamino acrylic acids and treatment with condensing agents gives the lactams of both the "cis" and "trans" series in good yields.

In all cases where stereoisomeric mixtures of lactams are formed, they can be easily separated by flash chromatography, and their configuration can be assigned with n.O.e. experiments.

Figure 3:
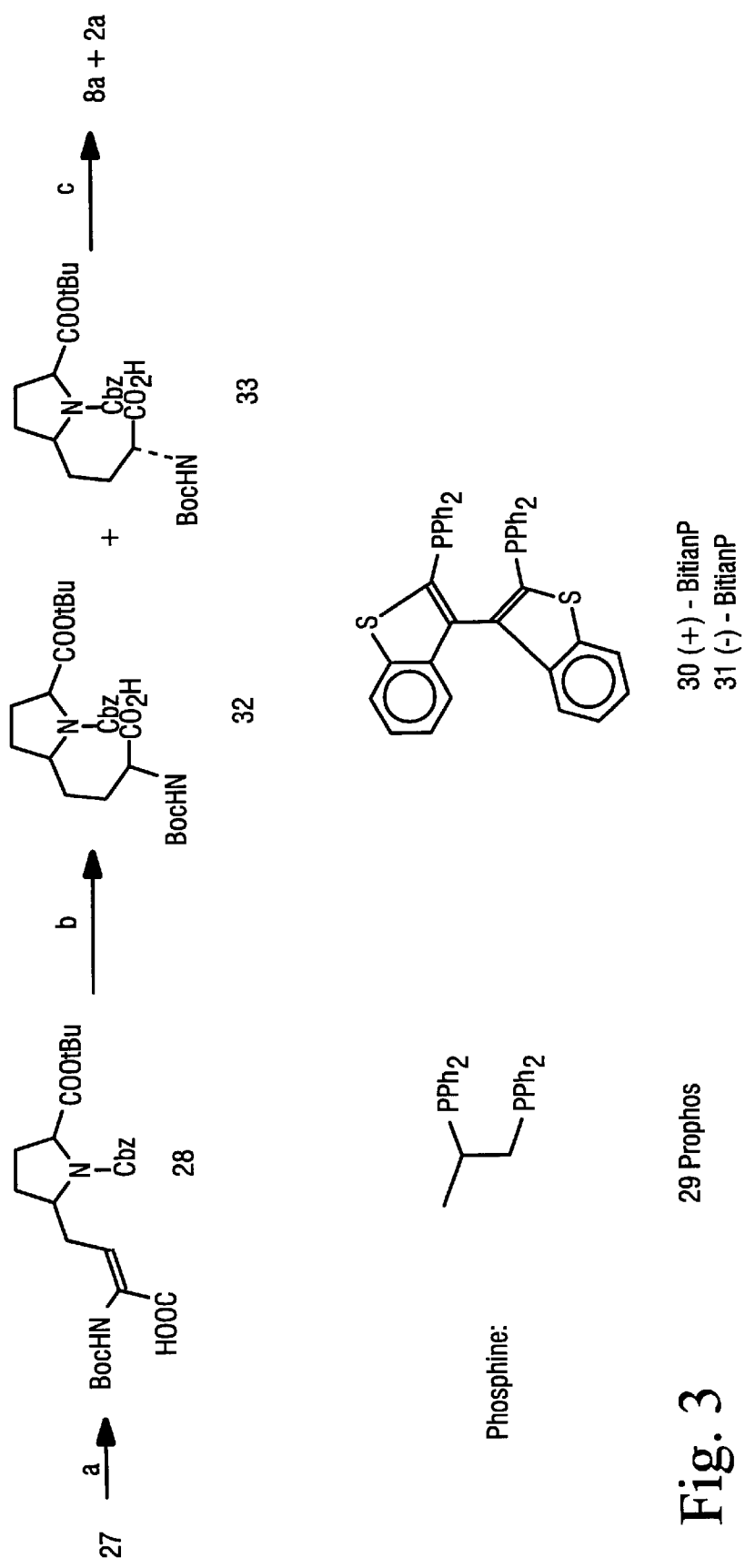
FIG. 3 represents a preferred embodiment of stereoselective hydrogenation with chiral phosphine-Rh catalyst.

The synthetic scheme is best illustrated by the synthesis of the 6,5-fused "cis"-lactams 2a and 8a (FIG. 3). The necessary cis aldehyde 14 is obtained from the known cis 5-allyl-proline derivative 25 (M. V. Chiesa, L. Manzoni, C. Scolastico, Synlett 1996, 441–443) and reacted with the commercially available phosphonate 26 (U. Schmidt, A. Lieberknecht, J. Wild, Synthesis 1984, 53–60) to give 20 to in 98% yield and 7:1 Z:E ratio.

Hydrogenation of 20 occurs initially at the enamino Cbz group, and thus results in a complex mixture of products. To circumvent this problem, the substrate is treated with $Boc_2O$ to give 27 (98%). Reduction of 27 with $H_2$/Pd(OH)$_2$ followed by reflux in MeOH gives a 1:1 mixture of 8a and 2a, which are easily separated by flash-chromatography. From 14 the whole sequence requires only two chromatographic separations (purification of 20 and separation of 8a from 2a) and can easily be carried out in multigram scale.

The stereoselective preparation of the two epimers 8a and 2a (FIG. 3) is carried out using chiral phosphine-Rh catalysed hydrogenation of the enamino acid 28.

Chiral phosphine-Rh catalyst is well-known to represent a powerful and well-established way of access to naturally and non-naturally occurring amino acids and the catalytic asymmetric hydrogenation of dehydropeptides is the logical extension of this methodology to the preparation of biologically active chiral oligo- and polypeptides.

In asymmetric catalytic hydrogenations using chiral phosphine-Rh catalysts (Z) olefins usually gives the highest stereoisomeric purity of the products, but the most stringent requirement for the substrate remains the presence of an acetamido or an equivalent group on the double bond. (K. E. Koenig in Asymmetric Synthesis, J. D. Morrison Editor, Vol 5, Academic Press Inc. 1985, 71) The amide-type carbonyl is needed in order to allow two-point co-ordination of the substrate to the metal, which increases the sterical demand as it has been fully elucidated experimentally. (J.Halpern, ibidem, 41) For applications to the synthesis of peptides protecting groups other than the acetamido, like Boc or Cbz should be used, thus permitting differential deprotection. However, very few examples of asymmetric catalytic hydrogenation are known in which these protecting groups are found on the enamino nitrogen: (B. Basu, S. K. Chattopadhyay, A. Ritzen, T. Frejd, Tetrahedron Asymmetry, 1997, 8, 1841) (S. D. Debenham, J. D. Debenham, M. J. Burk, E. J. Toone, J.Am.Chem.Soc. 1997, 119, 9897) more frequently Boc or Cbz protecting groups are present in different position of dehydropeptides being hydrogenated at the N-terminus. (A. Hammadi et al. Tetrahedron Lett. 1998, 39, 2955—I. Ojima, Pure & Appl. Chem. 1984, 56, 99). For the catalytic asymmetric hydrogenation of 28 [Rh (Phosphine)(COD)]$ClO_4$ catalysts is used. The catalysts were prepared by displacing one cyclooctadiene ligand of [Rh(COD)$_2$]$ClO_4$ with the appropriate phosphine. The ligands investigated are (R)-Prophos 29 and (+) or (−) BitianP 30 and 31. BitianP is a chiral atropisomeric chelating phosphine belonging to a new class of ligands based on biheteroaromatic framework, which gives very high e.e. % in the asymmetric hydrogenation of olefins and ketones. (E. Cesarotti et al. J.Chem.Soc.Chem.Comm. 1995, 685—Cesarotti et al. J.Org.Chem. 1996, 61, 6244).

The results of asymmetric hydrogenation are reported in the Table 1. The conversion is always quantitative but the highest stereodifferentiation is obtained with [Rh/(−)-BitianP] (entry 3). The results suggest that the newly created stereocentre is mainly determined by the catalyst, which overruns the effect of the stereocentre on the substrates (entry 2 and 3). The results also indicate that the Boc protecting group on the enamino nitrogen fulfils the requirements and allows the olefin to chelate to the catalyst.

TABLE 1

Asymmetric hydrogenation of 28

| Entry | Catalyst | 32/33 | d.e. % |
|---|---|---|---|
| 1 | Rh-29 | 86/14 | 72 |
| 2 | Rh-30 | 13/87 | 74 |
| 3 | Rh-31 | 90/10 | 80 |

Reactions were carried out at R.T. for 24 h under 10 atm of $H_2$

Treatment of crude 32 and 33 with $CH_2N_2$, followed by hydrogenation and cyclisation under the usual conditions ($H_2$/Pd—C followed by reflux in MeOH) allows a stereoselective route to lactams 8a and 2a.

Figure 4:
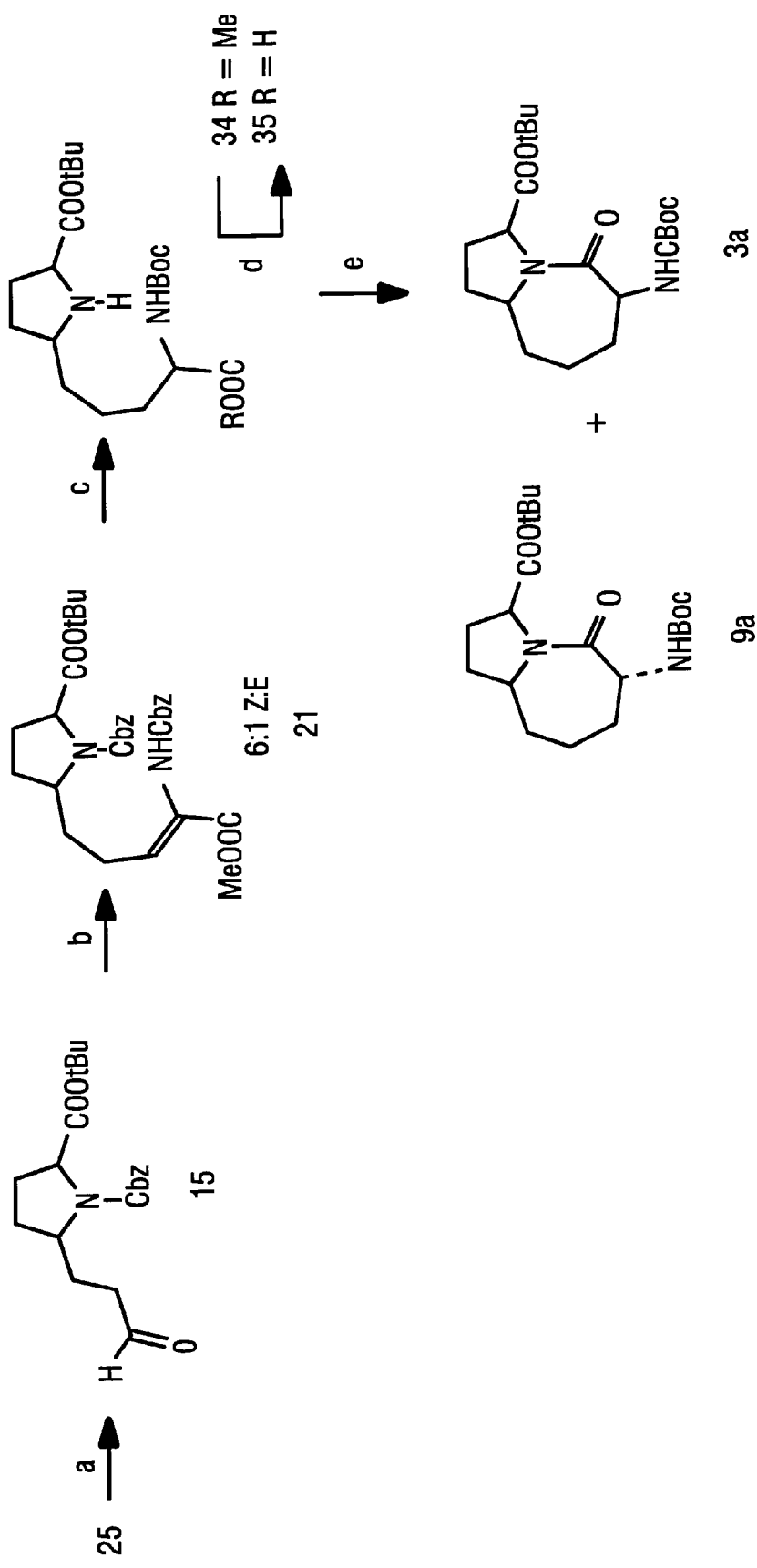
FIG. 4 represents a preferred embodiment of the synthesis of 7,5-fused "cis" lactams.

All the remaining lactams 1–12 can be synthesised following essentially the same sequence described above. Thus, the 7,5-fused lactams 3a and 9a (FIG. 4) can be made starting from the cis aldehyde 15, easily prepared from the cis 5-allyl proline 25. (M. V. Chiesa, L. Manzoni, C. Scolastico, Synlett 1996, 441–443) Horner-Emmons reaction of 15 with 26 gives a 6:1 Z:E mixture of enamino acrylates. After N-protection they are reduced with $H_2$/Pd—C. The thermic cyclisation of methyl ester 34 can be carried out in a suitable solvent, for example xylene. Better results are obtained upon ester hydrolysis followed by EDC/HOBT promoted lactam formation to give 3a and 9a, which are easily separable by flash chromatography (51% overall yield from 25).

Figure 5:
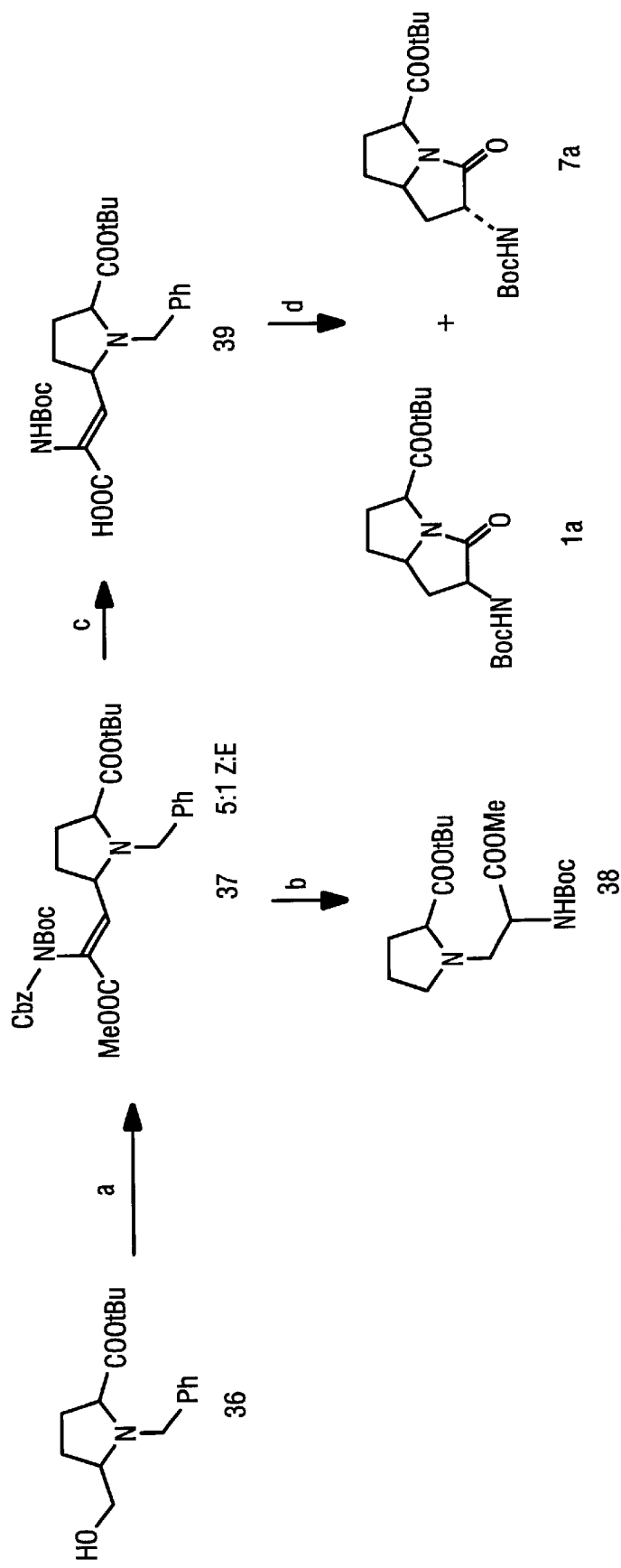
FIG. 5 represents a preferred embodiment of the synthesis of 5,5-fused "cis" lactams.

The starting material for the synthesis of the 5,5-fused "cis" lactams (FIG. 5) is alcohol 36. Oxidation and Horner-Emmons reaction with 26 followed by N-Boc protection gives 37 as a 5:1 Z:E mixture in 57% yield. Hydrogenation of 37 ($H_2$/Pd(OH)$_2$) results in a complex mixture of products, from which the 1,2 diamino ester 38 is anyway isolated in 40% yield. The formation of 38 may result from initial N-debenzylation of 37 followed by intramolecular Michael addition to the enamino ester double bond and hydrogenolysis of the resulting aziridine. The problem can be partly circumvented by performing the hydrogenation starting from the acid 39. Treatment of 39 with $H_2$/Pd—C followed by reflux in MeOH gives an easily separable 1:1 mixture of 1a and 7a in 40% yield.

Figure 6:
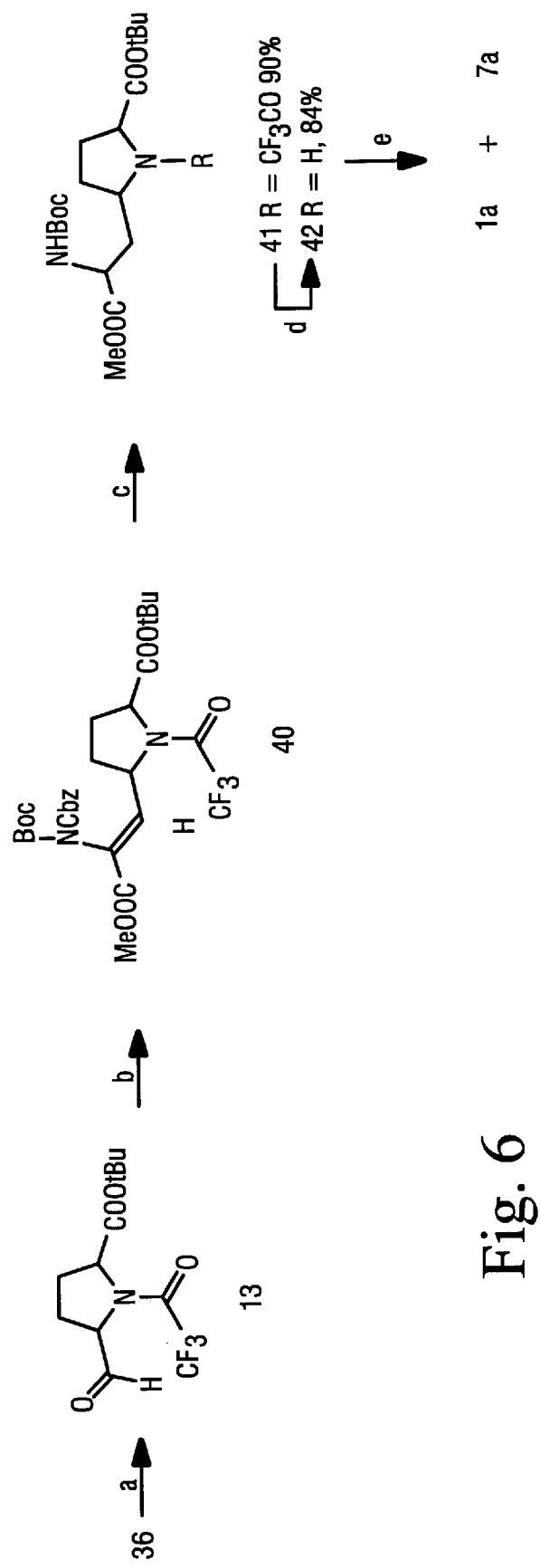
FIG. 6 represents another preferred embodiment of the synthesis of 5,5-fused "cis" lactams.

An alternative synthesis of these lactams is also provided starting from the trifluoroacetamido aldehyde 13 (FIG. 6). Aldehyde 13 is synthesised from 36 with a series of 5 high-yielding to steps. Horner-Emmons and nitrogen protection gives 40 (46% over 7 steps), which could be directly reduced to give a 1:1 mixture of the fully protected ester 41 (77%). Removal of the trifluoroacetamido protecting group ($NaBH_4$ in MeOH, 84%) followed by treatment in refluxing xylene gives the lactams 1a and 7a in 78% yield.

The same synthetic schemes are equally adopted for the synthesis of the "trans" lactam series.

Figure 7:
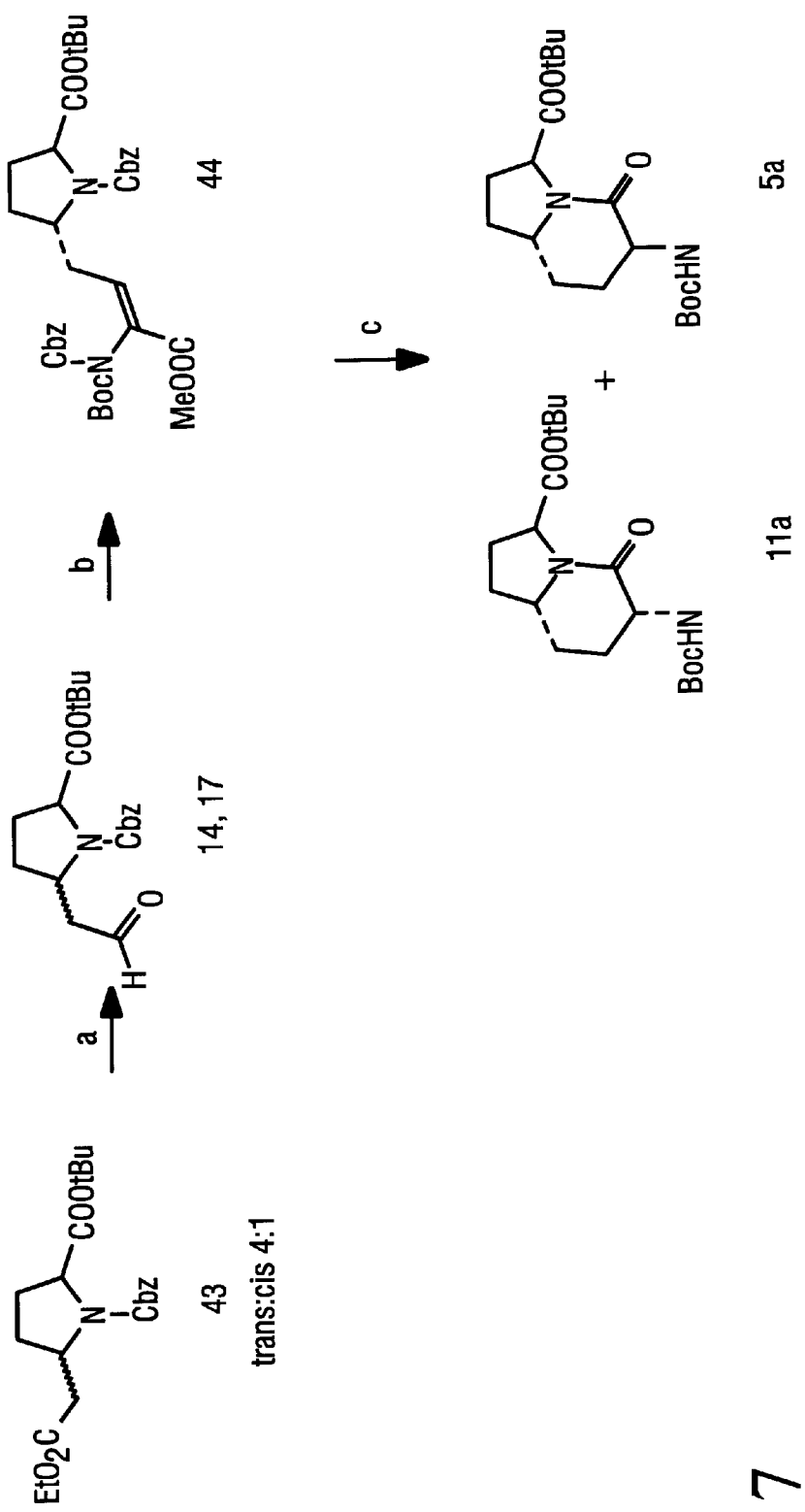
FIG. 7 represents a preferred embodiment of the synthesis of 6,5-fused "trans" lactams.

Starting material for the 6,5-fused "trans" lactams 5a and 11a is the trans-substituted proline 17 (FIG. 7). Aldehyde 17 is best obtained from ester 43, which is made in one step from N-Cbz-5-hydroxy proline tert-Butyl ester as 4:1 trans:cis mixture, following a published procedure. (I. Collado et al., Tetrahedron Lett., 1994, 43, 8037) The Horner-Emmons reaction with the potassium enolate of 26 proceeds with 98% yield. Treatment with $Boc_2O$ and cis/trans isomers separation, followed by unselective $H_2$/Pd—C hydrogenation of the crude and treatment in refluxing MeOH gives a 1:1 mixture of easily separated 5a and 11a.

Figure 8:
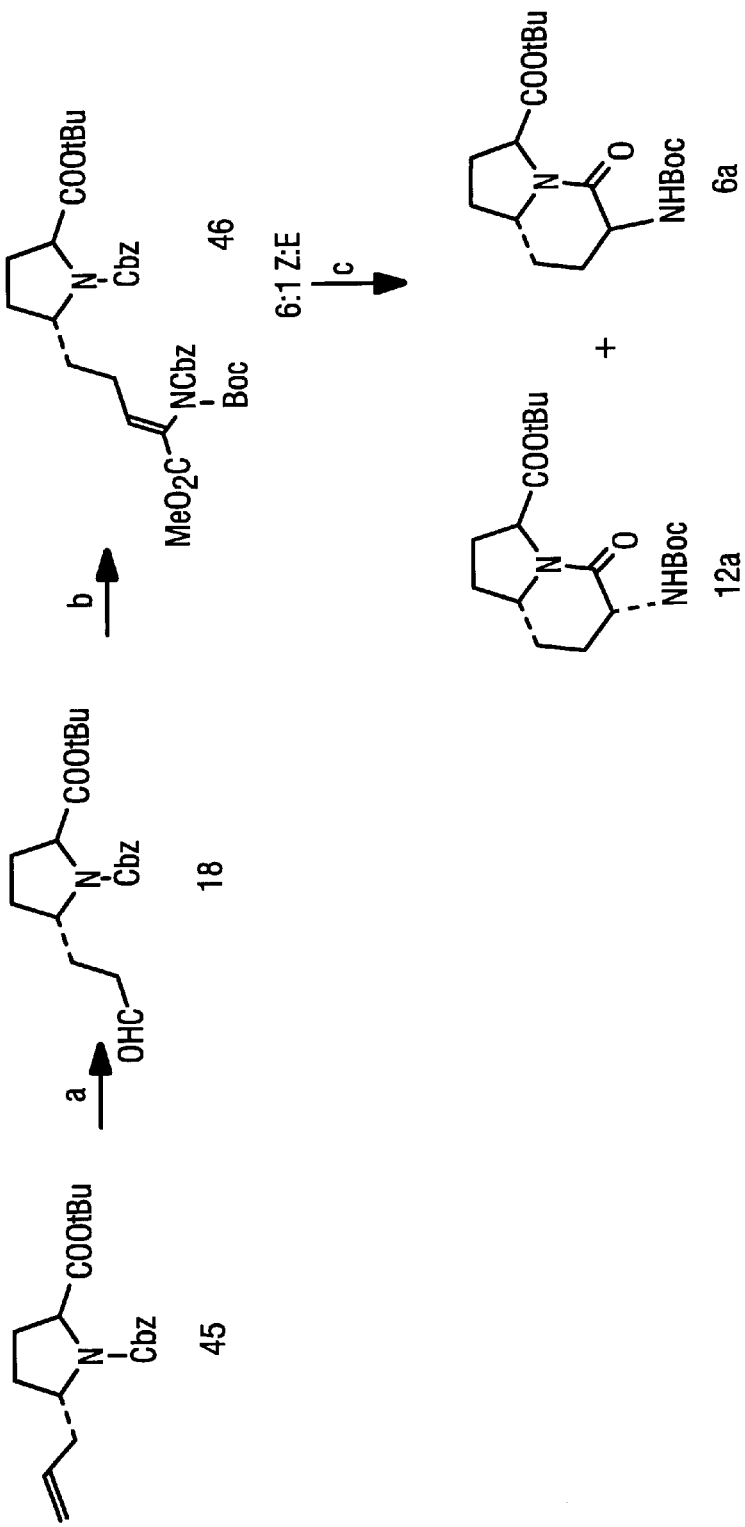
FIG. 8 represents a preferred embodiment of the synthesis of 7,5-fused "trans" lactams.
Figure 9:
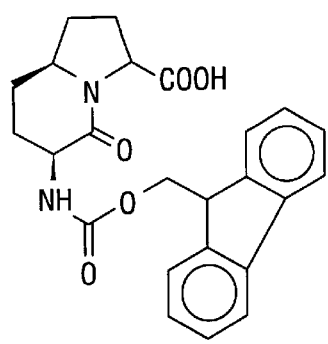
FIG. 9 represents a preferred embodiment of bicyclic lactam templates Fmoc-protected.
Figure 9:
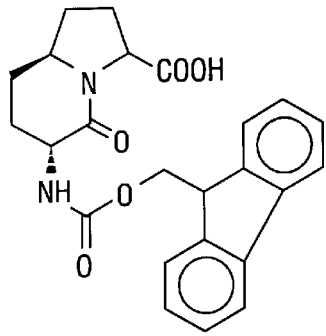
Figure 9:
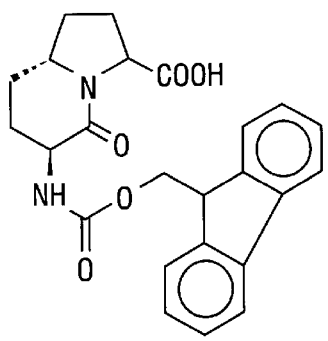
Figure 9:
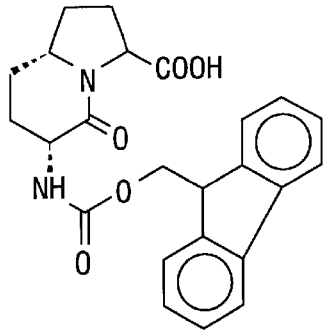
Figure 9:
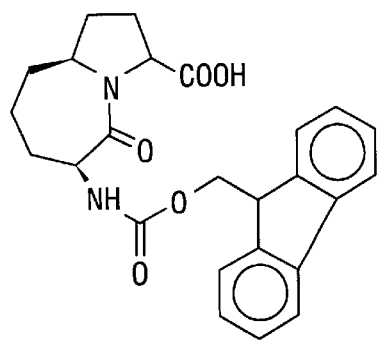
Figure 9:
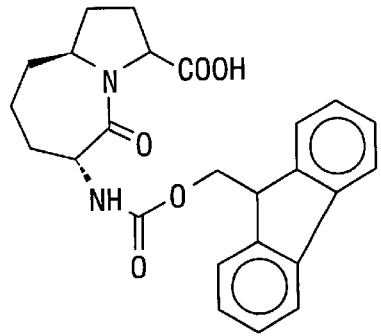
Figure 9:
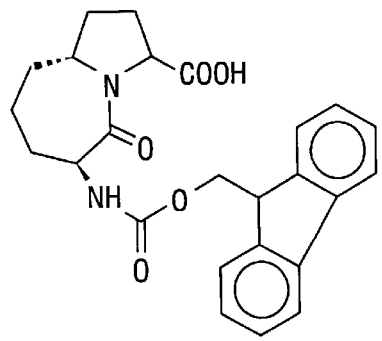
Figure 9:
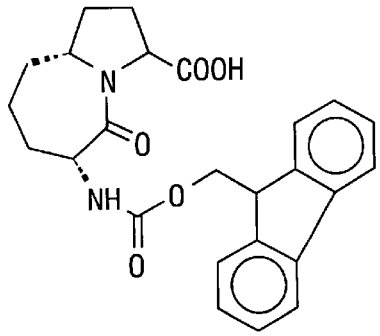
Figure 10:
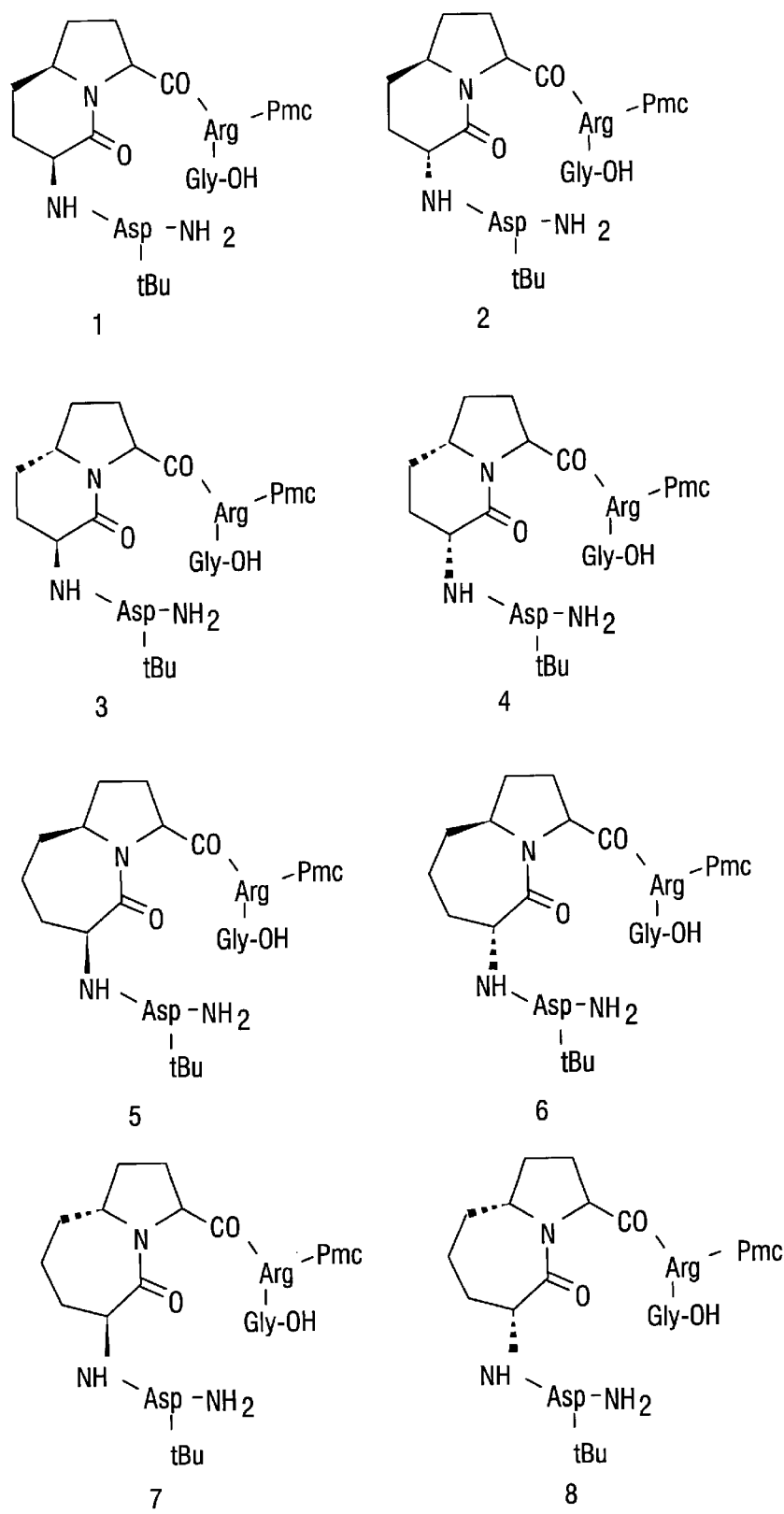
FIG. 10 represents a preferred embodiment of linear pseudopeptides tBu-, Pmc-protected.
Figure 11:
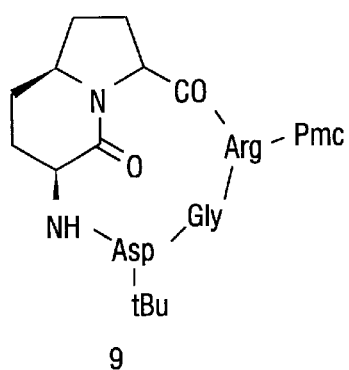
FIG. 11 represents a preferred embodiment of protected cyclic pseudopeptides.
Figure 11:
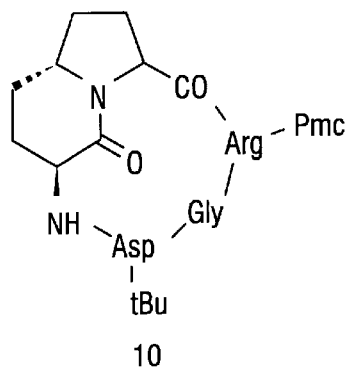
Figure 11:
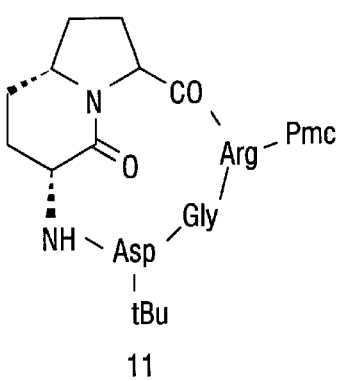
Figure 11:
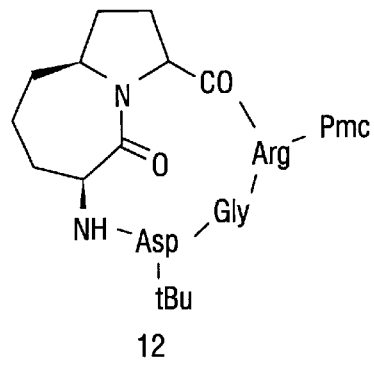
Figure 11:
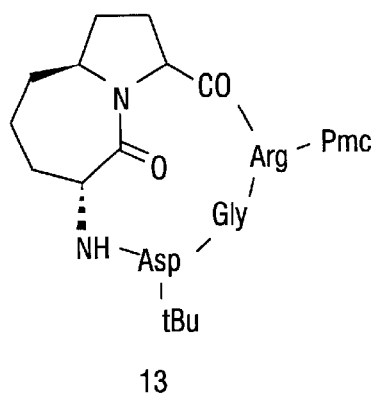
Figure 11:
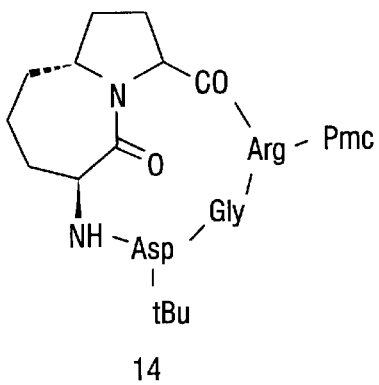
Figure 11:
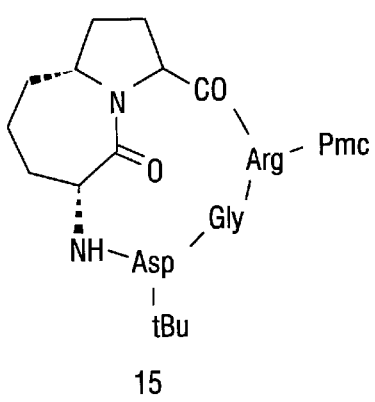
Figure 12:
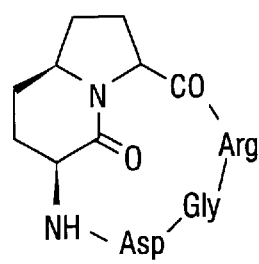
FIG. 12 represents a preferred embodiment of RGD cyclic pseudopeptides.
Figure 12:
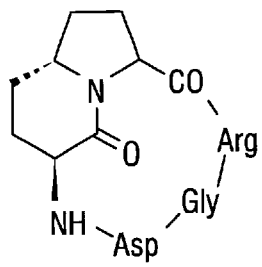
Figure 12:
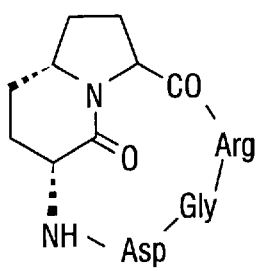
Figure 12:
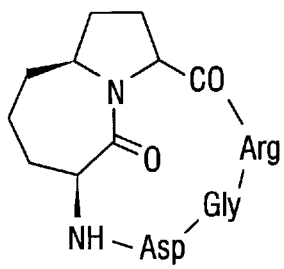
Figure 12:
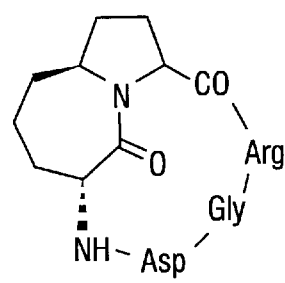
Figure 12:
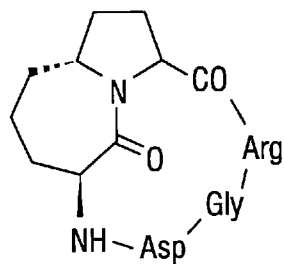
Figure 12:
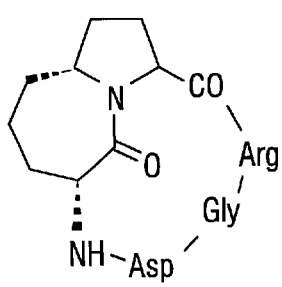

Finally, synthesis of the 7,5-fused "trans" lactams 6a and 12a is achieved starting from the "trans" allyl proline 45 (FIG. 8). (M. V. Chiesa et al. Synlett 1996, 441–443) Hydroboration and Swern oxidation (80% over 2 steps) gives the aldehyde 18, which reacted with 26 to give, after nitrogen protection, 46 as a 6:1 Z:E mixture. The usual sequence (NaOH; $H_2$/Pd—C) allowed the isolation of 6a and 12a in 40% overall yield.

As far as the synthesis of the cyclic RGD portion, synthetic methods are well known in the art. It is convenient to use the solid phase synthesis approach, although other methods could be used.

The classical solid-phase synthesis is preferred.

The solid-phase synthesis is carried out as outlined in C.Gennari et al. Eur.J.Org. Chem. 1999, 379–388.

The protected amino acid is condensed on a suitable resin, for example a Wang-Merrifield resin. Protecting groups are known in this art. 9-fluorenylmethoxycarbonyl (FMOC) is preferred After having activated the resin, N-FMOC-Gly is attached to the Wang-Merrifield resin by means of a suitable condensing agent, preferably diisopropylcarbodiimide (DIC)/1-hydroxybenzotiazole (HOBt)/4-dimethylaminopyridine (DMAP) (J. Org. Chem, 1996, 61, 6735–6738).

Subsequently, N-FMOC-Arg(Pmc)OH is attached, followed by the bicyclic N-FMOC-lactam (IIIa) or (IIIb) and finally N-FMOC-Asp(tBu)OH.

In a still preferred embodiment of the present invention, the solid phase synthesis of cyclic peptides containing the RGD sequence bonded to the bicyclic lactam was performed with 9-flourenylmethoxy carbonyl (Fmoc) strategy. Thus the N-Boc protecting group had to be exchanged by Fmoc group in the bicyclic lactam. The synthesis was performed using Merrifield solid phase peptide synthesis with SASRIN (Super Acid Sensitive Resin) applying Fmoc strategy. Asp was protected at the carboxy group in the side chain as t-butylester and Arg was protected at the guanidino group as Pmc (2,2,5,7,8 Pentamethyl chroman-6 sulphonyl). Linear polipeptides were assembled leaving the glycine residue at the C-terminus to prevent racemization and steric hindrance during the cyclization step. The Fmoc group was cleaved with 20% piperidine in DMF. The Fmoc-protected aminoacid and bicyclic lactams were coupled with HOAT (Azahydroxy Benzotriazole) in the presence of DIC (Diisopropylcarbodiimide) or with HOAT/HATU {Azahydroxy Benzotriazole)/{O-(7-Azabenzotriazol-1-yl)-N, N, N', N'-tetramethyluronioesafluorophosphate} using collidine as base. Peptides were cleaved from SASRIN solid support by 1% TFA in DCM and subsequent neutralisation of TFA with Py. This procedure leads to peptides with intact side chain protective groups. Final cyclization was performed in the same conditions i.e. HOAT/HATU and final deprotection was done with trifluoroacetic acid in the presence of scavengers to avoid side alkylations.

The compounds of the present invention are endowed with interesting physiological properties, which make them useful as medicaments. In particular, the compounds of formula (I) herein disclosed are selective antagonists of $\alpha_v\beta_3$ integrins. This antagonist activity provides the use of said compounds for the preparation of medicaments useful in inhibiting the action of $\alpha_v\beta_3$ integrins. In particular, said medicaments will be used in the treatment of tumors, namely in inhibiting tumor growth and/or angiogenesis or metastasis.

Receptor Binding Assay

By way of example, the tests were performed on the preferred compound ST 1646 (see claim 9) and for comparison purposes, the highly active compound of the prior art, namely c(RGDfV), i.e. cyclo (Arg-Gly-Asp-D-Phe-Val), in the attached report named as the "KESSLER" peptide, disclosed in WO 9706791was used. Both ST 1646 and "KESSLER" are also named "RGD".

Materials And Methods.

The receptor binding assay was performed as described by Orlando and Cheresh (Arginine-Glycine-Aspartic Acid Binding Leading to Molecular Stabilization between Integrin $\alpha_v\beta_3$ and Its Ligand. J. Biol. Chem. 266: 19543–19550, 1991). $\alpha_v\beta_3$ was diluted at 500 ng/ml in coating buffer (20 mM Tris, pH 7.4, 150 mM NaCl, 2 mM $CaCl_2$, 1 mM $MgCl_2$, 1 mM $MnCl_2$) and an aliquot of 100 μl/well was added to a 96-well microtiter plate and incubated overnight at 4° C. The plate was washed once with blocking/binding buffer (50 mM Tris, pH 7.4, 100 mM NaCl, 2 mM $CaCl_2$, 1 mM $MgCl_2$, 1 mM $MnCl_2$, 1% bovine serum albumin), and incubated an additional 2 h at room temperature. The plate was rinsed twice with the same buffer and incubated with radiolabelled ligand at the indicated concentrations. For competition binding, unlabelled competitor and competing peptides were included at the concentration described. After additional three washing, counts were solubilized with boiling 2N NaOH and subjected to γ-counting.

Cell Culture

Bovine microvascular endothelial cells (BMEC) were maintained in DMEM supplemented with 20% foetal calf serum, 50 units/ml heparin, 50 μg/ml bovine brain extract, 100 units/ml gentamycin.

BMEC were cultured on 1% gelatine-coated culture flasks and employed in experiments between passage 6–12.

Human prostate carcinoma cells (PC3) were purchased from American Type Collection Culture (ATCC) and maintained in RPMI supplemented with 10% foetal calf serum, 10 mM L-glutamine, 1% sodium piruvate and 100 units/ml gentamicin.

Murine lung carcinoma cells (M109) were purchased from American Type Collection Culture (ATCC) and maintained in RPMI supplemented with 10% foetal calf serum, 10 mM L-glutamine and 100 units/ ml gentamicin.

Cells were passaged and used for the experiments before reaching confluence.

Adhesion test

Ninety-six-well plates (Falcon) were coated with either fibronectin or vitronectin (both at 5 g/ml in phosphate buffered saline) overnight at 4° C. Cells were detached using EDTA (1 mM)/trypsine (0.25%) and resuspended in own medium described above. Approximately 40,000 cells/100 1 were applied for each well and allowed to adhere for 60 min at 37° C. in presence of different amounts of RGD peptides. For all experiments the non-adherent cells were removed with PBS and the remaining cells were fixed with 4% paraformaldehyde for 10 min.

Cells were stained with 1% toluidine blue for 10 min and rinsed with water.

Stained cells were solubilized with 1% SDS and quantified on a microtiter plate reader at 600 nm.

Experiments described were performed in quadruplicate and repeated a minimum of three times.

Results were presented as mean and standard deviation.

Results

Binding Assay

Both purified and membrane-bound integrin $\alpha_v\beta_3$ bind to the disintegrin echistatin with high affinity, which can be competed efficiently by linear and cyclic RGD peptides (C. C. Kumar, Huimingnie, C. P. Rogers, M. Malkowski, E. Maxwell, J. J. Catino and L. Armstrong. 1997, The Journal of Pharmacology and Experimental Therapeutics; (283) pp 843–853). Therefore to assess the affinity of these peptides for this integrin we used an experimental protocol of competition with the $[^{125}I]$-echistatin as described in materials and methods.

Our results are showing that ST1646 (the compound of claim 9) is the more effective peptide to shift echistatin from its interaction with the $\alpha_v\beta_3$ integrin. Indeed affinity of the RGD peptide ST1646 reported in table 2 as $IC_{50}$ of the binding concentration was almost 20 time higher than the Kessler cyclic peptides used as reference peptide. Therefore these data are providing clear evidence that the structural constrain of the RGD sequence introduced by the ST 1646 result unexpectedly in an affinity for the $\alpha_v\beta_3$ integrin notably higher than Kessler peptide.

TABLE 2

Competition binding of RGD to Integrin $\alpha_v\beta_3$ Receptor

| RGD | $IC_{50}$ ± SD (nM) | Ki ± SD (nM) |
| --- | --- | --- |
| KESSLER RGD | 36.9 ± 6.4 | 34.06 ± 5.9 |
| ST 1646 | 2.2 ± 0.32 | 2.03 ± 0.29 |

Effect of RGD compounds on the binding of [125I] Echistatin to $\alpha_v\beta_3$ integrin.

$IC_{50}$, the concentration of compounds required for 50% inhibition of echistatin binding, were estimated graphically by program Allfit. The Ki of the competing ligands were calculated according to the Cheng and Prusoff equation.

Values are the mean ±standard deviation of triplicate determinations.

Saturation binding isotherms of $^{125}I$-echistatin binding to $\alpha_v\beta_3$ receptor were determined in a solid-phase receptor binding assay as described in materials and method. Integrin $\alpha_v\beta_3$ was coated and incubated with various concentrations (0.05–10 nM) of $^{125}I$-echistatin. Non specific binding was evaluated by carrying out the binding assay in the presence of an excess of cold echistatin and was subtracted from the total binding to calculate specific binding.

In competition binding $^{125}I$-echistatin was added to the wells to a final concentration of 0.05 nM in binding buffer in the presence of competing ligand. Cold unlabelled echistatin and peptides dissolved in binding buffer at concentrations ranging between $10^{-4}$ M to $10^{-9}$.

Endothelial Cells Adhesion Assay

Since transmembrane αβ integrins family are involved in adhesion of endothelial cells to extracellular matrix proteins we assayed adhesion inhibition of bovine microvascular endothelial cells (BMEC) to both vitronectin and fibronectin when these cells were treated with different concentration of our cyclic RGD.

According to the binding experiment the cyclic RGD peptide ST1646 was the more effective in inhibiting adhesion than the other peptide tested. Since vitronectin is a more specific ligand of $\alpha_v\beta_3$ integrin than fibronectin we observed that the RGD tested were able to more efficiently inhibit adhesion of BMEC cells on vitronectin than on fibronectin coated plates (Compare Table 3 with Table 4). Comparing adhesion inhibition, we observed that the cyclic RGD ST1646 was about 10 time more effective than the Kessler peptide inhibiting adhesion of BMEC cells to both fibronectin and vitronectin (see Table 5).

To asses the ability of ST1646 peptide to compete with vitronectin in adhesion assay also on other cells type, we performed this experiment using microvascular endothelial cells (HMEC), human prostate carcinoma cells (PC3) and murine lung carcinoma cells (M109). Table 6 (a, b and c) show a good activity of the ST1646 peptide in inhibiting adhesion of all cells type. Indeed the reported adhesion inhibition of the ST1646 on HMEC, PC3 and M109 cells have shown higher percentage than the Kessler RGD peptide.

Putting together these data we have, therefore, showed high activity of the RGD cyclic peptide ST 1646 on several cellular type coherently with binding affinity experiment previously described.

TABLE 3

Adhesion inhibition of BMEC to Vitronectin

| RGD | % inhibition | t-test versus control |
|---|---|---|
| KESSLER | 96 | P < 0.0001 |
| ST 1646 | 99 | P < 0.0001 |

The percentages of adhesion inhibition refer to 100 M concentration of each peptide of and it's calculated by the following formula (control-sample/control×100) where control was RGD untreated sample. Each percentage is the mean of 4 independent samples treated with the same peptide. The t-test has been calculated, using the Mann Witney non parametric test, by the instat program.

TABLE 4

Adhesion inhibition of BMEC to Fibronectin

| RGD | % inhibition | t-test versus control |
|---|---|---|
| KESSLER | 30 | P < 0.0001 |
| ST 1646 | 60 | P < 0.0001 |

The percentages of adhesion inhibition refer to 100 $\mu$M concentration of each peptide of and it's calculated by the following formula (control-sample/control×100) where control was RGD untreated sample. Each percentage is the mean of 4 independent samples treated with the same peptide. The t-test has been calculated, using the Mann Witney non parametric test, by the instat program.

TABLE 5

$IC_{50}$ of adhesion inhibition of BMEC

| | $IC_{50}$ ($\mu$M) | |
|---|---|---|
| RGD | Fibronectin | Vitronectin |
| KESSLER | >100 | 7.8 ± 1.2 |
| ST 1646 | 44 ± 4 | 0.8 ± 0.06 |

Several concentrations (in quadruplicate) of the indicate RGD peptides ranging between 100 to 0.6 $\mu$M has been tested in adhesion experiment as described in materials and methods. The $IC_{50}$ which represent the RGD peptide concentration able to inhibit 50% of the adhesion of BMEC to the indicate substrate, has been calculate by the linear regression analysis using the Allfit program. The $IC_{50}$ for each RGD has been reported together with the standard deviation.

TABLE 6 (a)

Adhesion assay on Vitronectin

HMEC CELLS

| RGD | % Inhibition | $IC_{50}$ ($\mu$M) | t-test versus control |
|---|---|---|---|
| KESSLER | 39 | 4.23 ± 0.31 | P < 0.01 |
| ST 1646 | 58 | 1.27 ± 0.375 | P < 0.0005 |

Serial concentrations (in quadruplicate) of indicated RGD peptide over a wide range (0.01–100 $\mu$M has been tested in adhesion test, on vitronectin, as described in material and methods.

The $IC_{50}$ represents the average value of 3 experiments and indicates that RGD peptide concentration able to inhibit the 50% of cell adhesion.

The percentages of adhesion inhibition refer to 1.5 $\mu$M concentration of each peptide and were calculated by the following formula (control-sample/control×100) where control was RGD untreated sample.

TABLE 6 (b)

Adhesion assay on Vitronectin

PC3 CELLS

| RGD | % Inhibition | $IC_{50}$ ($\mu$M) | t-test versus control |
|---|---|---|---|
| KESSLER | 69 | 2.5 ± 0.2 | P < 0.0001 |
| ST 1646 | 96 | 0.3 ± 0.08 | P < 0.0001 |

Serial concentrations (in quadruplicate) of indicated RGD peptide over a wide range (0.01–100 $\mu$M has been tested in adhesion test, on vitronectin, as described in material and methods.

The $IC_{50}$ represents the average value of 3 experiments and indicates that RGD peptide concentration able to inhibit the 50% of cell adhesion.

The percentages of adhesion inhibition refer to 1.5 $\mu$M concentration of each peptide and were calculated by the following formula (control-sample/control×100) where control was RGD untreated sample.

TABLE 6 (c)

Adhesion assay on Vitronectin

M109 CELLS

| RGD | % Inhibition | $IC_{50}$ ($\mu$M) | t-test versus control |
|---|---|---|---|
| KESSLER | 70 | 0.46 ± 0.5 | P < 0.0001 |
| ST 1646 | 99 | 0.048 ± 0.06 | P < 0.0001 |

Serial concentrations (in quadruplicate) of indicated RGD peptide over a wide range (0.01–100 $\mu$M has been tested in adhesion test, on vitronectin, as described in material and methods.

The $IC_{50}$ represents the average value of 3 experiments and indicates that RGD peptide concentration able to inhibit the 50% of cell adhesion.

The percentages of adhesion inhibition refer to 1.5 $\mu$M concentration of each peptide and were calculated by the following formula (control-sample/control×100) where control was RGD untreated sample.

The t-test has been calculated using the Mann Witney non parametric test, by the instat program. In the top left side of the two panels it's shown the cell type the adhesion experiment it's referred to.

Antitumor And Antimetastatic Activity Of St 1646 Vs. Kessler Peptide On M109 Lung Carcinoma-Bearing Balb/C Mice Balb/c mice were injected i.m. with M109 lung carcinoma cells ($3 \times 10^5$ cells/mouse) into the hind leg muscle. One day after tumor injection, mice were treated with ST 1646 (300 µg/mouse=15 mg/kg) or Kessler peptide (200 µg/mouse=10 mg/kg) according to a qdx9 treatment schedule (every day for 9 administration, i.p. route).

Tumors were excised at day $10^{th}$ after tumor implant. Mice were sacrificed at day $16^{th}$ from tumor implant and lungs were removed. The number of lung metastases has been evaluated on tumor-excised mice (3 mice/group) using a dissecting microscope.

TVI % (tumor volume inhibition)=100−[(mean tumor weight of treated group/mean tumor weight of control group)×100]. Calculated on day $16^{th}$ after tumor implant (just before mice sacrifice) on nonoperated mice.

The results obtained, reported in table 7, shown that ST1646 is more effective than Kessler peptide in reducing both the number of the metastasis and the volume of the tumor.

TABLE 7

Antitumor and antimetastatic activity of ST 1646 vs. Kessler peptide on M109 lung carcinoma-bearing Balb/c mice.

| Group | Schedule | Mean no. of metastases | TVI % |
|---|---|---|---|
| Untreated | / | 34 | / |
| Kessler 200 µg/mouse (10 mg/kg) | qdx9 | 23 | / |
| ST 1646 300 µg/mouse (15 mg/kg) | qdx9 | 20 | 3 |

Angiogenesis Inhibition On Cam Assay With St1646 Cyclopeptide

Angiogenesis on CAM (chicken embryo chorioallantoic membrane) assay has been quantified by counting the number of vessels interfacing the implanted gelatin sponge on each embryos and calculating the average for each single experimental point (6–8 eggs for peptide concentration). A single treatment means that the embryo received the peptide, at the concentration indicated in the table, only one times at the beginning of the experiment while in the repeated treatment the peptide has been added to the embryo every day for three days. In some experiments we have refereed our sample to control where angiogenesis occurred spontaneously on the chorioallantoic membrane during embryo development (Table 8). In others experiment (Table 9) instead we have used control where angiogenesis has been stimulated by bFGF (400 ng/embryo).

TABLE 8

Angiogenesis inhibition occurred spontaneously on the chorioallantoic membrane

| Treatment | Inhibition (%) | Standard Deviation (%) |
|---|---|---|
| Control | 0 | |
| ST 1646 | −70 | ±27 |

TABLE 8-continued

Angiogenesis inhibition occurred spontaneously on the chorioallantoic membrane

| Treatment | Inhibition (%) | Standard Deviation (%) |
|---|---|---|
| (100 µg single treatment) | | |
| ST 1646 | −27 | ±8 |
| (20 µg repeated treatment) | | |

Inhibition (%)=[(mean vessels treated group−mean vessels control group)/control group]×100

TABLE 9

Angiogenesis inhibition on the chorioallantoic membrane where angiogenesis has been stimulated by bFGF.

| Treatment | Inhibition (%) | Standard Deviation (%) |
|---|---|---|
| Control bFGF (400 ng) | 0 | |
| ST 1646 | −56 | ±18 |
| (100 µg single treatment) | | |
| ST 1646 | −84 | ±30 |
| (100 µg repeated treatment) | | |

Inhibition (%)=[(mean vessels treated group−mean vessels control group)/control group]×100

The results obtained provide a clear evidence that the structural constrain of the RGD sequence introduced by the ST 1646 result unexpectedly in an affinity for the $\alpha_v\beta_3$ integrin notably higher than Kessler peptide. Paralleled to these results in in vitro competition binding assay, ST 1646 assesses its activity in inhibiting the binding of several cell types to fibronectin and vitronectin proteins [table 3-4-5-6(a. b and c)]. According to the binding assay experiments (Table 3), cellular inhibition assay show that ST 1646 is at least 10 folds more active than Kessler peptide. Moreover, ST 1646 is extremely specific in inhibiting cellular binding to vitronectin. This is an additional evidence, in which ST 1646 shows a good selectivity towards cellular $\alpha_v\beta_3$ integrin implicated in binding to vitronectin substrates. In in vivo experiments the results obtained shown that ST 1646 inhibits the growth of M109 lung metastasis (table 7). In addition, ST 1646 strongly inhibits angiogenesis both in FGF-induced and spontaneous angionenesis (table 8 and 9 respectively). This results show that ST 1646 is a very effective antitumoral and antiangiogenic compound.

The compounds of the present invention have azabicycloalkane structure and contain the RGD (Arg-Gly-Asp) sequence are selective inhibitors of αvβ3 receptor, and they are useful agents for treating pathologies due to an altered activation of the αvβ3 receptor. It is well known that the activation of αvβ3 receptor is linked to several pathological processes.

As above mentioned, the experimental results above reported shown that compounds according to the invention are/have: selective inhibitor of αvβ3 receptor; inhibitors of the adhesion of cell lines to fibronectin; antitumoral activity (reduction of the number of the metastasis); antiangiogenetic activity.

As far as the industrial aspects of the present invention are concerned, the compounds of formula (I) shall be suitably formulated in pharmaceutical compositions. Said compositions will comprise at least one compound of formula (I) in admixture with pharmaceutically acceptable vehicles and/or excipients. According to the therapeutic necessity, the bioavailability of the selected compound, its physico-chemical characteristics, the pharmaceutical compositions according to the present invention will be administered by enteral or parenteral route. Enteral pharmaceutical compositions may be both in the liquid or solid from, for example tablets, capsules, pills, powders, sachets, freeze dried powders to be readily dissolved or in any other way soluble powders, solutions, suspensions, emulsions. Parenteral formulation will be in injectable form, as solutions, suspensions, emulsions or in powdery form to be dissolved immediately before use. Other administration routes are also provided for example intranasal, transdermal or subcutaneous implant. Special pharmaceutical compositions can also be provided. For example controlled release formulations or particular vehicles, for example liposomes.

The preparation of the pharmaceutical compositions according to the present invention is absolutely within the general knowledge of the person skilled in this art.

The dosage will be established according to the type of the pathology to be treated, its severity, and the conditions of the patient (weight, age, and sex).

The following examples further illustrate the invention.

Examples 1–12 may be read easier by making reference to FIGS. 1–8 General: $^1$H and $^{13}$C NMR spectra were recorded in CDCl$_3$ or C$_6$D$_6$ as indicated, at 200 (or 300) and 50.3 MHz, respectively. The chemical shift values are given in ppm and the coupling constants in Hz. Optical rotation data were obtained on Perkin-Elmer model 241 polarimeter. Thin-layer chromatography (TLC) is carried out using Merck precoated silica gel F-254 plates. Flash chromatography is carried out with Merck Silica Gel 60, 200–400 mesh. Solvents were dried with standard procedure, and reactions requiring anhydrous conditions were performed under a nitrogen atmosphere. Final product solutions were dried over Na$_2$SO$_4$, filtered and evaporated under reduced pressure on a Buchi rotary evaporator.

EXAMPLE 1
Preparation of Enamides via Horner-Emmons Reaction

General procedure A: To a stirred solution of tBuOK (7.36 mmol) in 40 ml of dry CH$_2$Cl$_2$ under nitrogen atmosphere, at −78° C., was added a solution of Z-α-phosphonoglycine trimethyl ester 26 (7.36 mmol) in 5.0 ml of dry CH$_2$Cl$_2$. The solution was stirred for 30 min at this temperature and then a solution of aldehyde (6.13 mmol) in dry CH$_2$Cl$_2$ (25 ml) was added. After 5 hours the solution was neutralised with a phosphate buffer. The aqueous phase was extracted with CH$_2$Cl$_2$, dried over Na$_2$SO$_4$ and the solvent evaporated under reduced pressure. The crude was purified by flash chromatography (hexane/ethyl acetate), affording the enamide in a Z:E diastereoisomeric mixture.

Preparation of N-Boc-protected Enamide

General procedure B: A solution of enamide (11.0 mmo), (Boc)$_2$O (22.0 mmol) and a catalytic quantity of DMAP in 40 ml of dry THF, was stirred for 30 min. under nitrogen. The solution was then quenched with 40 ml of water and extracted with ethyl acetate. The organic phase was dried over Na$_2$SO$_4$ and the solvent evaporated under reduced pressure. The crude was purified by flash chromatography (hexane/ethyl acetate), yielding the Boc-protected enamide.

Preparation of Alcohol via Hydroboration

General procedure C: To a solution of allyl proline (2.34 mmol) in dry THF (4.2 ml) was added a 0.5 M solution of 9-BBN in THF (1.26 mmol). The reaction was stirred for 12 h. and then cooled at 0° C. and, water (0.6 ml), a 3 N solution of NaOH (0.5 ml) and H$_2$O$_2$ 30% (0.44 ml) were added. The reaction was stirred for 1 h. at room temperature and then refluxed for other 2 h. The aqueous phase was extracted with AcOEt, the collected organic phases were dried over Na$_2$SO$_4$, filtered and evaporated under reduced pressure, the crude was purified by flash chromatography (hexane/ethyl acetate), yielding the alcohol as yellow oil.

Preparation of Aldehyde via Swern Oxidation

General procedure D: To a stirred solution of oxalyl chloride (16.9 mmol) in 35 ml of CH$_2$Cl$_2$, cooled at −60° C., were added DMSO (23.1 mmol), alcohol (5.66 mmol) dissolved in 21 ml of CH$_2$Cl$_2$, TEA (28.2 mmol). The reaction was warmed at room temperature. After one hour the reaction was washed with 50 ml of water and the aqueous phase was extracted with CH$_2$Cl$_2$. The collected organic layers were dried over Na$_2$SO$_4$. The solvent was evaporated under reduced pressure and the crude purified by flash chromatography (hexane/ethyl acetate), yielding the aldehyde.

EXAMPLE 2
Aldehyde (14)

A stirred solution of 25 (6.0 g, 17.4 mmol) in 84 ml of CH$_2$Cl$_2$ was cooled at −60° C. and bubbled with O$_3$ (flow rate=30 1/hour). After 1.5 hours the reaction was allowed to warm to room temperature and bubbled with N$_2$ in order to eliminate the excess of O$_3$. The solution was then cooled at 0° C. with an ice bath and Me$_2$S (101.8 mmol, 38 ml) was added. After 5 days of stirring at room temperature the solvent was evaporated under reduced pressure and the crude was purified by flash chromatography (hexane/ethyl acetate, 8:2), yielding 4.53 g of 14 (75%) as yellow oil.—[α]D$^{22}$=−22.03 (c=1.27, CHCl$_3$).—$^1$H NMR (200 MHz, CDCl$_3$), (signals were splitted for amidic isomerism): δ=1.4–1.5 [2 s, 9 H, C(CH$_3$)$_3$], 1.6–2.4 (m, 4 H, CH$_2$—CH$_2$), 2.4–3.2 (2 m, 2 H, CH$_2$CHO), 4.3–4.5 (m, 2 H, CH$_2$—CH—N, N—CH—COOtBu), 5.15 (s, 2 H, CH$_2$Ph), 7.30 (m, 5 H, aromatic), 9.8 (2 s, 1 H, CHO).—$^{13}$C NMR (50.3 MHz, CDCl$_3$) (signals were splitted for amidic isomerism): δ=200.8, 171.7, 154.0, 136.2, 128.3, 128.0, 127.8, 127.6, 81.4, 67.0, 66.9, 60.8, 60.3, 54.0, 53.2, 49.0, 48.3, 31.0, 30.2, 29.5, 28.9, 28.0, 27.7.—FAB$^+$MS: calcd. for C$_{19}$H$_{25}$NO$_5$ 347.4, found 348.

EXAMPLE 3
Enamide (20)

The general procedure A was followed using 14 and the crude was purified by flash chromatography (hexane/ethyl acetate, 65:35), affording 20 (98%) in a 7:1 Z:E ratio as colourless oils. Z-isomer:—[α]D$^{22}$=+38.78 (c=1.26, CHCl$_3$).—$^1$H NMR (200 MHz, CDCl$_3$) (signals were splitted for amidic isomerism): δ=1.3–1.5 [2 s, 9 H, C(CH$_3$)$_3$], 1.5–2.3 (m, 4 H, CH$_2$—CH$_2$), 2.4–2.7 (2 m, 2 H, =CH—CH$_2$), 3.7 (2 s, 3 H, COOCH$_3$), 4.2 (2 m, 2 H, —CH$_2$—CH—N, N—CH—COOtBu), 5.10 (m, 4 H, CH$_2$Ph), 6.15 (m, 1 H, =CH), 7.30 (m, 10 H, aromatic).—$^{13}$C NMR (50.3 MHz, CDCl$_3$) (signals were splitted for amidic isomerism): δ=172.4, 164.9, 154.5, 136.2, 132.5, 128.3, 128.2, 127.8, 127.7, 127.6, 81.8, 67.2, 66.9, 60.8, 60.3, 57.9, 57.2, 52.1, 33.8, 33.2, 30.7, 29.8, 29.5, 29.0, 28.0, 27.7, 27.6.—FAB$^+$ MS: calcd. for C$_{30}$H$_{36}$N$_2$O$_8$ 552.6, found 553.—E-isomer:—[α]D$^{22}$=−4.08 (c=1.17, CHCl$_3$).—$^1$H NMR (200 MHz, CDCl$_3$) (signals were splitted for amidic isomerism): δ=1.25–1.50 [3 s, 9 H, C(CH$_3$)$_3$], 1.5–2.3 (m, 4 H, CH$_2$—CH$_2$), 2.8–3.3 (2 m, 2 H, =CH—CH$_2$), 3.8 (2 s, 3 H, COOCH$_3$), 4.1 (m, 1 H, —CH$_2$—CH—N), 4.25 (m, 1 H, N—CH—COOtBu), 5.15 (2 s, 4 H, CH$_2$Ph), 6.30 (m, 1 H, =CH), 7.30 (m, 10 H, aromatic).—$^{13}$C NMR (50.3 MHz, CDCl$_3$) (signals were splitted for amidic isomerism): δ=171.8, 164.4, 154.1, 153.6, 136.4, 135.9, 128.7, 128.4, 128.2, 128.1, 128.0, 127.8, 127.7, 127.6, 126.5, 125.9, 81.2, 80.9, 66.7, 61.0, 60.6, 60.2, 58.8, 58.1, 52.2, 32.7, 32.0, 31.8, 29.9, 29.5, 29.2, 28.8, 27.8, 27.7, 22.5, 14.0.

EXAMPLE 4

Enamide (27)

The general procedure B was followed using 20 and the resulting crude was purified by flash chromatography (hexane/ethyl acetate, 7:3), yielding 27 (98%) as yellow oil.—Z-isomer:—[α]D$^{22}$=+16.95 (c=1.86, CHCl$_3$).—$^1$H NMR (200 MHz, CDCl$_3$) (signals were splitted for amidic isomerism): δ=1.3–1.5 [2 s, 18 H, C(CH$_3$)$_3$], 1.6–2.2 (m, 4 H, CH$_2$—CH$_2$), 2.3–2.8 (2 m, 2 H, =CH—CH$_2$), 3.7 (s, 3 H, COOCH$_3$), 4.1–4.2 (2 m, 2 H, =CH—CH$_2$—CH—N, N—CH—COOtBu), 5.15 (m, 4 H, CH$_2$Ph), 6.95 (dd, J=8.5, J=6.4 Hz, 1 H, =CH), 7.30 (m, 10 H, aromatic).—$^{13}$C NMR (50.3 MHz, CDCl$_3$) (signals were splitted for amidic isomerism): δ=171.4, 163.8, 154.6, 154.3, 152.1, 150.4, 139.0, 138.8, 136.2, 135.1, 129.7, 128.3, 128.2, 128.1, 127.8, 127.6, 83.3, 81.2, 77.1, 68.2, 66.8, 60.9, 60.4, 57.5, 56.7, 52.1, 32.8, 32.1, 29.9, 29.1, 28.8, 27.7.—E-isomer:—[α]D$^{22}$=+7.34 (c=1.33, CHCl$_3$).—$^1$H NMR (200 MHz, CDCl$_3$) (signals were splitted for amidic isomerism): δ=1.3–1.5 [2 s, 18 H, C(CH$_3$)$_3$], 1.6–2.2 (m, 4 H, CH$_2$—CH$_2$), 3.0–3.3 (m, 2 H, =CH—CH$_2$), 3.75 (2 s, 3 H, COOCH$_3$), 4,1–4.2 (2 m, 2 H, =CH—CH$_2$—CH—N, N—CH—COOtBu, 5.1–5.2 (m, 4 H, CH$_2$Ph), 6.3 (m, 1 H, =C), 7.30 (m, 10 H, aromatic).—$^{13}$C NMR (50.3 MHz, CDCl$_3$) (signals were splitted for amidic isomerism): δ=171.6, 163.8, 154.5, 154.3, 152.1, 150.4, 142.8, 142.5, 136.3, 135.2, 128.7, 128.3, 128.2, 128.1, 127.9, 127.8, 127.6, 83.2, 81.1, 68.2, 66.8, 61.1, 60.6, 58.1, 57.4, 51.7, 32.7, 32.0, 29.5, 29.4, 28.9, 28.7, 27.7.

EXAMPLE 5

6,5-Fused Bicyclic Lactam (2a, 8a)

A solution of 0.320 g of 27 (0.49 mmol) and a catalytic quantity of Pd/C 10% in 5 ml of MeOH was stirred under H$_2$ for one night. The catalyst was then filtered through celite and the filtration bed was washed with MeOH. The solvent was evaporated under reduced pressure, the residue was dissolved in MeOH and refluxed for 48 h. The solvent was removed and the two diastereoisomers formed were separated by flash chromatography (hexane/ethyl acetate, 7:3), yielding 0.122 g of 8a and 2a (70%) in a 1.4:1 diastereoisomeric ratio as white foam.—[α]D$^{22}$=−10.70 (c=1.29, CHCl$_3$).—$^1$H NMR (200 MHz, CDCl$_3$): δ=1.43–1.45 [2 s, 18 H, C(CH$_3$)$_3$], 1.5–2.5 (m, 8 H, CH$_2$—CH$_2$, BocN—CH—CH$_2$—CH$_2$), 3.69 [m, 1 H, CH—N], 4.1 (m, 1 H, CH—NBoc), 4.38 (dd, J=7.7 Hz, J=1.8 Hz, 1 H, N—CH—COOtBu), 5.59 (d, J=5.4 Hz, 1 H, NH).—$^{13}$C NMR (50.3 MHz, CDCl$_3$): δ=170.7, 165.8, 155.8, 147.1, 81.4, 79.3, 59.0, 56.2, 49.9, 32.0, 29.5, 29.1, 28.2, 27.8, 27.0, 26.5.—FAB$^+$MS: calcd. for C$_{18}$H$_{32}$N$_2$O$_5$ 354.46, found 354.—8a—[α]D$^{22}$=−45.07 (c=1.69, CHCl$_3$).—$^1$H NMR (200 MHz, CDCl$_3$): α=1.44–1.46 [2 s, 18 H, C(CH$_3$)$_3$], 1.55–2.2 (m, 7H, CH$_2$—CH$_2$, BocN—CH—CHH—CH$_2$), 2.5 (m, 1H, BocN—CH—CHH), 3.75 [tt, J=11.2 Hz, J=4.2 Hz, 1 H, CH—N], 3.90 (m, 1 H, CH—NBoc), 4.32 (d, J=9.2 Hz, 1 H, N—CH—COOtBu), 5.59 (broad, 1 H, NH).—$^{13}$C NMR (50.3 MHz, CDCl$_3$): δ=170.6, 167.9, 155.7, 81.2, 79.4, 77.5, 60.4, 59.0, 52.2, 31.4, 28.5, 28.3, 28.2, 27.8, 27.6.—FAB$^+$MS: calcd. for C$_{18}$H$_{32}$N$_2$O$_5$ 354.46, found 354.

Acid (28)

To a solution of 27 (0.640 g, 0.980 mmol) in 4.9 ml of MeOH was added 4.9 ml of 1N NaOH (4.9 mmol). After 18 hours of stirring at room temperature the solvent was evaporated under reduced pressure. The solid residue was dissolved in 5 ml of water and 2N HCl was added until pH 3, then the aqueous solution was extracted with CH$_2$Cl$_2$. The organic phase was dried with Na$_2$SO$_4$, the solvent evaporated under reduced pressure and the crude was purified by flash chromatography (CH$_2$Cl$_2$/MeOH, 95:5), yielding 0.420 g of 28 (85%) as a white solid.

Z isomer:—[α]D$^{22}$=−57.01 (c=1.99, CHCl$_3$).—$^1$H NMR (200 MHz, CDCl$_3$) (signals were splitted for amidic isomerism): δ=1.30– 1.50 [2 s, 18 H, C(CH$_3$)$_3$], 1.7–2.7 (m, 6 H, CH$_2$—CH$_2$, =CH—CH$_2$), 4.2–4.3 (m, 2 H, =CH—CH$_2$—CH—N, N—CH—COOtBu), 5.1 (m, 2 H, CH$_2$Ph), 6.6 (m, 1 H, =CH), 7.30 (m, 6 H, aromatic, NHBoc).—$^{13}$C NMR (50.3 MHz, CDCl$_3$) (signals were splitted for amidic isomerism): δ=171.5, 168.3, 154.8, 154.5, 140.6, 136.4, 136.1, 133.9, 133.5, 128.3, 128.2, 128.1, 127.8, 127.4, 126.9, 81.3, 80.9, 67.1, 66.9, 65.0, 66.9, 65.0, 57.5, 56.8, 33.4, 32.4, 29.5, 28.5, 28.5, 28.0, 27.8, 27.7, 27.4.

E isomer:—[α]D$^{22}$=−41.63 (c=1.87, CHCl$_3$).—$^1$H NMR (200 MHz, CDCl$_3$) (signals were splitted for amidic isomerism): δ=1.35–1.50 [3 S, 18 H, C(CH$_3$)$_3$], 1.7–2.4 (m, 4 H, CH$_2$—CH$_2$), 2.7–3.2 (m, 2 H, =CH—CH$_2$), 4,2–4.3 (m, 2 H, =CH—CH$_2$—CH—N, N—CH—COOtBu), 5.1 (m, 2 H, CH$_2$Ph), 6.7–6.9 (m, 2 H, =CH, NHBoc), 7.30 (m, 5 H, aromatic).—$^{13}$C NMR (50.3 MHz, CDCl$_3$) (signals were splitted for amidic isomerism): δ=171.7, 167.2, 154.9, 154.5, 154.3, 136.5, 136.2, 128.3, 128.2, 127.7, 127.5, 126.9, 126.3, 126.1, 81.2, 80.4, 66.9, 65.0, 60.7, 60.4, 58.3, 57.7, 32.9, 32.0, 29.5, 28.4, 28.1, 27.8, 27.7, 27.4, 27.1, 14.0.

Acid (32, 33)

To the [Rh-(−)-BitianP] catalyst prepared as described in the literature was added 28 (0.16 mmol) and MeOH (30 ml), the resulting solution was stirred for 30 min. A 200 ml stainless-steel autoclave equipped with a magnetic stirrer and a thermostatic bath was pressurised with hydrogen and vented three times. The solution was transferred into the autoclave with a syringe and the autoclave was pressurised at 10 KPa with hydrogen. The solution was stirred for 24 h. at 30° C. The hydrogen pressure was released, the solvent evaporated. The crude was submitted to the next reaction without further purification.

6,5-fused Bicyclic Lactam (2a)

To a solution of 32 and 33 as diastereomeric mixture in MeOH (1.5 ml) was added a solution of CH$_2$N$_2$ in Et$_2$O until the TLC showed that the reaction was complete. The solution was evaporated and the crude was dissolved in MeOH (2 ml) and a catalytic quantity of Pd/C was added, the mixture was stirred under H$_2$ for 12 h. The catalyst was then filtered through celite pad and washed with MeOH. The solvent was evaporated under reduced pressure and the crude, as a white foam, was refluxed in MeOH for 48 h. The solvent was evaporated under reduced pressure and the crude was purified by flash chromatography (hexane/ethyl acetate 7:3) affording 2a (85%) as a white solid.

EXAMPLE 6

6,5-fused Bicyclic Lactam (8a)

This bicyclic lactam was achieved with the same synthetic sequence followed for the lactam 2a using for the asymmetric hydrogenation the [Rh-(+)-BitianP] catalyst.

Aldehyde (15)

The general procedure C was followed using 25 and the resulting residue was purified by flash chromatography (hexane/ethyl acetate, 7:3), yielding the alcohol (95%) as yellow oil.—$^1$H NMR (200 MHz, CDCl$_3$) δ=1.4 [s, 9 H, C(CH$_3$)$_3$], 1.6–2.4 (m, 8 H, CH$_2$—CH$_2$), 3.5–3.8 (2 m, 2 H, CHOH), 4.1 (m, 1 H, CH$_2$—CH—N), 4.25 (m, 1 H, N—CH—COOtBu), 5.15 (s, 2 H, CH$_2$Ph), 7.30 (m, 5 H, aromatic).

The general procedure D was followed using the previous alcohol and the resulting crude residue was purified by flash chromatography (hexane/ethyl acetate, 7:3), yielding 15 (89%) as an oil.—$^1$H NMR (200 MHz, CDCl$_3$), (signals were splitted for amidic isomerism): δ=1.4–1.5 [2 s, 9 H, C(CH$_3$)$_3$], 1.6–2.8 (m, 4 H, CH$_2$—CH$_2$), 4.05 (m, 1 H, CH$_2$—CH—N), 4.25 (m, 1 H, N—CH—COOtBu), 5.15 (s, 2 H, CH$_2$Ph), 7.30 (m, 5 H, aromatic), 9.6–9.8 (2 s, 1 H, CHO).

Aminoester (34)

The general procedure A was followed using 15 and the resulting residue was purified by flash chromatography yielding the enamide (95%) as yellow oil. The compound previously synthesised was submitted to the general procedure B and the resulting residue was purified by flash chromatography yielding the N-Boc protected compound (95%) as white solid. A solution of this compound (0.96 mmol) in MeOH (1 mL) and a catalytic quantity of Pd/C were stirred under hydrogen atmosphere for 12 h. The catalyst was then filtered through a celite pad. The solvent was evaporated under reduced pressure yielding 0.320 g of 34 (83%) as a white solid (mixture of two diastereoisomers).—$^1$H NMR (200 MHz, CDCl$_3$): δ=1.47, 1.48 [2 s, 18 H, C(CH$_3$)$_3$], 1.40–2.1 (m, 10 H, CH$_2$—CH$_2$, BocN—CH—CHH—CH$_2$), 3.00 (m, 1 H, CH—N), 3.6 (m, 1 H, N—CH—COOtBu), 4.3 (m, 1 H, CH—NBoc), 5.05 (db, 1H, NH).

Amino acid (35)

To a solution of 34 (0.288 g, 0.720 mmol) in MeOH was added 1N NaOH, after 1.5 h. the solution was acidified until pH 3 with 1N HCl, then the solution was evaporated. The crude was submitted to the next reaction without further purification.

EXAMPLE 7
7,5-fused Bicyclic Lactams (3a, 9a):

To a solution of the crude 35 (0.720 mmol) in CH$_2$Cl$_2$ (80 ml) was added in the order: Et$_3$N (0.720 mmol, 0.220 ml), HOBt (0.166 g, 1.22 mmol) and a catalytic quantity of DMAP. After 15 min was added EDC (0.180 g, 0.937 mmol) and the solution was stirred for 24 h. To the solution was added H$_2$O (40 ml), the aqueous phase was extracted with CH$_2$Cl$_2$ and the collected organic layers were dried with Na$_2$SO$_4$ filtered and evaporated under reduced pressure affording 0.191 g of 3a and 9a in a 1:1 diastereoisomeric ratio and 72% of yield over 2 steps.

(3a).—$^1$H NMR (200 MHz, CDCl$_3$): δ=1.41, 1.42 [2 s, 18 H, C(CH$_3$)$_3$], 1.5–2.5 (m, 10 H, CH$_2$—CH$_2$), 3.80 (m, 1 H, CH—N), 4.2 (m, 1 H, CH—NBoc), 4.51 (dd, J=4.8 Hz, 1 H, N—CH—COOtBu), 5.54 (db, 1 H, NH).—(9a).—$^1$H NMR (200 MHz, CDCl$_3$): δ=1.42, 1.43 [2 s, 18 H, C(CH$_3$)$_3$], 1.50–2.2 (m, 10H, CH$_2$—CH$_2$), 3.8 [m, 1 H, CH—N], 4.25 (dd, J=4.6 Hz, J=9.6 Hz, 1 H, CH—NBoc), 4.42 (dd, J=2.3 Hz, J=7.2 Hz, 1 H, N—CH—COOtBu), 5.30 (bs, 1 H, NH).

Enamide (37): The general procedure D was followed using 36 and the crude was purified by flash chromatography (hexane/ethyl acetate, 7:3), yielding the aldehyde (81%) as an oil.—$^1$H NMR (200 MHz, CDCl$_3$), (signals were splitted for amidic isomerism): δ=1.48 [s, 9 H, C(CH$_3$)$_3$], 1.8–2.2 (m, 4 H, CH$_2$—CH$_2$), 3.21 (m, 1 H, CH$_2$—CH—N), 3.45 (m, 1 H, N—CH—COOtBu), 3.70 (d, J=12 Hz, 1 H, HCHPh), 4.10 (d, J=12 Hz, 1 H, HCHPh), 7.30 (m, 5 H, aromatic), 9.12 (d, 1 H, CHO).

The general procedure A was followed using the previous aldehyde and the crude was purified by flash chromatography (hexane/ethyl acetate, 65:35), affording the enamide (98%) in a 9:1 Z:E ratio as colourless oils. Z-isomer—$^1$H NMR (200 MHz, CDCl$_3$) δ=1.31 [s, 9 H, C(CH$_3$)$_3$], 1.7–2.2 (m, 4 H, CH$_2$—CH$_2$), 3.3 (m, 1 H, N—CH—COOtBu) 3.5 (s, 1 H, CH$_2$—CH—N), 3.66 (d, J=13.2 Hz, HCHPh) 3.73 (s, 1 H, COOCH$_3$), 3.79 (d 1 H, HCHPh), 5.11 (d, J=12.5 Hz, 1 H, OHCHPh), 5.15 (d, J=12.5 Hz, 1 H, OHCHPh), 6.07 (d, J=7.4 Hz, 1 H, =CH), 7.10–7.6 (m, 10 H, aromatic), 8.15 (sb, 1 H, —NH).—$^{13}$C NMR (50.3 MHz, CDCl$_3$): δ=173.7, 165.1, 154.1, 137.4, 136.1, 129.5, 128.5, 128.3, 128.0, 127.8, 127.7, 127.1, 80.5, 66.9, 65.3, 62.3, 57.5, 52.0, 30.1, 28.9, 27.7.

The general procedure B was followed using the enamide previous synthesised. The crude was purified by flash chromatography (hexane/ethyl acetate, 7:3) yielding 37 (98%) as a white solid.—$^1$H NMR (200 MHz, CDCl$_3$) (signals were splitted for amidic isomerism) δ=1.3–1.5 [2 s, 18 H, C(CH$_3$)$_3$], 1.6–2.2 (m, 4 H, CH$_2$—CH$_2$), 3.1 (m, 1 H, N—CH—COOtBu), 3.5 (m, 1 H, CH$_2$—CH—N), 3.7 (s, 1 H, COOCH$_3$), 3.7 (d, J=12 Hz, 1 H, HCHPh), 3.9 (d, J=12 Hz, 1 H, HCHPh), 5.20 (d, J=12 Hz, 1 H, HCHPh), 7.0 (d, J=8.6 Hz, 1 H, =CH), 7.1–7.4 (m, 10 H, aromatic).

Amino acid (39): To a solution of 37 (0.424 g, 0.713 mmol) in MeOH (4 ml) was added 1N NaOH (4 mmol, 4 ml) and stirred for 1.5 h. The solution was acidified until pH 3 with 1N HCl, then the solution was evaporated. The crude was submitted to the next reaction-with-out further purification.—$^1$H NMR (200 MHz, CDCl$_3$) (signals were splitted for amidic isomerism): δ=1.35, 1.5 [2 s, 18 H, C(CH$_3$)$_3$], 1.7–2.3 (m, 4 H, CH$_2$—CH$_2$), 3.3 (m, 1 H, N—CH—COOtBu), 3.65 (m, 1 H, CH$_2$—CH—N), 3.7 (d, J=12.8 Hz, 1 H, HCHPh), 3.9 (d, J=12.8 Hz, 1 H, HCHPh), 6.5 (d, J=7.6 Hz, 1 H, =CH), 7.1–7.4 (m, 10 H, aromatic), 9.00 (bs, 1 H, —COOH).

EXAMPLE 8
5,5-fused Bicyclic Lactams (1a, 7a)

A solution of 39 (0.713 mmol) and a catalytic quantity of Pd(OH)$_2$/C 20% in 1 ml of MeOH (7 ml) was stirred under hydrogen atmosphere for 12 h. The catalyst was then filtered through a celite pad and the solvent was evaporated under reduced procedure. The crude was dissolved in MeOH and refluxed for 48 h. The solvent was evaporated under reduced pressure and the crude was purified by flash chromatography (hexane/ethyl acetate 6:4) affording 0.097 g of 1a and 7a as a white solid in 40% of yield (over 2 steps) and 1:1 diastereomeric ratio. 1a:—[α]$_D^{22}$=-4.80 (c=1.20, CHCl$_3$).—$^1$H NMR (200 MHz, CDCl$_3$): δ1.50, 1.51 [2 s, 18 H, C(CH$_3$)$_3$], 1.6–2.4 (m, 5 H, CH$_2$—CH$_2$, BocN—CH—CHH), 2.95 (m, 1 H, BocN—CH—CHH), 3.85 [m, 1 H, (CH—N], 4.15 (d, J=8.8 Hz, 1 H, N—CH—COOtBu), 4.60 (m 1 H, CH—NBoc), 5.25 (broad, 1 H, NH).—$^{13}$C NMR (50.3 MHz, CDCl$_3$) (signals were splitted for amidic isomerism): δ=171.7, 169.7, 155.6, 81.8, 79.5, 58.8, 56.5, 56.0, 55.8, 39.5, 33.4, 29.5, 28.2, 27.8.—FAB$^+$MS: calcd. for C$_{17}$H$_{28}$N$_2$O$_5$ 340.41, found 341.— 2a: [α]$_D^{22}$=-4.80 (c=1.20, CHCl$_3$).—$^1$H NMR (200 MHz, CDCl$_3$): δ=1.45 [2 s, 18 H, C(CH$_3$)$_3$], 1.5–2.5 (m, 6 H, CH$_2$—CH$_2$, BocN—CH—CH$_2$), 4.05 (d, J=8.8 Hz, 1 H, N—CH—COOtBu), 4.12 (m, 1 H, CH—N), 4.25 (m, 1 H, CH—NBoc), 5.05 (broad, 1 H, NH).—$^{13}$C NMR (50.3 MHz, CDCl$_3$) (signals were splitted for amidic isomerism): δ=170.9, 169.8, 155.2, 82.2, 81.8, 79.9, 77.1, 61.2, 58.8, 57.6, 56.0, 55.8, 34.4, 33.8, 33.4, 29.9, 29.5, 29.2, 28.5, 28.1, 27.7.—FAB$^+$MS: calcd. for C$_{17}$H$_{28}$N$_2$O$_5$ 340.41, found 341.

Aldehyde (13)

To a stirred solution of 36 (1.5 g, 5.14 mmol) in 39 ml of dry CH$_2$Cl$_2$ under nitrogen were added in the order: TBDMSCl (0.931 g, 6.17 mmol), TEA (6.17 mmol, 0.94 ml) and DMAP (0.063 g, 0.51 mmol). After 12 h. the solvent was evaporated under reduced pressure and the crude purified by flash chromatography (hexane/ethyl acetate, 9:1), yielding 1.910 g of compound (94%) as a colourless oil.—[α]$_D^{22}$=−3.61 (c=2.52, CHCl$_3$).—$^1$H NMR (200 MHz, CDCl$_3$): δ=−0.5 (s, 6 H,CH$_3$Si), 0.85 [s, 9 H, (CH$_3$)$_3$C—Si], 1.4 [s, 9 H, C(CH$_3$)$_3$], 1.5–2.1 (m, 4 H, CH$_2$—CH$_2$), 2.9 (m, 1 H, SiO—CH$_2$—CH—N), 3.3–3.4 (m, 3 H, N—CH—COOtBu, SiO—CH$_2$), 3.9 (s, 2 H, CH$_2$Ph), 7.3 (m, 5 H, aromatic).—$^{13}$C NMR (50.3 MHz, CDCl$_3$): δ=173.6, 139.3, 129.1, 127.9, 126.7, 19.9, 67.5, 66.8, 65.8, 58.8, 28.4, 28.0, 27.8, 25.8, 18.1, −3.6.

A solution of the silyl protected alcohol (1.850 g, 4.55 mmol) and Pd(OH)$_2$/C 20% (0.250 g, 0.45 mmol) in 45 ml of MeOH was stirred under hydrogen atmosphere for 4 hours. Then the catalyst was filtered through celite pad and washed with MeOH, the solvent was evaporated under reduced pressure, yielding 1.34 g of hydrogenated compound (94%) as colourless oil.—[α]$_D^{22}$=−5.80 (c=1.99, CHCl$_3$).—$^1$H NMR (200 MHz, CDCl$_3$): δ=0.4 (s, 6 H, CH$_3$Si), 0.92 [s, 9 H, (CH$_3$)$_3$C—Si], 1.49 [s, 9 H, C(CH$_3$)$_3$], 1.5–2.1 (m, 4 H, CH$_2$—CH$_2$), 2.35 (broad, 1 H, NH), 3.2 (m, 1 H, SiO—CH$_2$—CH—N), 3.65 (m, 3 H, N—CH—COOtBu, SiO—CH$_2$).

To a stirred solution of the previous compound (1.2 g, 3.79 mmol) in 38 ml of CH$_2$Cl$_2$ were added pyridine (11.39 mmol, 0.92 ml) and (CF$_3$CO)$_2$O (8.35 mmol, 1.16 ml). After 1.5 hours the solvent was evaporated under reduced pressure and the crude purified by flash chromatography (hexane/ethyl acetate, 9:1), yielding 1.4 g of the N-protected pyrrolidine (89%) as colourless oil.—[α]$_D^{22}$=−8.62 (c=2.11, CHCl$_3$).—$^1$H NMR (200 MHz, CDCl$_3$): δ=0.4 (s, 6 H,CH$_3$Si), 0.9 [s, 9 H, (CH$_3$)$_3$C—Si], 1.47 [s, 9 H, C(CH$_3$)$_3$], 1.7–2.4 (m, 4 H, CH$_2$—CH$_2$), 3.5 (m, 1 H, SiO—CHH), 3.75 (dd, J=10.6 Hz, J=4.2 Hz, 1 H, SiO—CHH), 4.2 (m, 1 H, SiO—CH$_2$—CH—N), 4.35 (t, J=8.5 Hz 1 H, N—CH—COOtBu).

To a stirred solution of N-protected pyrrolidine (1.2 g, 2.91 mmol) in 29 ml of THF, cooled at −40° C., was added a 1M solution of TBAF in THF (3.20 mmol, 3.2 ml). Then the solution was allowed to warm at room temp. After 2.5 hours was added 30 ml of brine and the resulting mixture was extracted with ethyl acetate. The organic phase was dried with Na$_2$SO$_4$ and the solvent evaporated under reduced pressure. The crude was purified by flash chromatography (hexane/ethyl acetate, 6:4), yielding 0.850 g of O-deprotected compound (98%) as colourless oil.—[α]$_D^{22}$=−6.40 (c=1.45, CHCl$_3$).—$^1$H NMR (200 MHz, CDCl$_3$): δ=1.5 [s, 9 H, C(CH$_3$)$_3$], 2.0–2.4 (m, 4 H, CH$_2$—CH$_2$), 3.4–3.7 (m, 2 H, HO—CH$_2$), 4.2–4.6 (m, 3 H, N—CH—COOtBu, HO—CH$_2$—CH—N).

The general procedure D was followed using the alcohol and the residue was purified by flash chromatography (hexane/ethyl acetate, 6:4), yielding the aldehyde (93%) as white solid.—[α]$_D^{22}$=+22.48 (c=1.53, CHCl$_3$).—$^1$H NMR (200 MHz, CDCl$_3$): δ=1.5 [s, 9 H, C(CH$_3$)$_3$], 1.8–2.5 (m, 4 H, CH$_2$—CH$_2$), 4.5–4.7 (m, 2 H, CHO—CH—N, N—CH—COOtBu), 9.7 (s, 1 H, CHO).

Enamide (40)

The general procedure A was followed using 13 and the crude residue was purified by flash chromatography affording the enamide (68%) as colourless oil (diastereoisomeric ratio Z:E=1:1).—$^1$H NMR (200 MHz, CDCl$_3$) (signals were splitted for amidic isomerism and were referred to the mixture of two diastereoisomers): δ=1.5 [s, 9 H, C(CH$_3$)$_3$], 1.6–2.45 (m, 4 H, CH$_2$—CH$_2$), 3.75 (s, 3 H, COOCH$_3$), 4.6 to (m, 1 H, N—CH—COOtBu), 4.8 (dd, J=18 Hz, J=10 Hz, 1 H, =CH—CH—N), 5.12 (s, 2 H, CH$_2$Ph), 6.3, 6.8 (2d, J=10 Hz, 1 H, =CH of Z-isomer, E-isomer), 7.35 (m, 5 H, aromatic).

The general procedure B was followed using the enamide and the crude was purified by flash chromatography affording 40 with a 95% of yield as colourless oil.—$^1$H NMR (200 MHz, C$_6$D$_6$) (signals were splitted for amidic isomerism and were referred to the mixture of two diastereoisomers): δ=1.3, 1.5 [2 s, 18 H, C(CH$_3$)$_3$], 1.6–2.35 (m, 4 H, CH$_2$—CH$_2$), 3.7 (s, 3 H, COOCH$_3$), 4.6–4.8 (m, 2 H, N—CH—COOtBu, =CH—CH—N), 5.25 (m, 2 H, CH$_2$Ph), 7.0 (m, 1 H, =CH), 7.35 (m, 5 H, aromatic).—$^{13}$C NMR (50.3 MHz, C$_6$D$_6$) (signals were splitted for amidic isomerism and were referred to the mixture of two diastereoisomers): δ=169.1, 163.9, 141.2, 136.1, 129.9, 128.4, 128.2, 127.4, 119.4, 113.7, 83.6, 82.5, 82.0, 68.8, 68.5, 68.2, 62.5, 60.9, 60.8, 58.5, 57.6, 56.8, 53.2, 51.9, 51.7, 51.6, 33.7, 31.8, 30.2, 27.7, 27.5, 26.9.

Aminoester (41)

A Z/E mixture of 40 (0.609 g, 1.01 mmol) and Pd(OH)$_2$/C 20% (0.054 g) in 10 ml of MeOH was stirred under hydrogen atmosphere for 18 h. The catalyst was filtered through a celite pad and washed with MeOH. The solvent was evaporated under reduced pressure and the crude purified by flash chromatography (toluene/Et$_2$O, 85:15), yielding 0.365 g of 40 (77%) as yellow oil.—$^1$H NMR (200 to MHz, CDCl$_3$) (signals were splitted for amidic isomerism and were referred to the mixture of two diastereoisomers): δ=1.45 [s, 18 H, C(CH$_3$)$_3$], 1.6–2.7 (m, 6 H, CH$_2$—CH$_2$, BocN—CH—CH$_2$), 3.75 (2 s, 3 H, COOCH$_3$), 4.25–4.4 (2 m, 2 H, BocN—CH, BocN—CH—CH$_2$—CH), 4.55 (m, 1 H, N—CH—COOtBu), 5.30 (d, J=8.5 Hz, 1 NH).—$^{13}$C NMR (50.3 MHz, CDCl$_3$) (signals were splitted for amidic isomerism and were referred to the mixture of two diastereoisomers): δ=172.4, 170.0, 155.8, 128.9, 128.0, 82.7, 82.0, 79.7, 61.4, 60.6, 58.0, 56.5, 52.2, 51.5, 37.7, 36.4, 35.5, 30.2, 29.7, 29.0, 28.4, 28.1, 27.6, 25.5. —FAB$^+$MS: calcd. for C$_{20}$H$_{31}$F$_3$N$_2$O$_7$ 468.47, found 468.

Amino acid (42)

A solution of 41 (0.184 g, 0.393 mmol) and NaBH$_4$ (0.0298 g, 0.781 mmol) in 8 ml of MeOH was stirred for 1 hour at room temperature. The solution was concentrated and 10 ml of water was added. The aqueous solution was extracted with ethyl acetate, the collected organic phases were dried on Na$_2$SO$_4$ and the solvent evaporated under reduced pressure. The two diastereoisomers formed in the previous reactions were separated at this step by flash chromatography (ethyl acetate/hexane, 6:4), achieving 0.123 g of 42 (R) and 42 (S) (84%) in a 2.6:1 diastereoisomeric ratio as colourless oil.—42 (R):—$^1$H NMR (200 MHz, C$_6$D$_6$) (signals were splitted for amidic isomerism): δ=1.30, 1.45 [2 s, 18 H, C(CH$_3$)$_3$], 1.5–1.9 (m, 6 H, CH$_2$—CH$_2$, BocN—CH—CH$_2$), 2.85 (m, 1 H, BocN—CH—CH$_2$—CH), 3.2–3.4 (m, 4 H, COOCH$_3$, N—CH—COOtBu), 4.65 (m, 1 H, BocN—CH), 6.6 (broad, 1 H, NHBoc).—$^{13}$C NMR (50.3 MHz, C$_6$D$_6$) (signals were splitted for amidic isomerism): δ=174.1, 173.2, 155.8, 81.4, 81.3, 79.5, 60.6, 60.4, 56.5, 56.3, 52.5, 52.0, 37.7, 31.9, 30.0, 29.8, 28.2, 28.0, 27.9.—FAB$^+$MS: calcd. for C$_{18}$H$_{32}$N$_2$O$_6$ 372.46, found 373.— 42 (S):—$^1$H NMR (200 MHz, C$_6$D$_6$) (signals were splitted for amidic isomerism): δ=1.30, 1.50 [2 s, 18 H, C(CH$_3$)$_3$], 1.50–1.80 (m, 6 H, CH$_2$—CH$_2$, BocN—CH—CH$_2$), 2.8 (m, 1 H, BocN—CH—CH$_2$—CH), 3.3 (s, 3 H, COOCH$_3$), 3.4 (dd, J=9.1 Hz, J=5.9 Hz, 1 H, N—CH—COOtBu), 4.45 (m, 1 H, BocN—CH), 5.3 (broad, 1 H, NHBoc).—$^{13}$C NMR (50.3 MHz, C$_6$D$_6$) (signals were splitted for amidic isomerism): δ=171.7, 171.5, 164.2, 164.0, 154.7, 154.3, 153.5, 136.6, 136.4, 135.8, 128.4, 128.3, 128.2, 128.1, 127.7, 126.2, 125.9, 125.8, 81.0, 87.1, 66.8, 66.6, 60.8, 60.4, 58.2, 57.5, 52.3, 52.2, 32.8, 31.9, 28.5, 28.1, 27.8, 27.7, 27.4, 27.1.—FAB+MS: calcd. for $C_{18}H_{32}N_2O_6$ 372.46, found 373.

EXAMPLE 9
5,5-Fused Bicyclic Lactam [1a]

A stirred solution of 42 (S) (0.028 g, 0.075 mmol) in 1.5 ml of p-xylene was warmed at 130° C. for 24 hours. The solvent was then evaporated under reduced pressure and the crude purified by flash chromatography (hexane/ethyl acetate, 7:3), yielding 19 mg of 1a (74%) as a white foam.—$\alpha_D^{22}$=−4.80 (c=1.20, CHCl₃).—¹H NMR (200 MHz, CDCl₃): δ=1.50, 1.51 [2 s, 18 H, C(CH₃)₃], 1.6–2.4 (m, 5 H, CH₂—CH₂, BocN—CH—CHH), 2.95 (m, 1 H, BocN—CH—CHH), 3.85 [m, 1 H, (CH—N], 4.15 (d, J=8.8 Hz, 1 H, N—CH—COOtBu), 4.60 (m 1 H, CH—NBoc), 5.25 (broad, 1 H, NH).—¹³C NMR (50.3 MHz, CDCl₃) (signals were splitted for amidic isomerism): δ=171.7, 169.7, 155.6, 81.8, 79.5, 58.8, 56.5, 56.0, 55.8, 39.5, 33.4, 29.5, 28.2, 27.8.—FAB+MS: calcd. for $C_{17}H_{28}N_2O_5$ 340.41, found 341.

EXAMPLE 10
5,5-Fused Bicyclic Lactam [7a]

The compound [7a] was achieved from compound 42 (R), by using the same procedure described for the synthesis of compound 1a, with a 65% of yield as white foam.—$[\alpha]_D^{22}$=−4.80 (c=1.20, CHCl₃).—¹H NMR (200 MHz, CDCl₃): δ=1.45 [2 s, 18 H, C(CH₃)₃], 1.5–2.5 (m, 6 H, CH₂—CH₂, BocN—CH—CH₂), 4.05 (d, J=8.8 Hz, 1 H, N—CH—COOtBu), 4.12 (m, 1 H, CH—N), 4.25 (m, 1 H, CH—NBoc), 5.05 (broad, 1 H, NH).—¹³C NMR (50.3 MHz, CDCl₃) (signals were splitted for amidic isomerism): δ=170.9, 169.8, 155.2, 82.2, 81.8, 79.9, 77.1, 61.2, 58.8, 57.6, 56.0, 55.8, 34.4, 33.8, 33.4, 29.9, 29.5, 29.2, 28.5, 28.1, 27.7.—FAB+MS: calcd. for $C_{17}H_{28}N_2O_5$ 340.41, found 341.

Ester (43)

To a stirred suspension of KH (0.777 g, 19.4 mmol) in anhydrous DMF (80 ml) the triethyl phosphonoacetate (19.4 mmol, 3.9 ml) was added. The mixture was stirred at room temperature for 1 h and then a solution of hemiaminal (5.2 g, 16.2 mmol) in DMF (80 ml) was added. The reaction was stirred overnight at room temperature, quenched with satured aqueous NH₄Cl solution and extracted with AcOEt. The combined organic extract were dried over Na₂SO₄ and the solvent was evaporated to dryness and purified by flash chromatography yielding 4.8 g of 43 (75%) in a 4:1 trans:cis diastereoisomeric ratio.—¹H NMR (200 MHz, CDCl₃) (signals are splitted for amidic isomerism): δ=1.2–1.35 (m, 3 H, CH₃CH₂O), 1.35, 1.40, 1.45, 1.50 [4 s, 9 H, C(CH₃)₃], 1.60–2.60 (m, 5 H, CH₂—CH₂, CHCO₂Et), 2.70–3.1 (2 dd, J₁=4 Hz, J₂=15 Hz, 1 H, CHCO₂Et, trans isomer), 3.2–3.5 (2 dd, J₁=4 Hz, J₂=15 Hz, 1 H, CHCO₂Et, cis isomer), 4.13 (dq, J₁=J₂=7 Hz , 2 H, CH₃CH₂O) 4.27 (m, 1 H, CHCO₂tBu), 4.45 (m, 1 H, CH₂—CH—N), 5.15–5.35 (m, 2 H, CH₂Ph), 7.3–7.4 (m, 5 H, aromatic).—¹³C NMR (50.3 MHz, CDCl₃) (signals are splitted for amidic isomerism): δ=171.4, 171.3, 171.1, 171.0, 154.4, 154.1, 153.8, 136.5, 136.3, 128.3, 128.2, 127.7, 127.6, 81.2, 66.9, 66.8, 60.8, 60.5, 60.3, 60.2, 55.5, 55.2, 54.5, 39.1, 38.0, 30.4, 29.7, 28.9, 28.7, 28.2, 28.0, 27.8, 27.7, 27.1, 14.1.—FAB+MS: calcd. for $C_{21}H_{29}NO_6$ 391.2, found 392.

Aldehyde (14, 17)

To a stirred solution of 43 (1.205 g, 3.08 mmol) in dry diethylether (31 mL) at −10° C., LiBH₄ 2M in THF (1.5 mL, 3.08 mmol) was added. After 24 h a saturated solution of NaHCO₃ (40 ml) was added and the resulting mixture was extracted with AcOEt. The organic phase was dried over Na₂SO₄ and evaporated to dryness. The crude product was purified by flash chromatography (hexane/ethyl acetate 1:1), yielding 1.01 g of alcohol (94%) as a yellow oil.—Trans-isomer: $[\alpha]_D^{22}$=−32.3 (c=1.02, CHCl₃).—¹H NMR (200 MHz, CDCl₃): δ=1.35 [s, 9 H, C(CH₃)₃], 1.5–2.4 (m, 6 H, CH₂—CH₂, CH₂—CH₂—O), 3.5–3.7 (m, 2 H, CHOH), 3.82 (bs, 1 H, OH), 4.22 (dd, J=7.5, J~0, 1 H, CHCO₂tBu), 4.38 (m, 1 H, CH₂—CH—N), 5.15 (m, 2 H, CH₂Ph), 7.32 (s, 5 H, aromatic).—¹³C NMR (50.3 MHz, CDCl₃) (signals were splitted for amidic isomerism): δ=171.4, 156.1, 136.0, 128.4, 128.3, 127.9, 127.8, 127.7, 81.2, 81.1, 67.2, 67.0, 60.4, 59.9, 59.0, 55.2, 55.1, 38.6, 37.7, 28.9, 28.7, 27.8, 27.7.—Cis-isomer: $[\alpha]_D^{22}$=−54.0 (c=1.51, CHCl₃).—¹H NMR (200 MHz, CDCl₃): δ=1.33 [s, 9 H, C(CH₃)₃], 1.4–1.24 (m, 6 H, CH₂—CH₂, CH₂—CH₂—O), 3.6–3.9 (m, 2 H, CH₂OH), 4.08 (dd, J=9.5, J=4, 1 H, OH), 4.25 (dd, J=J 8.5, 1 H, CHCO₂tBu), 4.40 (m, 1 H, CH₂—CH—N), 5.15 (m, 2 H, CH₂Ph), 7.35 (s, 5 H, aromatic).—¹³C NMR (50.3 MHz, CDCl₃): δ=27.7, 28.9, 30.4, 37.4, 55.4, 58.8, 60.5, 67.4, 81.3, 127.7, 127.9, 128.3, 136.1, 155.9, 171.8.

A solution of the alcohol (0.304 g, 0.87 mmol) in dry CH₂Cl₂ (2.5 mL) was added to a suspension of Dess-Martin periodinane (0.408 g, 1.13 mmol) in dry CH₂Cl₂ (2.5 mL) at room temperature. After 1 h Et₂O and NaOH 1N were added till clear solution. The aqueous phase was extracted twice with Et₂O; the collected organic layers were washed with H₂O, dried with Na₂SO₄, and evaporated to dryness. The crude product was purified by flash chromatography (hexane/ethyl acetate 7:3) affording 0.277 g of 17 (92%).—Trans-isomer: $[\alpha]_D^{22}$=−48.65 (c=1.01, CHCl₃).—¹H NMR (200 MHz, CDCl₃) (signals were splitted for amidic isomerism): δ=1.35–1.45 [2 s, 9 H, C(CH₃)₃], 1.6–2.6 (m, 4 H, CH₂—CH₂), 2.8–3.1 (2 m, 2 H, CH₂CHO), 4.3 (m, 1 H, CHO—CH₂—CH—N), 4.6 (m, 1 H, N—CH—COOR), 5.15 (m, 2 H, CH₂Ph), 7.30 (m, 5 H, aromatic), 9.1, 9.3 (2 m, 1H, CHO).—¹³C NMR (50.3 MHz, CDCl₃) (signals were splitted for amidic isomerism): δ=200.3, 171.4, 154.1, 136.2, 128.4, 128.2, 128.0, 127.8, 127.7, 81.3, 67.1, 66.9, 60.5, 60.1, 53.4, 52.5, 49.0, 48.4, 29.5, 28.6, 28.3, 27.8, 27.7, 27.3.

N-Boc-protected enamide (44): The mixture of aldehydes 14 and 17 was reacted following the general procedure A. The crude product was purified by flash chromatography (hexane/ethyl acetate 7:3), affording the enamide in 99% yield, as a trans:cis, Z/E mixture. Trans-Z-isomer : $[\alpha]_D^{22}$=−61.84 (c=1.01, CHCl₃).—¹H NMR (200 MHz, CDCl₃) (signals were splitted for amidic isomerism) : δ=1.35–1.50 [2 s, 9 H, C(CH₃)₃], 1.6–2.3 (m, 4 H, CH₂—CH₂), 2.3–2.8 (2 m, 2 H, =CH—CH₂), 3.75 (s, 3 H, COOCH₃), 4,15–4.25 (2 m, 2 H, —CH₂—CH—N and N—CH—COOtBu), 5.15 (m, 4 H, CH₂Ph), 6.55 (t, J=8.5 Hz, 1 H, =C), 7.35 (m, 10 H, aromatic).—¹³C NMR (50.3 MHz, CDCl₃) (signals were splitted for amidic isomerism): δ=171.4, 164.8, 164.6, 154.4, 153.9, 153.7, 136.4, 136.2, 135.9, 135.7, 133.0, 132.0, 128.4, 128.3, 128.2, 128.1, 128.0, 127.9, 127.8, 127.6, 126.7, 81.2, 67.3, 67.2, 67.0, 66.8, 60.6, 60.2, 57.6, 56.7, 52.3, 33.5, 32.5, 28.5, 27.7, 27.4.—FAB+MS: calcd. for $C_{30}H_{36}N_2O_8$ 552.6, found 552.

Trans-E-isomer: $[\alpha]_D^{22}$=−50.16 (c=1.48, CHCl₃).—¹H NMR (200 MHz, CDCl₃) (signals were splitted for amidic isomerism): δ=1.35–1.45 [2 s, 9 H, C(CH₃)₃] 1.6–2.4 (m, 4 H, CH₂—CH₂), 2.7–3.1 (2 m, 2 H, =CH—CH₂), 3.8 (2 s, 3 H, COOCH₃), 4,1–4.3 (2 m, 2 H, —CH₂—CH—N e N—CH—COOtBu), 5.10 (m, 4 H, CH₂Ph), 6.50 (m, 1 H, =CH), 7.25 (m, 10 H, aromatic).—¹³C NMR (50.3 MHz, CDCl₃) (signals were splitted for amidic isomerism): δ=171.7, 171.5, 164.2, 164.0, 154.7, 154.3, 153.5, 136.6, 136.4, 135.8, 128.4, 128.3, 128.2, 128.1, 127.7, 126.2, 125.9, 125.8, 81.0, 87.1, 66.8, 66.6, 60.8, 60.4, 58.2, 57.3, 52.2, 32.8, 31.9, 28.5, 28.1, 27.8, 27.7, 27.4, 27.1.

The mixture of enamides (0.394 g, 0.71 mmol) was reacted following the general procedure B. Flash chromatography of the crude product (hexane/ethyl acetate 75:25) afforded 0.287 g (73%) of pure trans-isomer 23.—Z-isomer: $[\alpha]_D^{22}$=−50.98 (c=1.56, CHCl$_3$).—$^1$H NMR (200 MHz, CDCl$_3$) (signals were splitted for amidic isomerism): δ=1.3–1.5 [4 s, 18 H, C(CH$_3$)$_3$], 1.7–2.6 (m, 6 H, CH$_2$—CH$_2$ and =CH—CH$_2$), 3.7 (s, 3 H, COOCH$_3$), 4,1–4.3 (m, 2 H, —CH$_2$—CH—N and N—CH—COOtBu), 5.15 (m, 4 H, CH$_2$Ph), 6.8 (m, 1 H, =CH), 7.30 (m, 10 H, aromatic).—$^{13}$C NMR (50.3 MHz, CDCl$_3$) (signals were splitted for amidic isomerism): δ=171.4, 163.9, 154.6, 154.5, 150.0, 146.2, 138.5, 138.0, 136.2, 129.9, 128.3, 128.2, 128.1, 127.8, 83.4, 81.2, 68.3, 67.0, 66.8, 60.6, 60.2, 56.9, 56.2, 52.2, 32.9, 32.0, 28.3, 27.8, 27.7, 27.3.—FAB+MS: calcd. for C$_{35}$H$_{44}$N$_2$O$_{10}$ 652.7, found 652.

E-isomer: $^1$H NMR (200 MHz, CDCl$_3$): δ=1.3–1.4 [2 s, 18 H, C(CH$_3$)$_3$], 1.5–2.3 (m, 4 H, CH$_2$—CH$_2$), 3.0 (2 m, 2 H, =CH—CH$_2$), 3.65 (2 s, 3 H, COOCH$_3$), 4,2 (m, 2 H, —CH$_2$—CH—N and N—CH—COOtBu), 5.15 (m, 4 H, CH$_2$Ph), 6.1 (2 t, J=8.5 Hz, 1 H, =CH), 7.30 (m, 10 H, aromatic).—$^{13}$C NMR (50.3 MHz, CDCl$_3$): δ=171.5, 163.7, 154.6, 154.3, 152.2, 150.4, 142.7, 142.2, 136.3, 135.1, 128.9, 128.3, 128.2, 128.0, 127.8, 127.7, 83.4, 83.3, 81.1, 77.1, 68.3, 66.9, 66.7, 60.7, 60.3, 57.6, 56.8, 51.7, 32.9, 32.0, 28.4, 28.0, 27.7, 27.3, 27.0.

EXAMPLE 11
6,5 Fused Bicyclic Lactams (5a, 11a)

A solution of 44 (0.489 g, 0.75 mmol) and Pd(OH)$_2$/C 20% (catalytic) in MeOH (7.5 mL) was stirred under H$_2$ for one night. The catalyst was filtered off and the mixture was refluxed for 24 h. The solvent was then removed and the two diastereoisomeric products were separated by flash chromatography (hexane/ethyl acetate 6:4), yielding 0.186 g of 5a and 11a (70%) in a 1.4:1 diastereoisomeric ratio.—5a: $^1$H NMR (200 MHz, CDCl$_3$): δ=1.45–1.50 [2 s, 18 H, C(CH$_3$)$_3$], 1.55–2.60 (m, 8 H, CH$_2$—CH$_2$ and BocN—CH$_2$—CH$_2$), 3.68 [tt, J=14.9 Hz and 4.2 Hz, 1 H, (R)$_2$CH—N], 4.05 (m, 1 H, CH—NBoc), 4.35 (t, J=8.5 Hz, 1H, N—CH—COOtBu), 5.28 (broad, 1 H, NH).—FAB+MS: calcd. for C$_{18}$H$_{32}$N$_2$)$_5$ 354.46, found 354.

11a: $[\alpha]_D^{22}$=−107.9 (c=1.7, CHCl$_3$).—$^1$H NMR (200 MHz, CDCl$_3$): δ=1.45–1.50 [2 s, 18 H, C(CH$_3$)$_3$], 1.75–2.50 (m, 8 H, CH$_2$—CH$_2$ and BocN—CH—CH$_2$—CH$_2$), 3.70 [m, 1 H, CH—N], 4.15 (m, 1 H, CH—NBoc), 4.50 (t, J=7.0 Hz, 1H, N—CH—COOtBu), 5.55 (broad, 1 H, NH).—$^{13}$C NMR (50.3 MHz, CDCl$_3$): δ=170.6, 168.5, 155.5, 81.4, 79.3, 59.0, 56.2, 49.9, 32.3, 28.1, 27.8, 26.5, 25.9.—FAB+MS: calcd. for C$_{18}$H$_{32}$N$_2$O$_5$ 354.46, found 354.

Aldehyde (18)

The general procedure C was followed using 43 and the crude residue was purified by flash chromatography affording the alcohol with a yield of 98%.—$^1$H NMR (200 MHz, CDCl$_3$) δ=1.32 [s, 9 H, C(CH$_3$)$_3$], 1.4–2.4 (m, 8 H, CH$_2$—CH$_2$), 3.5–3.7 (m, 2 H, CH$_2$OH), 4.1 (m, 1 H, CH$_2$—CH—N), 4.24 (m, 1 H, N—CH—COOtBu), 5.05 (s, 2 H, CH$_2$Ph), 7.25 (m, 5 H, aromatic).

The general procedure D was followed using the alcohol and the crude was purified by flash chromatography (hexane/ethyl acetate 6:4) affording 18 with a yield of 82%—$^1$H NMR (200 MHz, CDCl$_3$), (signals were splitted for amidic isomerism): δ=1.32, 1.45 [2 s, 9 H, C(CH$_3$)$_3$], 1.5–2.7 (m, 8 H, CH$_2$—CH$_2$), 4.1 (m, 1 H, CH$_2$—CH—N), 4.25 (m, 1 H, N—CH—COOR), 5.15 (s, 2 H, CH$_2$Ph), 7.20–7.40 (m, 5 H, aromatic), 9.6–9.8 (2 m, 1 H, CHO).

Enamide (46)

The general procedure A was followed using 18 and the crude was purified by flash chromatography (hexane/ethyl acetate 6:4) affording the enamide with a yield of 90% (diastereomeric ratio Z/E=7:1)—$^1$H NMR (200 MHz, CDCl$_3$), (signals were splitted for amidic isomerism): δ=1.32, 1.42 [s, 9 H, C(CH$_3$)$_3$], 1.5–2.7 (m, 8 H, CH$_2$—CH$_2$), 3.71 (s, 1 H, COOCH$_3$), 4.1 (m, 1 H, CH$_2$—CH—N), 4.22 (m, 1 H, N—CH—COOtBu), 5.0–5.20 (m, 4 H, CH$_2$Ph), 6.6 (m, 1 H, =CH), 7.20–7.45 (m, 10 H, aromatic).

The general procedure B was followed using the enamide and the crude residue was purified by flash chromatography yielding 46 (98%).—$^1$H NMR (200 MHz, CDCl$_3$), (signals were splitted for amidic isomerism): δ=1.32, 1.42 [2 s, 18 H, C(CH$_3$)$_3$], 1.5–2.2 (m, 8 H, CH$_2$—CH$_2$), 3.71 (s, 1 H, COOCH$_3$), 3.9 (m, 1 H, CH$_2$—CH—N), 4.22 (m, 1 H, N—CH—COOtBu), 5.0–5.20 (m, 4 H, CH$_2$Ph), 6.9 (m, 1 H, =CH), 7.20–7.45 (m, 10 H, aromatic).—$^{13}$C NMR (50.3 MHz, CDCl$_3$) (signals were splitted for amidic isomerism): δ=141.6, 128.4, 128.2, 128.1, 127.8, 127.7, 68.2, 66.8, 60.5, 58.1, 52.1, 31.3, 29.5, 27.1, 27.3, 24.6.

EXAMPLE 12
trans-7,5-fused Bicyclic Lactam (6a, 12a)

To a solution of 46 (0.093 g, 0.141 mmol) in MeOH (2 ml) was added 1N NaOH (0.705 mmol, 0.705 ml) and stirred for 1.5 h. The solution was acidified until pH 3 with 1N HCl, then the solution was evaporated. The crude was submitted to the next reaction without further purification.—$^1$H NMR (200 MHz, CDCl$_3$) (signals were splitted for amidic isomerism): δ=1.25, 1.48 [2 s, 18 H, C(CH$_3$)$_3$], 1.5–2.4 (m, 8 H, CH$_2$—CH$_2$), 4.1 (m, 1 H, CH$_2$—CH—N), 4.3 (m, 1 H, N—CH—COOtBu), 5.12 (s, 2 H, CH$_2$Ph), 6.65 (m, 1 H, =CH), 7.1–7.4 (m, 5 H, aromatic), 9.00 (bs, 1 H, —COOH).

A solution of previous compound in xylene was refluxed for 48 h. The solvent was evaporated and the crude was purified by flash chromatography yielding 6a and 12a with a 40% of yield.

6a—$^1$H NMR (200 MHz, CDCl$_3$) (signals were splitted for amidic isomerism): δ=1.43, 1.45 [2 s, 18 H, C(CH$_3$)$_3$], 1.51–2.40 (m, 10 H, CH$_2$—CH$_2$), 3.75 [m, 1 H, CH—N], 4.22 (m, 1 H, CH—NBoc), 4.48 (t, J=17 Hz, 1H, N—CH—COOtBu), 5.7 (broad, 1 H, NH).

12a—$^1$H NMR (200 MHz, CDCl$_3$) (signals were splitted for amidic isomerism): δ=1.47, 1.48 [2 s, 18 H, C(CH$_3$)$_3$], 1.55–2.50 (m, 8 H, CH$_2$—CH$_2$), 4.0 (m, 1 H, CH—N), 4.30 (m, 1 H, CH—NBoc), 4.50 (dd, J=5.4 Hz, J=17 Hz, 1H, N—CH—COOtBu), 6.0 (bd, 1 H, NH).

EXAMPLE 13

Using the bicyclic lactams prepared according to the preceding examples, the respective peptidomimetics compounds, containing the RGD sequence were prepared according to the method disclosed in Gennari et al.: Eur. J. Org. Chem., 1999, 379–388.

Examples 14–47 may be read easier by making reference to FIGS. 9–12.

EXAMPLE 14

Reagents and solvents: Sasrin resin (200–400 mesh, 1.02 mmol/g) was purchased from Bachem. All the solvents used for the solid-phase synthesis were of HPLC quality or Analyticai Reagent grade and were dried over molecular sieves before use. Flash chromatography: silica gel (Kieselgel 60, 230–400 mesh). TLC: silica plates (60 F$_{254}$, 0.25 mm, Merck). NMR: Bruker AC-200, AC-300 and Avance-400 (200 MHz, 300 MHz and 400 MHz for $^1$H, 50.3 MHz, 75.4 MHz and 100.5 MHz for $^{13}$C). Optical rotations: Perkin Elmer 241 polarimeter. Mass spectrometry: VG 7070 EQ-HF and PE-SCIEX API-100. Elemental analysis: Perkin Elmer 240. All solid-phase reaction were carried out on a wrist shaker.

Abbreviations: DCM: dichloromethane, DIC: N,N'-diisopropylcarbodiimide, HOAt 1-hydroxy-7-azabenzotriazole, HOBt: 1-hydroxybenzotriazole, HATU: 0-(7-azabenzotriazol-1-yl)-N,N,N',N'-tetramethyluronium hexafluorophosphate, TNBS: 2,4,6-trinitrobenzenesulfonic acid.

TNBS test was performed following this procedure: a few resin beads were sampled and washed several times with ethanol. The sample was then placed in a vial and 1 drop of a 10% solution of DEPEA in DMF and 1 drop of 1% 2,4,6-trinitrobenzenesulfonic acid (TNBS) in DMF were added. The sample was then observed and colour changes were noted. The TNBS test is considered to be positive (presence of free amino groups) when the resin beads turn orange or red within 1 min and negative (no free amino groups) when the beads remain colourless.

General Procedure 1. Preparation of N-Fmoc-Temp-OH (Temp-1–8). To a solution of the starting N-Boc-Temp-OtBu (0.62 mmol) in dichloromethane (4.8 ml) was added, under $N_2$, trifluoroacetic acid (4.8 ml) and the resulting mixture was stirred at room temperature for 1 h. The solvents were then evaporated under reduced pressure, the crude residue was dissolved in THF (0.32 ml) and 10% $Na_2CO_3$ (0.77 ml) was added. After 15 min the solution was cooled to 0° C., a solution of Fmoc-ONSu (95 mg) in THF (1.4 ml) was added and the resulting mixture was stirred at room temperature for 3 h (TLC $CHCl_3$/MeOH/AcOH 75:25:5). THF was then evaporated under reduced pressure, the aqueous phase was washed with AcOEt, conc. HCl was added to pH 3–4 and the solution extracted with AcOEt (3×5 ml). The combined organic layers were dried with $Na_2SO4$ and evaporated under reduced pressure to afford the crude product as a white fbam, which was used without further purification.

EXAMPLE 15

(3S,6S,9S)-1-aza-9-carboxy-3-(9'-fluorenylmethoxycarbonyl amino)-2-oxo-bicyclo [4.3.0]nonane (Temp1)

Was prepared in quantitative overall yield following general procedure 1. $^1$H NMR (200 MHz, $C_6D_6$, 3 23° K.) δ=1.1–2.0 (m, 8 H, 4 $CH_2$), 2.9 (m, 1 H, CH—N), 4.12 (dd, $J_1=J_2$=6.5 Hz, 1 H, CH—CHO), 4.20–4.50 (m, 4 H, CH—NHFmoc, $CHCO_2$H, $CH_2$O) 6.30 (d, J=7 Hz, 1 H, NH), 7.10–7.30 (m, 4 H, aromatic), 7.45–7.65 (m, 4 H, aromatic), 11.2 (bs, 1 H, $CO_2$H).

$^{13}$C NMR (50.3 MHz, CDC13) δ=26.5, 26.9, 28.8, 31.9, 47.0, 50.2, 56.9, 58.5, 67.1, 119.8, 125.2, 127.1, 127.6, 141.2, 143.7, 143.9, 156.6, 170.3, 173.2, 174.0.

MS (FAB$^+$): 421 (M+1).

EXAMPLE 16

(3R,6S,9S)-1-aza-9-carboxy-3-(9'-fluorenylmethoxycarbonyl amino)-2-oxo-bicyclo [4.3.0]nonane (Temp2)

Was prepared in quantitative overall yield following general procedure 1. $^1$HNMR—(200 MHz, $C_6D_6$, 323° K.) δ=1.1–2.0 (m, 8 H, 4 $CH_2$), 3.0 (m, 1 H, CH—N), 3.9 (m, 1 H, CH—NHFmoc), 4.12 (dd, J,=J2=6.5 Hz, 1 H, CH—$CH_2$O), 4.25–4.55 (m, 3 H, CHC02H, CH20), 6.02 (bs, 1 H, NH), 7.10–7.25 (m, 4 H, aromatic), 7.45–7.60 (m, 4 H, aromatic), 7.70 (bs, 1 H $CO_2$H). $^{13}$C NMR (50.3 MHz, CDC13) δ=27.7, 27.8, 28.1, 31.3, 47.0, 51.8, 58.6, 60.5, 67.0, 119.8, 125.1, 127.0, 127.6, 141.1, 143.8, 156.5, 170.0, 173.2, 174.3.

MS (FAB+): 421 (M+1).

EXAMPLE 17

(3S, 6R, 9S)-1-aza-9-carboxy-3-(9'-fluorenylmethoxycarbonyl-amino)-2-oxo-bicyclo [4.3.0]nonane (Temp3)

Was prepared in quantitative overall yield following general procedure 1. $^1$H-NMR (200 MHz, $C_6D_6$, 323° K.) δ=1.1–2.0 (m, 8 H, 4 $CH_2$), 3.0–3.2 (m, 1 H, CH—N), 4.20 (dd, $J_1=J_2$=7 Hz, 1 H, CH—$CH_2$O), 4.25–4.50 (m, 4 H, CH—NHFmoc, $CHCO_2$H, $CH_2$O), 6.43 (d, J=7 Hz, 1 H, NH), 7.10–7.30 (m, 4 H, aromatic), 7.40–7.80 (m, 4 H, aromatic), 10.80 (bs, 1 H, $CO_2$H). $^{13}$C-NMR (50.3 MHz, CDC13) δ=27.3, 27.4, 28.0, 32.5, 47.1, 51.9, 58.9, 60.2, 67.1, 119.8, 125.2, 127.0, 127.6, 141.2, 143.8, 143.9, 156.8, 169.5, 173.8. MS (FAB$^+$): 421 (M+1).

EXAMPLE 18

(3R,6R,9S)-1-aza-9-carboxy-3-(9'-fluorenylmethoxycarbonylamino)-2-oxo-bicyclo [4.3.0]nonane (Temp4)

Was prepared in quantitative overall yield following general procedure 1. $^1$H-NMR (200 MHz, $C_6D_6$, 323° K.) δ=0.8–1.9 (m, 8 H, 4 $CH_2$), 3.15 (m, 1 H, CH—N), 4.10 (dd, $J_1=J_2$=6 Hz, 1 H, CH—$CH_2$O), 4.30–4.6 (m, 4 H, CH—NHFmoc, $CHCO_2$H, $CH_2$O), 6.20 (bs, 1 H, NH), 7.10–7.30 (m, 4 H, aromatic), 7.50–7.60 (m, 4 H aromatic), 9.80 (bs, 1 H, $CO_2$H). $^{13}$C-NMR (50.3 MHz, $CDCl_3$) δ=25.3, 26.6, 27.5, 32.1, 46.9, 49.9, 57.7, 58.8, 67.2, 119.8, 125.1, 127.0, 127.6, 141.1, 143.7, 143.8, 156.6, 173.1, 174.2. MS (FAB+): 421 (M+1).

EXAMPLE 19

(3R; 7S,10S)-1-aza-10-carboxy-3-(9'-fluorenylmethoxycarbonyl-amino)-2-oxo-bicyclo [5.3.0]decane (Temp6)

Was prepared in quantitative overall yield following general procedure 1. $^1$H-NMR (200 MHz, $CDCl_3$) δ=1.6–2.3 (m, 10 H, 5 $CH_2$), 2.65 (s, 1 H, CH—$CH_2$O), 3.98 (m, 1 H, CH—N), 4.22 (m, 1 H, CH—$CO_2$H), 4.5 (m, 3 H, CH—NHFmoc, $CH_2$O), 6.3 (bs, 1 H, NH), 7.28–7.85 (m, 8 H, aromatic), 9.6 (bs, 1 H, $CO_2$H). $^{13}$C-NMR (50.3 MHz, $CDCl_3$) δ=22.02, 25.25, 26.63, 32.96, 46.92, 58.54, 60.60, 61.76, 68.74, 119.91, 124.77, 124.82, 127.00, 127.71. MS (FAB+): 435 (M+1).

EXAMPLE 20

(3R; 7S,1 OS)-1-aza-10-carboxy-3-(9'-fluorenylmethoxycarbonyl-amino)-2-oxo-bicyclo [5.3.0]decane (Temp6)

Was prepared in quantitative overall yield following general procedure 1. $^1$H-NMR (200 MHz, $CDCl_3$) δ=1.6–2.3 (m, 10 H, 5 $CH_2$), 2.65 (s, 1 H, CH—$CH_2$O), 3.98 (m, 1 H, CH—N), 4.22 (m, 1 H, CH—$CO_2$H), 4.5 (m, 3 H, CH—NHFmoc, $CH_2$O), 6.3 (bs, 1 H, NH), 7.28–7.85 (m, 8 H, aromatic), 9.6 (bs, 1 H, $CO_2$H). $^{13}$C-NMR (50.3 MHz, CDCl$_3$) δ=22.02, 25.25, 26.63, 32.96, 46.92, 58.54, 60.60, 61.76, 68.74, 119.91, 124.77, 124.82, 127.00, 127.7 1. MS (FAB+): 435 (M+1).

EXAMPLE 21

(3R,7R,10S)-1-aza-10-carboxy-3-(9'-fluorenylmethoxycarbonyl-amino)-2-oxo-bicyclo[5.3.0]decane (Temp7)

Was prepared in quantitative overall yield following general procedure 1. $^1$H-NMR (200 MHz, CDCl$_3$) δ=1.70–2.35 (m, 10 H, 5 CH$_2$), 2.70 (m, 1 H, CH—CH$_2$O), 4.05 (m, 1 H, CH—N), 4.25 (m, 1 H, CH—NHFmoc), 4.40 (m, 2 H, CHO), 4.65 (m, 1 H, CH—CO$_2$H), 6.15 (bs, 1 H, NH), 7.10–7.80 (8 H, aromatic). $^{13}$C-NMR (50.3 MHz, CDCl$_3$) δ=25.3, 26.9, 29.6, 32.1, 34.0, 47.0, 54.7, 59.4, 60.4, 67.1, 119.8, 119.9, 124.6, 125.1, 127.0, 127.5, 127.6, 131.1. MS (FAB+): 435 (M+1).

EXAMPLE 22

General Procedure 2. Preparation of N-Fmoc-Gly-O-Sasrin Resin.

In a solid phase reaction vessel, Sasrin resin (500 mg, 0.51 mmol) was suspended in a solution of N-Fmoc-Gly-OH (455 mg, 1.53 mmol), HOBt (206 mg, 1.53 mmol), DIC (0.24 ml, 1.53 mmol) and DMAP (19 mg, 0.15 mmol) in DMF (10 ml) for 15h. The solution was drained and the resin was washed with DMF (3×10 ml) and DCM (3×10 ml). The possibly unreacted hydroxy groups present were capped by treatment with a solution of acetic anhydride (0.096 ml, 1 mmol) and DMAP (57 mg, 0.51 mmol) in DMF (12 ml) for 2 h. The solution was drained and the resin washed with DMF (3×10 ml) and DCM (3×10 ml).

EXAMPLE 23

General Procedure 3. Preparation of N-Fmoc-Arg(Pmc)-Gly-O-Sasrin Resin.

In a solid phase reaction vessel, N-Fmoc-Gly-O-Sasrin resin (0.51 mmol) was treated with a 20% piperidine/DMF solution (10 ml, 1×3 min, 2×17 min). The solution was drained and the resin was washed with DMF (3×10 ml), MeOH (2×10 ml) and DCM (3×10 ml). The deprotection was assessed by performing a TNBS test. N-Fmoc-Arg(Pmc)-OH (1.014 g, 1.53 mmol) and HOAt (208 mg, 1.53 mmol) were dissolved in DCM/DMF 2:1 (10 ml). At 0° C., DIC (0.24 ml, 1.53 mmol) was added dropwise to this solution. The resulting mixture was stirred for 10 min at this temperature and for a further 10 min at room temperature, then added to the resin. This mixture was shaken at room temperature for 2.5 h. The solution was drained and the resin washed with DMF (3×10 ml) and DCM (3×10 ml). The success of the coupling was assessed by performing a TNBS test. The unreacted amino groups possibly present were capped by treatment with a solution of acetylimidazole (560 mg, 5.1 mmol) in DCM (12 ml) for 2 h. The solution was drained and the resin washed with DCM (3×10 ml).

EXAMPLE 24

General Procedure 4. Preparation of N-Fmoc-Temp-Arg(Pmc)-Gly-O-Sasrin Resin.

In a solid phase reaction vessel, N-Fmoc-Arg(Pmc)-Gly-O-Sasrin resin (0.51 mmol) was treated with a 20% piperidine/DMF solution (10 ml, 1×3 min, 2×17 min). The solution was drained and the resin was washed with DMF (3×10 ml), MeOH (2×10 ml) and DCM (3×10 ml). The deprotection was assessed by performing a TNBS test. The resin was suspended in a solution of N-Fmoc-Temp-OH (0.54 mmol), HATU (387 mg, 1.02 mmol), HOAt (139 mg, 1.02 mmol) and 2,4,6-collidine (0.135 ml, 1.02 mmol) in DMF/DCM 3:1 (13 ml) for 15 h. The solution was drained and the resin was washed with DMF (3×10 ml), MeOH (2×10 ml) and DCM (3×10 ml). The success of the coupling was assessed by performing a TNBS test. The unreacted amino groups possibly present were capped by treatment with a solution of acetylimidazole (560 mg, 5.1 mmol) in DCM (12 ml) for 2 h. The solution was drained and the resin was washed with DCM (3×10 ml).

EXAMPLE 25

General Procedure 5. Preparation of N-Fmoc-Asp(tBu)-Temp-Arg(Pmc)-Gly-O-Sasrin Resin.

In a solid phase reaction vessel, N-Fmoc-Temp-Arg(Pmc)-Gly-O-Sasrin resin (0.51 mmol) was treated with a 20% piperidine/DMF solution (10 ml, 1×3 min, 2×17 min). The solution was drained and the resin was washed with DMF (3×10 ml), MeOH (2×10 ml) and DCM (3×10 Ml). The deprotection was assessed by performing a TN-BS test. The resin was suspended in a solution of N-Fmoc-Asp(tBu)-OH (840 mg, 2.04 mmol), HATU (776 mg, 2.04mmol), HOAt (278 mg, 2.04 mmol) and 2,4,6-collidine (0.27 ml, 2.04 mmol) in DMF/DCM 3:1 (13 ml) for 15 h. The solution was drained and the resin was washed with DMF (3×10 ml), MeOH (2×10 ml) and DCM (3×10 ml). The success of the coupling was assessed by performing a TNBS test. The unreacted amino groups possibly present were capped by treatment with a solution of acetylimidazole (560 mg, 5.1 mmol) in DCM (12 Ml) for 2 h. The solution was drained and the resin was washed with DCM (3×10 ml).

EXAMPLE 26

General Procedure 6. Cleavage of H2N-Asp(tBu)-Temp-Arg(Pmc)-Gly-OH (1–7) from the Resin.

In a solid phase reaction vessel, N-Fmoc-Asp(tBu)-Temp-Arg(Pmc)-Gly-O-Sasrin resin (739 mg) was treated with a 20% piperidine/DMF solution (10 ml, 1×3 min, 2×17 min). The solution was drained and the resin was washed with DMF (3×10 ml), MeOH (2×10 ml) and DCM (3×10 ml). The deprotection was assessed by performing a TNBS test. The resin was treated with 1% TFA/DCM solution (7.4 ml×3 min). The filtrates were immediately neutralized with a 18% pyridine/MeOH solution (0.89 ml). The fractions containing the product (TLC DCM/MeOH 8:2) were combined and concentrated under reduced pressure to yield a residue, which was purified from the pyridinium salts by size-exclusion chromatography (AMBERLITE XAD-2 resin, H$_2$O then MeOH). Evaporation of the combined MeOH fractions containing the product afforded a yellow residue which was used in the successive reaction without further purification.

EXAMPLE 27

H2N-Asp(tBu)-Templ-Arg(Pmc)-Gly-OH (1). Was prepared from the corresponding template in 40% overall yield following general procedures 2–6. $^1$H NMR (300 MHz, CD$_3$OD) δ=1.30, 1.32 [2 s, 6 H, (CH$_3$)$_2$C—O], 1.43 [s, 9 H (CH$_3$)$_3$CO], 1.70 (m, 2 H, H-γ, Arg), 1.79–1.98 (m, 2 H, H-Cβ Arg), 1.85 (m, 2 H, CH$_2$CH$_2$Ar), 1.9 (m, 2 H, H-C$_4$ Temp), 2.1 (m, 4 H, H-C$_5$ Temp, H-C$_7$ Temp), 2.1 (s, 3 H CH$_3$Ar), 2.2 (m, 2 H, H-C$_8$ Temp), 2.4 (dd, J=9, 17, 1 H, H-C$_\beta$ Asp), 2.55, 2.57 (2s, 6 H, CH$_3$Ar), 2.65 (m, 3 H, H-C$_\beta$ Asp,CH$_2$CH$_2$Ar), 3.25 (m, 2 H, H-C$_{67}$ Arg), 3.65 (m, 1 H, H-C₆ Temp), 3.71 (d, J=17, 1 H, H-Cα Gly), 3.75–3.95 (m, 1 H, H-Cα Asp), 3.87 (m, 1 H, H-Cα Gly), 4.25 (m, 1 H, H-C₃ Temp), 4.4 (dd, J=0.8, 1 H, H-C₉ Temp), 4.88 (m, 1 H, H-Cα Arg). ¹³C-NMR (50.3 MHz, CD₃OD) δ=12.3, 17.9, 19.0, 22.4, 24.2, 27.0, 28.4, 29.0, 30.7, 33.8, 38.1, 41.4, 42.2, 48.4. 49.2, 50.5, 52.7, 55.2, 55.8, 62.2, 62.3. MS (FAB⁺): 849 (M+1).

EXAMPLE 28

H₂N-Asp (tBu)-Temp2-Arg(Pmc)-Gly-OH (2).

Was prepared from the corresponding template in 40% overall yield following general procedures 2–6. MS (FAB⁺): 849 (M+1).

EXAMPLE 29

H2N-Asp(tBu)-Temp3-Arg(Pmc)-Gly-OH (3). Was prepared from the corresponding template in 55% overall yield following general procedures 2–6. ¹H-NMR (300 MHz, CD₃OD) δ=1.30 [2 s, 6 H, (CH₃)₂C—O], 1.46 [s, 9 H, (CH₃)₃CO], 1.6 (m, 2 H, H-C₇ Temp), 1.70 (m, 2 H, H-Cγ Arg), 1.85 (m, 2 H, CH₂CH₂Ar), 1.95–2.2 (m, 2 H H-C4 Temp), 2.0 (m, 2 H, H-Cβ Arg), 2.1 (s, 3 H, CH₃Ar), 2.2 (m, 2 H, H-C₅ Temp), 2.4–2.6 (m, 2 H, H-Cβ Asp), 2.55–2.6 (2s, 6 H, CH₃Ar), 2.65 (m, 2 H, CH₂CH₂Ar), 2.9 (m, 2 H, H-C₈ Temp), 3.2 (m, 2 H, H-Cδ Arg), 3.6 (d, J=18, 1 H, H-Cα Gly), 3.80 (m, 1 H, H-C₆ Temp), 4.0 (m, 1 H, H-C₃ Temp), 4.05 (d, J=18, 1 H H-Cα Gly), 4.2 (dd, J=6,6, 1 H, H-C₉ Temp), 4.4 (m, 1 H, H-Cα Arg), 4.45 (m, 1 H, H-Cα Asp). ¹³C-NMR (50.3 MHz, CD₃OD) δ=12.3, 17.9, 19.0, 22.4, 27.0, 28.3, 28.6, 29.6, 30.0, 33.8, 37.0, 41.5, 43.3, 52.7, 54.2, 62.2, 74.9, 83.8, 119.4, 136.5, 169.7, 170.6, 173.9, 174.3. MS (FAB⁺): 849 (M+1).

EXAMPLE 30

H₂N-Asp(tBu)-Temp4-Arg(Pmc)-Gly-OH (4).

Was prepared from the corresponding template in 30% overall yield following general procedures 2–6. MS (FAB⁺): 850 (M+2).

EXAMPLE 31

H₂N-Asp(tBu)-Temp5-Arg(Pmc)-Gly-OH (5).

Was prepared from the corresponding template in 67% overall to yield following general procedures 2–6. MS (FAB⁺): 863 (M+1).

EXAMPLE 32

H₂N-Asp(tBu)-Temp6-Arg(Pmc)-Gly-OH (6).

Was prepared from the corresponding template in 54% overall yield following general procedures 2–6. MS (FAB⁺): 863 (M+1).

EXAMPLE 33

H₂ N-Asp(tBu)-Temp7-Arg(Pmc)-Gly-OH (7).

Was prepared from the corresponding template in 63% overall yield following general procedures 2–6. MS (FAB⁺): 863 (M+1).

EXAMPLE 34

H₂N-Asp(tBu)-Temp8-Arg(Pmc)-Gly-OH (8).

Was prepared from the corresponding template in 50% overall yield following general procedures 2–6. MS (FAB⁺): 863 (M+1).

EXAMPLE 35

General Procedure 7. Preparation of Cyclo[-Temp-Arg (Pmc)-Gly-Asp(tBu)-] (9–15). The linear peptide (0.18 mmol) was dissolved in DMF (45 ml) under N2. HATU (205 mg, 0.54 mmol), HOAt (73 mg, 0.54 mmol) and 2,4,6-collidine (0.072 ml, 0.54 mmol) were added and the resulting mixture was stirred for 24 h at room temperature. The solvent was evaporated under reduced pressure and the residue was dissolved in AcOEt. The organic phase was washed twice with 5% NaHCO₃, dried with Na₂SO₄ and evaporated under reduced pressure. The crude residue was purified by flash chromatography on silica gel (DCM/MeOH from 95:5 to 9:1) to afford side-chain protected cyclopeptide as a yellow foam.

EXAMPLE 36

Cyclo[-Temp1-Arg(Pmc)-Gly-Asp(tBu)-] (9).

Was prepared in 70% yield following general procedure 7. ¹H-NMR (300 MHz, CDCl₃) δ=1.25, 1.3 [2 s, 6 H (CH₃)₂C—O], 1.46 [s, 9 H, (CH₃)₃CO], 1.5 (m, 2 H, H-Cγ Arg), 1.6 (m, 2 H, H-C₄ Temp), 1.8 (m, 4 H, CH₂CH₂Ar, H-C₅ Temp), 2.0 (m, 2 H, H-Cβ Arg), 2.1 (s, 3 H, CH₃Ar), 2.2 (m, 4 H, H-C₇ Temp, H-C₈ Temp), 2.52, 2.56 (2 s, 6 H, CH₃Ar), 2.6 (m, 3 H, CH₂CH₂Ar, H-Cβ Asp), 3.1 (dd, J=5, 17.6, 1 H, H-Cβ Asp), 3.25 (m, 2 H, H-Cδ Arg), 3.55 (m, 1 H, H-C₆ Temp), 3.65 (dd, J=6, 13.6, 1 H, H-Cα Gly), 3.85 (dd, J=4, 13.6, 1 H, H-Cα Gly), 4.22 (dd, J=0, 9, 1 H H-C₉ Temp), 4.45 (m, 1 H, H-C₃ Temp), 4.54 (m, 1 H, H-Cα Arg), 4.68 (m, 1 H, H-Cα Asp), 6.3 (s, 3 H, H-Nε Arg, HNSO₂, =NH), 6.8 (d, J=6, 1 H, NH Temp), 7.61 (d, J=9, 1 NH Asp), 7.8 (d, J=8, 1 H, NH Arg), 8.9 (bs, 1 H, NHGly). ¹³C-NMR (75.4 MHz, CDCl₃) δ=12.1, 17.4, 18.5, 21.4, 25.2, 26.2, 26.8, 27.5, 28.0, 29.6, 31.4, 32.2, 32.9, 36.4, 40.2, 46.0, 47.7, 50.3, 51.9, 60.6, 62.1, 73.5, 81.8, 117.8, 123.8, 134.8, 134.9, 135.5, 153.3, 156.5, 168.0, 169.8, 170.2, 170.9, 173.6, 175.0. [α]$_D^{20}$=−36.1 (c=1.0, CHCl₃). MS (FAB⁺): 830 (M⁺), 853 (M+Na).

EXAMPLE 37

Cyclo[-Temp3-Arg(Pmc)-Gly-Asp(tBu)-] (10).

Was prepared in 60% yield following general procedure 7. ¹H-NMR (400 MHz, CDCl₃) δ=1.3 [2 s, 6 H, (CH₃)₂C—O], 1.45 [s, 9 H, (CH₃)₃CO], 1.5 (m, 4 H, H-Cγ Arg, H-C₇ Temp), 1.7 (m, 1 H, H-Cβ Arg), 1.8 (m, 3 H, CH₂CH₂Ar, H-C₈ Temp), 1.9 (m, 1 H, H-C₄ Temp), 2.0 (m, 1 H, H-Cβ Arg), 2.05 (s, 3 H CH₃Ar), 2.2 (m, 3 H, H-C₄ Temp, H-C₅ Temp), 2.50 (m, 2 H, H-Cβ Asp, H-C₈ Temp), 2.52, 2.56 (2 s, 6 H, CH₃Ar), 2.6 (m, 2 H, CH₂CH₂Ar), 2.80 (dd, J=8, 16, 1 H, H-Cβ Asp), 3.25 (m, 2 H, H-Cδ Arg ), 3.45 (dd, J=5, 16, 1 H, H-Cα Gly), 3.80 (m, 1 H, H-C₆ Temp), 4.10 (m, 1 H, H-C₃ Temp), 4.15 (m, 1 H, H-Cα Gly), 4.35 (dd, J=10, 10, 1 H, H-C₉ Temp), 4.5 (m, 1 H, H-Cα Arg), 4.70 (m, 1 H, H-Cα Asp), 6.22 (bs, 3 H, H-Nε Arg, HNSO₂, =NH), 7.1 (d, J=8, 1 H, NH Arg), 7.20 (d, J=8, 1 H, NH Asp), 7.70 (d, J=8, 1 H, NH Temp), 8.1 (bs, 1 H, NH Gly). ¹³C NMR (50.3 MHz, CDCl₃) δ=12.0, 17.4, 19.4, 21.3, 25.3, 26.7, 27.4, 27.9, 28.6, 29.6, 32.8, 36.7, 40.4, 45.1, 50.2, 50.7, 51.9, 60.7, 61.6, 73.5, 81.6, 117.8, 123.8, 133.7, 134.7, 135.3, 153.3, 156.3, 168.7, 169.8, 170.7, 171.4, 173.3. [α]$_D^{20}$=−57.1 (c=1.0, CHCl₃). MS (FAB⁺): 832 (M+2).

EXAMPLE 38

Cyclo[-Temp4-Arg(Pmc)-Gly-Asp(tBu)-] (11).

Was prepared in 40% yield following general procedure 7. ¹H-NMR (400 MHz, CDCl₃) δ=1.3 [2 s, 6 H (CH₃)₂C—O] =1.4 (m, 1 H, H-C₅ Temp), 1.45 [s, 9 H (CH₃)₃CO], 1.5–1.6 (m, 4 H, H-Cγ Arg, H-C₄ Temp, H-C₈ Temp), 1.8 (m, 2 H, CH₂CH₂Ar), 1.97 (m, 1 H, H-C₈ Temp), 2.0 (m, 4 H, H-Cγ

Arg, H-C$_4$ Temp, H-C$_5$ Temp), 2.15 (s, 3 H, CH$_3$Ar), 2.17, 2.43 (m, 2 H, H-C$_7$ Temp), 2.5 (m, 1 H, H-Cβ Asp), 2.60 (s, 3 H, CH$_3$Ar), 2.60 (m, 2 H, CH$_2$CH$_2$Ar), 2.62 (s, 3 H, CH$_3$Ar), 2.9 (dd, J=7, 17, 1 H, H-Cβ Asp), 3.2 (m, 2 H, H-Cδ Arg), 3.55 (dd, J=0, 12, 1 H H-Cα Gly), 4.05 (m, 1 H, H-C$_9$ Temp), 4.1 (m, 1 H, H-Cα Gly), 4.2 (m, 1 H, H-C$_6$ Temp), 4.3 (m, 1 H, H-C$_3$ Temp), 4.6 (m, 1 H, H-Cα Arg), 4.65 (m, 1 H, H-Cα Asp), 6.2–6.4 (bs, 3 H H-Nε Arg, HNSO$_2$, =NH), 7.3 (bs, 1 H, NH Temp), 7.45 (bs, 1 H NH Arg), 7.90 (bs, 1 H, NH Gly), 8.0 (bs, 1 H NH Asp). $^{13}$C-NMR (50.3 MHz, CDCl$_3$) δ=12.0, 17.4, 18.4, 21.3, 22.0, 25.6, 26.2, 26.7, 27.9, 30.1, 32.7, 34.0, 35.0, 50.9, 51.0, 51.8, 56.5, 62.5, 73.5, 81.2, 95.0, 117.8, 123.9, 133.3, 134.7, 135.3, 153.4, 156.2, 170.4, 170.7, 171.9, 172.5, 173.3. [α]$_D^{20}$=−71.0 (c=0.7, CHCl$_3$). MS (FAB$^+$): 832 (M+2).

EXAMPLE 39

Cyclo[-Temp5-Arg(Pmc)-Gly-Asp(tBu)-] (12).

Was prepared in 35% yield following general procedure 7. $^1$H-NMR (300 MHz, DMSO-D$_6$) δ=1.25, 1.38 [2 s, 6 H (CH$_3$)$_2$CO] 1.31 (m, 2 H, H-Cγ Arg), 1.38 [s, 9 H, (CH$_3$)$_3$CO], 1.8 (m, 2 H, CH$_2$CH$_2$Ar), 2.05 (s, 3 H, CH$_3$Ar), 2.05 (m, 1 H, H-C$_9$ Temp), 2,15 (m, 2 H, H-Cβ 5 Arg), 2.35 (dd, J=6.8, 17, 1 H H-Cβ Asp), 2.50,2,52 (2 s, 6 H, 3 CH$_3$Ar), 2.5 (m, 1 H, H-C$_9$ Temp), 2.6 (m, 2 H, CH$_2$CH$_2$Ar), 2.8 (dd, J=8.6, 17, 1 H, H-Cβ Asp), 3.1 (m, 2 H, H-Cδ Arg), 3.61 (d, J=9.8, 1 H, H-Cα Gly), 3.98 (d, J=9.8, 1 H, H-Cα Gly), 4.0 (m, 2 H, H-Cα Arg, H-C$_7$ Temp), 4.31 (m, 2 H, H-C$_3$ Temp, H-C$_{10}$ Temp), 4.55 (m, 1 H, H-Cα Asp), 6.48 (bs, 2 H, H-Nε Arg, HNSO$_2$), 6.78 (bs, 1 H, =NH), 7.68 (d, J=5.1, 1 H, NH Temp), 7.84 (bd, 1 NH Asp), 8.22 (m, 1 H, NH Arg), 8.5 (bt, 1 H, NH Gly). $^{13}$C-NMR (50.3 MHz, DMSO-D$_6$) δ=11.9, 17.1, 18.2, 26.4, 27.7, 20.8, 25.3, 27.0, 30.6, 32.2, 32.5, 36.3, 38.7, 40.3, 42.4, 49.6, 53.1, 58.8, 62.0, 73.5, 80.3. [α]$_D^{20}$=−36.7 (c=1, CHCl$_3$). MS (FAB$^+$): 844 (M+).

EXAMPLE 40

Cyclo[-Temp6-Arg(Pmc)-Gly-Asp(tBu)-] (13). Was prepared in 26% yield following general procedure 7.

$^1$H-NMR (300 MHz, DMSO-D$_6$) δ=1.3 [s, 3 H (CH$_3$)$_2$C—O], 1.31 (m, 2 H, H-Cγ Arg), 1.38 [s, 9 H, (CH$_3$)$_3$CO], 1.4 [s, 3 H (CH$_3$)$_2$C—O], 1.8–1.95 (m, 6 H, CH$_2$CH$_2$Ar, H-C$_9$ Temp, H-Cβ Arg), 2.05 (s, 3 H CH$_3$Ar), 2.39 (dd, J=4.3, 10.6, 1 H, H-Cβ Asp), 2.50, 2,52 (2 s, 6 H, 3 CH$_3$Ar), 2.6 (m, 2 H, CH$_2$CH$_2$Ar), 2.9 (dd, J=4.3, 10.6, 1 H H-Cβ Asp), 3.1 (m, 2 H H-Cδ Arg), 3.80 (m, 3 H, H-Cα Gly, H-Cα Arg), 4.3 (m, 1 H, H-C$_3$ Temp), 4.35 (m, 1 H, H-C$_{10}$ Temp), 4.48 (m, 1 H, H-Cα Asp), 6.45 (bs, 2 H, H-Nε Arg, HNSO$_2$), 6.60 (bs, 1 H, =NH), 7.5 (bd, 1 H, NH Asp), 7.51 (bd, 1 H, NH Temp), 8.55 (m, 1 H, NH Arg), 8.75 (bt, 1 H, NH Gly). $^{13}$C-NMR (75.4 MHz, CDCl$_3$) δ=12.1, 14.3, 17.5, 18.6, 21.4, 23.5, 26.8, 28.1, 29.7, 31.7, 32.8, 33.6, 49.7, 60.8, 73.6, 117.9, 124.0, 134.8, 135.5, 153.6, 171.5. [α]$_D^{20}$=−72.9 (c=1, CHCl$_3$), MS (FAB$^+$): 844 (M+).

EXAMPLE 41

Cyclo[-Temp7-Arg(Pmc)-Gly-Asp(tBu)-] (14). Was prepared in 15% yield following general procedure 7.

$^1$H-NMR (400 MHz, CDCl$_3$) δ=1.30 [s, 6 H, (CH$_3$)$_2$C—O], 1.41 [s, 9 H, (CH$_3$)$_3$CO], 1.49 (m, 1 H, H-Cγ Arg), 1.50–1.90 (10 H, CH$_2$CH$_2$Ar, H-C$_5$ Temp, H-C$_6$ Temp, H-C$_8$ Temp), 1.51 (m, 2 H, H-C$_4$ Temp), 1.60 (m, 1 H, H-Cγ Arg), 1.90 (m, 2 H, H-Cβ Arg), 1.98 (m, 1 H, H-C$_9$ Temp), 2.15 (s, 3 H CH$_3$Ar), 2.53 (s, 3 H, CH$_3$Ar), 2.58 (s, 3 H, CH$_3$Ar), 2.32 (m, 1 H, H-C$_9$ Temp), 2.51 (m. 1 H, H-Cβ Asp), 2.85 (m, 1 H, H-Cβ Asp), 3.20 (m, 2 H, H-Cδ Arg), 3.51 (bd, 1 H, H-Cα, Gly), 4.12 (m, 1 H, H-C$_7$ Temp), 4.18 (m, 1 H, H-Cα Gly), 4.32 (m, 1 H, H-C$_{10}$ Temp), 4.5 (m, 1 H, H-C$_3$ Temp), 4.58 (m, 1 H, H-Cα Arg), 4.80 (m, 1 H, H-Cα Asp), 6.3 (bs, 3 H, H-Nε Arg, HNSO$_2$, =NH, 7.2 (bd, 1 H, NH Arg), 7.65 (bd, 1 H, NH Temp), 7.80 (bt, 1 H, NH Gly), 7.95 (bd, 1 H, NH Asp).

EXAMPLE 42

Cyclo[-Temp8-Arg(Pmc)-Gly-Asp(tBu)-] (15). Was prepared in 55% yield following general procedure 7. $^1$H-NMR (400 MHz, CDCl$_3$) δ=1.27, 1.31 [2 s, 6 R (CH$_3$)$_2$C—O], 1.44 [s, 9 H, (CH$_3$)$_3$CO], 1.50 (m, 3 H, H-Cγ Arg, H-C$_6$ Temp), 1.60 (m, 2 H, H-Cβ Arg, H-Cγ Arg), 1.70 (m, 2 H, H-C$_8$ Temp), 1.8 (m, 2 H, CH$_2$CH$_2$Ar), 1.85 (m, 1 H, H-C$_4$ Temp), 1.95 (m, 2 H, H-Cβ Arg, H-C$_4$ Temp), 1.98 (m, 2 H, H-C$_5$ Temp), 2.11 (s, 3 H, CH$_3$Ar), 2.32 (m, 1 H, H-C$_9$ Temp), 2.56 (s, 3 H CH3Ar), 2.57 (dd, J=7.4, 16.7, 1 H, H-Cβ Asp), 2.58 (s, 3 H CH$_3$Ar), 2.65 (m, 2 H, CH$_2$CH$_2$Ar), 2.87 (dd, J=7.4, 16.7, 1 H, H-Cβ Asp), 3.20 (m, 2 H, H-C$_3$ Arg), 3.54 (bd, 1 H, H-Cα Gly), 4.18 (m, 1 H, H-Cα Gly), 4.22 (m, 1 H, H-C$_7$ Temp), 4.36 (m, 1 H, H-C$_{10}$ Temp), 4.55 (m, 1H, H-C$_3$ Temp), 4.6 (m, 1 H, H-Cα Arg), 4.83 (m, 1 H, H-Cα Asp), 6.33 (bs, 3 H, H-Nε Arg, HNSO$_2$, =NH), 7.49 (bd, 1 H, NH Arg), 7.71 (bt, 1 H, NH Gly), 7.80 (bd, 1 H, NH Temp), 7.95 (bd, 1 H, NH Asp). $^{13}$C NMR (50.3 MHz, CDCl$_3$) δ12.0, 17.4, 18.4, 26.7, 27.4, 36.4, 21.4, 25.3, 28.5, 29.6, 30.8, 33.0, 34.9, 40.6, 44.3, 49.9, 51.9, 54.1, 59.3, 63.2, 73.5, 81.3, 117.8, 123.9, 133.4, 134.7, 135.3, 153.5, 156.3, 170.3, 170.5, 172.3, 172.6. [α]$_D^{20}$=−54 (c=0.05, CHCl$_3$). MS (FAB$^+$): 844 (M+).

EXAMPLE 43

General Procedure 8. Preparation of Cyclo(-Temp-Arg-Gly-Asp-) (16–22).

Side-chain protected cyclopeptide (0.1 mmol) was treated with TFA/thioanisole/1,2-ethanedithiol/anisole 90:53:2 (35 ml) for 2 h. The reaction mixture was evaporated under reduced pressure and the residue was dissolved in H20. The aqueous phase was washed twice with iPr$_2$O and evaporated under reduced pressure to afford side-chain deprotected cyclopeptide as a white foam. Trifluoroacetate ion was substituted with chloride by ion-exchange chromatography (AMBERLITE IRA-93 resin, chloride form).

EXAMPLE 44

Cyclo(-Temp1-Arg-Gly-Asp-) (16). Was prepared in quantitative yield following general procedure 8. $^1$H-NMR (400 MHz, D$_2$O) δ=1.6–1.75 (m, 2 H, H-Cγ Arg), 1.65–1.95 (m, 6 H, H-C$_4$ Temp, H-C$_5$ Temp, H-C$_7$ Temp), 2.2 (m, 2 H, H-Cβ Arg), 2.3–2.45 (m, 2 H, H-C$_8$ Temp), 2.73 (dd, J=0, 6, 2 H, H-Cβ Asp), 3.25–3.50 (m, 2 H, H-Cδ Arg), 3.8–3.95 (m, 1 H, H-C$_6$ Temp), 3.82 (d, J=13.5, 1 H, H-Cα Gly), 4.25 (d, J=13.5, 1 H, H-Cα Gly), 4.50 (dd, J=0, 10, 1 H, H-C$_9$ Temp), 4.55 (dd, J=0, 8, 1 H, H-Cα, Arg), 4.58 (m, 1 H, H-C$_3$ Temp), 4.75 (m, 1 H, H-Cα Asp). $^{13}$C NMR (75.4 MHz, D$_2$O) δ=25.0, 26.4, 28.2, 29.8, 30.8, 32.2, 39.0, 41.3, 45.8, 48.3, 52.7, 53.1, 61.7, 62.6, 157.7, 170.1, 172.6, 174.0, 175.4, 175.7, 178.4. [α]$_D^{20}$=−52.6 (c=0.88, H$_2$O). MS (FAB+: 509 (M+1)

EXAMPLE 45

Cyclo(-Temp3-Arg-Gly-Asp-) (17). Was prepared in quantitative yield following general procedure 8. $^1$H-NMR (400 MHz, D$_2$O) δ=1.5 (m, 2 H, H-C$_5$ Temp), 1.6 (m, 2 H, H-Cβ Arg), 1.8 (m, 2 H, H-C₄ Temp), 1.9 (m, 2 H, H-Cγ Arg), 2.2 (m, 2 H, H-C₇ Temp), 2.42–2.52 (m, 2 H, H-C₈ Temp), 2.7–2.85 (m, 2 H, H-Cβ Asp), 3.15–3.30 (m, 2 H, H-Cδ Arg), 3.55 (d, J=14, 1 H, H-Cα Gly), 3.83–3.95 (m, 1 H, H-C₆ Temp), 4.10 (d, J=14, 1 H, H-Cα Gly), 4.28 (m, 1 H, H-C₃ Temp), 4.37 (dd, J=0, 9, 1 H, H-C₈ Temp), 4.45 (dd, J=5, 10, 1 H, H-Cα Arg), 4.65 (m, 1 H, H-Cα Asp). ¹³C-NMR (50.3 MHz, D₂O) δ=27.1, 29.3, 30.4, 31.4, 31.8, 35.1, 38.1, 43.3, 47.2, 52.8, 53.5, 54.8, 64.0, 64.5, 159.6, 166.1, 172.5, 174.8, 175.2, 176.4, 176.6, 177.9. $[α]_D^{20}$=−94.6 (c=1.32, H₂O) MS (IS⁺): 508 (M+).

EXAMPLE 46

Cyclo(-Temp4-Arg-Gly-Asp-) (18). Was prepared in quantitative yield following general procedure 8. This compound was not stable in aqueous solution over a few days at room temperature. ¹H-NMR (400 MHz, D₂O) δ=1.6–1.7 (m, 2 H, H-C₄ Temp), 1.7 (m, 2 H, H-Cγ Arg), 2.0 (m, 2 H, H-C₇ Temp), 2.2 (m, 2 H, H-Cβ Arg), 2.4 (m, 2 H, H-C₅ Temp), 2.6 (m, 2 H, H-C₈ Temp), 2.70 (dd, J=7, 17, 1 H, H-Cβ Asp), 3.05 (dd, J=7, 17, 1 H, H-Cβ Asp), 3.15–3.25 (m, 2 H, H-C₈ Arg), 3.52 (d, J=15, 1 H, H-Cα Gly), 4.05 (m, 1 H, H-C₆ Temp), 4.28 (d, J=15, 1 H, H-Cα Gly), 4.3 (m, 1 H, H-C₃ Temp), 4.35 (m, 1 H, H-C₁₀ Temp), 4.53 (dd, J=7, 7, H-Cα Asp), 4.6 (m, 1H, H-Cα Arg). $[α]_D^{20}$=−63.7 (c=0.95, H₂O). MS (IS⁺): 508 (M+).

EXAMPLE 47

Cyclo(-Temp5-Arg-Gly-Asp-) (19). Was prepared in quantitative yield following general procedure 8. ¹H-NMR (400 MHz, D₂O) δ=1.5–1.8 (m, 2 H, H-Cγ Arg), 1.7–2.0 (m, 2 H, H-Cβ Arg), 2.8 (m, 2 H, H-Cβ Asp), 3.22 (m, 2 H, H-CδArg), 4.0 (m, 2 H, H-Cα Gly, H-C₇ Temp), 4.3 (dd, J=7, 7, 1 H, H-Cα Arg), 4.5–4.6 (m, 1 H, H-C₃ Temp, H-C₁₀ Temp), 4.68 (m, 1 H H-Cα Asp). ¹³C-NMR (50.3 MHz, D2O) δ=27.2, 29.8, 30.1, 31.0, 33.6, 35.3, 36.2, 39.0, 43.3, 45.7, 53.8, 56.3, 62.8, 65.2, 159.5, 174.3, 174.4, 175.6, 176.4, 178.5. $[α]_D^{20}$=−87.4 (c=1.2, H₂O). MS (IS⁺): 522 (M+).

EXAMPLE 48

Cyclo(-Temp6-Arg-Gly-Asp-) (20). Was prepared in quantitative yield following general procedure 8. ¹H-NMR (400 MHz, D₂O) δ=1,5–1.8 (m, 2 H, H-C₆ Temp), 1.6 (m, 2 H, H-Cγ Arg), 1.75–1.9 (m, 2 H, H-Cβ Arg), 1.8–1.95 (m, 2 H, H-C₄ Temp), 2.15 (m, 4 H, H-C₈ Temp, H-C₉ Temp), 2.65–2.8 (m, 2 H, H-Cβ Asp), 3.2 (m, 2 H, H-Cδ mArg), 3.82 (d, J=17, 1 H, H-Cα Gly), 4.05 (d, J=17, 1 H H-Cα Gly), 4.1 (m, 1 H, H-C₇ Temp), 4.37 (dd, J=0, 7, 1 H, H-C₁₀ Temp), 4.42 (dd, J=0, 10, 1 H, H-C₃ Temp), 4.52 (dd, J=5, 10, 1 H, H-Cα Arg), 4.70 (m, 1 H, H-Cα Asp). ¹³C-NMR (75.4 MHz, D2O) δ=22.3, 25.0, 25.9, 28.7, 30.4, 33.7, 34.2, 37.7, 41.4, 43.2, 51.5, 53.3, 57.5, 59.1, 63.6, 157.6, 171.6, 173.7, 174.2, 175.0, 176.9. $[α]_D^{20}$=−47.9 (c=0.71, H₂O). MS (IS⁺): 522 (M+).

EXAMPLE 49

Cyclo(-Temp8-Arg-Gly-Asp-) (22). Was prepared in quantitative yield following general procedure 8. ¹H-NMR (400 MHz, DO) δ=1.4 (m, 3 H, H-C₅ Temp, H-C₈ Temp), 1.55–1.7 (m, 2H, H-Cγ Arg), 1.8 (m, 4 H, H-C₄ Temp, H-C₈ Temp, H-C₉ Temp), 2.0 (m, 2 H, H-Cβ Arg), 2.26 (m, 2 H, H-C₆ Temp), 2.38 (m, 1 H, H-C₉ Temp), 2.68 (dd, J=7, 18, 1 H, H-Cα Asp), 2.98 (dd, J=7,18, 1 H, H-Cα Asp), 3.2 (m, 2 H, H-Cγ Arg), 3.5 (d, J=15, 1 H, H-Cα Gly), 4.2 (d, J=15, 1 H, H-Cα Gly), 4.2 (m, 1 H, H-C₇ Temp), 4.38 (m, 1 H, H-C₁₀ Temp), 4.48 (dd, J=5, 11, 1 H, H-Cα Arg), 4.53 (dd, J=0, 11, 1 H, H-C₃ Temp), 4.63 (dd, J=7, 7, 2 H, H-Cβ Asp). ¹³C-NMR (75.4 MHz, D20) δ=27.4, 29.3, 30.2, 30.6, 33.0, 35.1, 36.2, 41.3, 46.1, 53.8, 54.9, 56.8, 62.8, 66.1, 159.5, 174.2, 174.8, 175.9, 176.4, 177.6. $[α]_D^{20}$=−38.1 (c=1.2, H₂O). MS (IS⁺): 522 (M+).

What is claimed is:

1. A process for the preparation of a compound of formula I

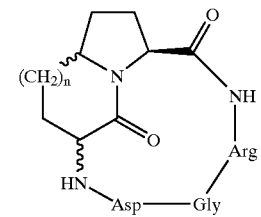

(I)

where n is 0, 1 or 2, and

Arg is the amino acid L-Arginine, Gly is the amino acid Glycine and Asp is the amino acid L-Aspartic acid or a salt thereof, or a racemate, a single enantiomer or diastereoisomer thereof, said process comprising the steps of:

a) Horner-Emmons olefination of a compound of formula (II)

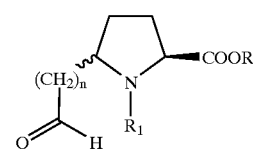

(II)

wherein R is a lower alkyl residue, and R₁ is a nitrogen protecting group, to give a compound of formula (III);

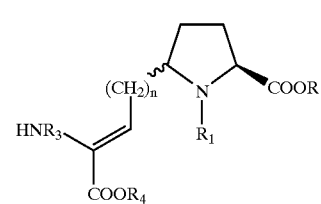

(III)

where R₃ is a nitrogen protecting group and R₄ is a lower alkyl residue;

b) hydrogenation of the compound of formula (III) and cyclization;

c) if desired separating the stereoisomeric mixture;

d) inserting the RGD cyclic sequence;

e) if desired, separating the stereo isomeric mixture, and thereafter f) separating the compound of formula (I).

2. A process for the stereoselective synthesis of a compound of the formula (I)

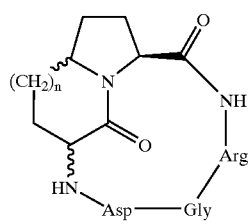

(I)

where n is 0, 1 or 2, and

Arg is the amino acid L-Arginine, Gly is the amino acid Glycine and Asp is the amino acid L-Aspartic acid or a salt thereof, or a racemate, a single enantiomer or diastereoisomer thereof, said process comprising the steps of a) Horner-Emmons olefination of a compound of formula (II)

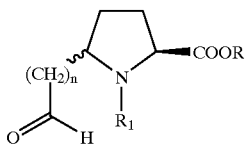

(II)

wherein R is a lower alkyl residue; and $R_1$ is a nitrogen protecting group, to give a compound of formula (III):

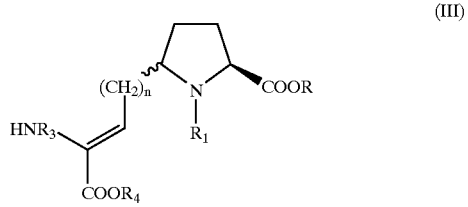

(III)

where $R_3$ is a nitrogen protecting group, $R_4$ is a lower alkyl residue;

b) hydrogenation of the compound of formula (III) by chiral phosphine-Rh catalyzed hydrogenation and cyclization;
c) if desired, separating the stereoisomeric mixture;
d) inserting the RGD cyclic sequence;
e) if desired, separating of the stereoisomeric mixture, and
f) separating the compound of formula (I).

* * * * *